US008455448B2

(12) United States Patent
Jeanplong et al.

(10) Patent No.: US 8,455,448 B2
(45) Date of Patent: Jun. 4, 2013

(54) MYOSTATIN ISOFORM

(75) Inventors: Ferenc Jeanplong, Hamilton (NZ); Christopher David McMahon, Hamilton (NZ)

(73) Assignee: Myostin Therapeutics Pty Ltd, Victoria (AU)

(*) Notice: Subject to any disclaimer, the term of this patent is extended or adjusted under 35 U.S.C. 154(b) by 0 days.

(21) Appl. No.: 13/085,263

(22) Filed: Apr. 12, 2011

(65) Prior Publication Data

US 2011/0258712 A1 Oct. 20, 2011

Related U.S. Application Data

(63) Continuation of application No. 11/576,449, filed as application No. PCT/NZ2005/000250 on Sep. 30, 2005, now abandoned.

(30) Foreign Application Priority Data

Sep. 30, 2004 (NZ) ........................................ 535696
Feb. 22, 2005 (NZ) ........................................ 538396

(51) Int. Cl.

*A61K 38/10* (2006.01)
*A61K 38/16* (2006.01)
*A61K 35/34* (2006.01)
*A61P 21/00* (2006.01)

(52) U.S. Cl.
USPC ....... 514/21.4; 514/21.2; 514/21.3; 514/12.1; 424/548

(58) Field of Classification Search
None
See application file for complete search history.

(56) References Cited

U.S. PATENT DOCUMENTS

| | | | | |
|---|---|---|---|---|
| 4,179,337 | A | 12/1979 | Davis et al. | |
| 4,487,325 | A | 12/1984 | Willingham | |
| 6,207,160 | B1 | 3/2001 | Victoria et al. | |
| 7,368,534 | B2 * | 5/2008 | Bass et al. | 530/350 |
| 8,309,068 | B2 * | 11/2012 | Kambadur et al. | 424/85.2 |
| 2007/0190056 | A1 | 8/2007 | Kambadur et al. | |

FOREIGN PATENT DOCUMENTS

| | | | |
|---|---|---|---|
| JP | 2002504326 | A | 2/2002 |
| JP | 2004504826 | A | 2/2004 |
| WO | WO 98/33887 | A1 | 8/1998 |
| WO | WO 99/42573 | * | 8/1999 |
| WO | WO 99/42573 | A1 | 8/1999 |
| WO | WO 01/05820 | A2 | 1/2001 |
| WO | WO 01/53350 | A1 | 7/2001 |
| WO | WO 02/09641 | A2 | 2/2002 |
| WO | WO 02/10214 | A2 | 2/2002 |
| WO | WO 2004/011650 | A2 | 2/2004 |
| WO | WO 2004/024890 | A2 | 3/2004 |
| WO | WO 2005/051993 | A1 | 6/2005 |
| WO | WO 2005/066204 | A2 | 7/2005 |
| WO | WO 2006/083183 | A1 | 8/2006 |

OTHER PUBLICATIONS

Gonzalez-Cadavid, PNAS, 1998, 95, 14938-14943.*
Kambadur, 1997, Genome Research, 7, 910-915.*
Dooley, H. et al. 2003 "Selection and characterization of naturally occurring single-domain (IgNAR) antibody fragments from immunized sharks by phage display" *Molec Immunol* 40:25-33.
Genbank Accession No. NM_001001525, Apr. 29, 2010.
Jeanplong, F. et al. 2001 "Genomic organization and neonatal expression of the bovine myostatin gene" *Mol Cell Biochem* 220:31-37.
Lee, S.-J. et al. 2001 "Regulation of myostatin activity and muscle growth" *Proc Natl Acad Sci USA* 98:9306-9311.
Sharma, M. et al. 1999 "Myostatin, a transforming growth factor-β superfamily member is expressed in heart muscle and is upregulated in cardiomyocytes after infarct" *J Cell Phys* 180: 1-9.
Dunner, S. et al. 2003 "Haplotype diversity of the myostatin gene among beef cattle breeds" *Genet Sel, Evol* 35: 103-118.
Gonzalez-Cadavid, N.F. et al. 1998 "Organization of the human myostatin gene and expression in healthy men and HIV-infected men with muscle wasting" *PNAS USA* 95: 14938-14943.
Kambadur, R. et al. 1997 "Mutations in *myostatin* (GDF8) in Double-Muscled Belgian Blue and Piedmontese Cattle" *Genome Res.* 7: 910-916.
Sawada, Y. et al. 1997 "Stretch-induced Hypertrophic Growth of Cardiocytes and Processing of Brain-type Natriuretic Peptide Are Controlled by Proprotein-processing Endoprotease Furin" *J Biol Chem* 272: 20545.20554.
Castelhano-Barbosa, E.C. et al. 2005 "Temporal and spatial expression of the Myostatin gene during chicken embryo development" *Growth, Development & Aging* 69:3-12. Jiang, M.-S. et al. 2004 "Characterization and identification of the inhibitory domain of GDF-8 propeptide" *Biochem and Biophys Res Comm* 315:525-531.
Nicholas, G. et al. 2002 "Titin-Cap associates with, and regulates secretion of, Myostatin" *J Cellular Physiol* 193:120-131.

* cited by examiner

*Primary Examiner* — Satyanarayana R Gudibande
(74) *Attorney, Agent, or Firm* — Knobbe Martens Olson & Bear LLP

(57) ABSTRACT

The present invention provides splice variants of myostatin that promote muscle growth, and include polynucleotides and polypeptide sequences, constructs comprising the sequences and compositions for regulating muscle growth and treating diseases associated with muscle tissue. The splice variants include the consensus sequence $X_1$ I F L E $X_2$ $X_3$ $X_4$ Q $X_5$ C S I L $X_6$ $X_7$ $X_8$ $X_9$ $X_{10}$ wherein $X_1$ is I or L, $X_2$ is V or L, $X_3$ is Y, C, G or S, $X_4$ is I or F, $X_5$ is F or L, $X_6$ is G or E, $X_7$ is E or V, $X_8$ is A or T, $X_9$ is A or V and $X_{10}$ is absent, F or L. The present invention also provides for the use of the present sequences in identifying animals with altered muscle mass, and for use in selective breeding programs to produce animals with altered muscle mass.

4 Claims, 19 Drawing Sheets

MYOSTATIN ISOFORM

RELATED APPLICATIONS

This application is a continuation of U.S. application Ser. No. 11/576,449, filed Sep. 19, 2007, which is the U.S. National Phase of International Application PCT/NZ2005/000250, filed Sep. 30, 2005 designating the U.S., and published in English as WO 2006/036074 on Apr. 6, 2006, which claims priority to New Zealand Patent Application No. NZ 535696 filed Sep. 30, 2004 and New Zealand Patent Application No. NZ 538396 filed Feb. 22, 2005.

REFERENCE TO SEQUENCE LISTING

The present application is filed along with a Sequence Listing in electronic format. The Sequence Listing is provided as a file entitled 14520103_1.txt, created Dec. 18, 2012, which is approximately 49 Kb in size. The information in the electronic format of the Sequence Listing is incorporated herein by reference in its entirety.

FIELD OF THE INVENTION

The present invention is based upon the identification of a novel splice variant of myostatin. In particular, the present invention is based on the use of the myostatin splice variant to modulate or regulate muscle growth and myostatin activity.

BACKGROUND

Myostatin (or GDF-8) is a negative regulator of muscle growth and is structurally related to the transforming growth factor β (TGF-β) superfamily (McPherron et al 1997a). More particularly, myostatin is a potent negative regulator of skeletal muscle during development, and in adult life, in a wide range of species from fish to mammals (McPherron and Lee, 1997). Myostatin is known to regulate its own expression via a mechanism that is incompletely understood at present (Berry et al. 2002, Spiller et al. 2002, Rebbapragada et al. 2003).

The myostatin protein is initially translated as a 375 amino acid precursor molecule having a secretory signal sequence at the N-terminus, a proteolytic processing signal (RSRR) of the furin endoprotease, and nine conserved cysteine residues in the C-terminal region to facilitate the formation of a "cysteine knot" structure. Myostatin is activated by furin endoprotease cleavage at Arg 266 releasing the N-terminal, or "latency-associated peptide" (LAP) and the mature, C-terminal domain, which dimerises to form the active myostatin molecule. After processing, a homodimer of the LAP peptide remains non-covalently bound to the homodimer of mature myostatin in an inactive complex (Lee et al. 2001). Other proteins, for example, follistatin, titin cap, GDFP1, follistatin related gene and hSGT are also known to bind to and regulate the secretion and activation of the latent myostatin complex (Lee et al. 2001, Nicolas et al. 2002, Hill et al. 2002, Hill et al. 2003, Wang et al. 2003).

It has been demonstrated that myostatin inhibits myoblast proliferation and differentiation without inducing apoptosis or stimulating muscle protein breakdown (Thomas et al. 2000, Langley et al. 2002, Rios et al. 2001, Taylor et al. 2001). Knock-out mice for myostatin have greatly increased muscle mass over their entire body. Myostatin-null mice have approximately 30% greater body weight than normal mice, and exhibit a 2-3-fold increase in individual muscle weights due to muscle fibre hyperplasia and hypertrophy. Natural mutations in myostatin have been identified as being responsible for the "double-muscled" phenotype, such as the Belgian Blue and Piedmontese cattle breeds (McPherron et al 1997b, Kambadur et. al. 1997, Grobet et al. 1997).

Myostatin has also been linked with many other biological processes. For example, knockout transgenic mice have altered cortical bone structure indicating a role in osteogenesis (Hamrick 2003). Furthermore, myostatin has been shown to be involved in regulating glucose and fat metabolism, thus it may be implicated in type 2 diabetes and obesity (McPherron and Lee 2002).

In accordance with these effects, myostatin has been implicated in a number of disorders associated with muscle wasting, or muscle atrophy, such as that seen in individuals affected by HIV, cancer, prolonged bed rest, or muscular dystrophy (Gonzalez-Cadavid et al. 1998, Langley et al 2004, Zachwieja et al 1999, Bogdanovich et al. 2002). It was demonstrated that in vivo administration of myostatin induces cachexia, a severe form of muscle wasting associated with cancer and sepsis (Zimmers et al. 2002). Furthermore, up-regulation of myostatin in glucocorticoid-induced muscle atrophy has been observed (Ma et al. 2003). Changes in myostatin expression have been shown in other conditions, for example, up-regulated in cardiomyocytes after heart damage, and down regulated in regenerating muscle (Sharma et al. 1999).

Despite the available information, complexity in the molecular regulation of biological processes by products of the myostatin gene remains incompletely understood. Given the role of myostatin in regulation of muscle growth and differentiation, tissue regeneration, clearly there is a need for improved compositions and methods to intervene in these and other processes in which myostatin plays a role. The present invention fulfils these needs, in part by providing a novel, biologically active myostatin splice variant, and also offers other related advantages.

SUMMARY OF INVENTION

In one aspect the present invention provides for an isolated polypeptide comprising an amino acid sequence having the formula:

$$X_1 \text{ I F L E } X_2 X_3 X_4 \text{ Q } X_5 \text{ C S I L } X_6 X_7 X_8 X_9 X_{10} \text{ (SEQ ID NO: 134)}$$

wherein $X_1$ is I or L, $X_2$ is V or L, $X_3$ is Y, C, G or S, $X_4$ is I or F; $X_5$ is F or L, $X_6$ is G or E, $X_7$ is E or V, $X_8$ is A or T, $X_9$ is A or V, and $X_{10}$ is absent, F or L.

The isolated polypeptide can also be selected from:
(a) a polypeptide comprising an amino acid sequence of any one of SEQ ID NOS: 48-95;
(b) a polypeptide that comprises a fragment or variant of a polypeptide in (a); and
(c) a polypeptide having 95%, 90%, 80% or 70% sequence identity with a polypeptide of (a).

The isolated polypeptide according to the present invention also includes an amino acid sequence of any one of SEQ ID NOS: 48-95 or a variant thereof having at least 80% sequence identity, wherein the peptide is capable of promoting myoblast cell growth.

The invention also provides for an isolated polynucleotide comprising a nucleotide sequence that encodes a polypeptide as disclosed herein, or a complementary sequence thereto.

An isolated polynucleotide according to the present invention can be selected from:
(a) a polynucleotide comprising a nucleotide sequence of any one of SEQ ID NOS: 1 to 47 or 96;

(b) a polynucleotide that comprises a fragment or variant of a polynucleotide in (a);
(c) a polynucleotide having 95%, 90%, 80% or 70% sequence identity with a polynucleotide in (a);
(d) a polynucleotide which comprises a nucleotide sequence that is a complement of any one of (a) to (c); and
(e) a reverse complement of any one of (a) to (c).

The isolated polynucleotides includes a nucleotide sequence of any one of SEQ ID NOS: 1 to 47 or 96 or a variant thereof having 80% sequence identity that encodes a peptide that is capable of promoting myoblast cell growth.

The invention also provides for a vector comprising the polynucleotide sequences according to the present invention. The vector can be an expression vector, and can comprising in operable linkage:
(a) a promoter sequence;
(b) a polynucleotide according to the present invention; and
(c) a gene termination sequence.

The polynucleotide can either be in a sense orientation or in an antisense orientation.

Host cell comprising a such vectors are also included, along with host animals comprising one or a plurality of cells which contain a vector according to the present invention.

The invention also provides for a composition for regulating muscle growth, comprising a compound of any one of:
(a) a polypeptide as disclosed herein,
(b) a polynucleotide as disclosed herein,
(c) a vector as disclosed herein,
(d) a fragment or variant of (a);
(e) a complement of any one of (b);
(f) a reverse complement of (b); and
(g) an antisense polynucleotide of any one of (b), (e) or (f).

The composition can include an anti-sense polynucleotide, including an interfering RNA molecule such as an RNAi or siRNA.

The invention also provides for a method for regulating muscle growth, comprising administering a composition that is selected from the group consisting of:
(a) a polypeptide according to the present invention;
(b) a polynucleotide comprising a nucleotide sequence that encodes a polypeptide according to the present invention, or a complementary sequence thereto;
(c) a polynucleotide that is selected from the group consisting of:
(i) a polynucleotide comprising a nucleotide sequence of any one of SEQ ID NOS: 1 to 47 to 96
(ii) a polynucleotide that comprises a fragment or variant of a polynucleotide in (i),
(iii) a polynucleotide having 95%, 90%, 80% or 70% sequence identity with a polynucleotide in (i), and
(iv) a polynucleotide which comprises a nucleotide sequence that is a complement of any one of (i) to (iii);
(d) a vector comprising the polynucleotide of (b) or (c);
(e) a vector comprising the polynucleotide of (b) or (c) wherein the vector is an expression vector;
(f) a vector comprising in operable linkage; a promoter, a polynucleotide according to (b) or (c) and a gene termination sequence; and
(g) an antisense polynucleotide that is capable of inhibiting or substantially impairing expression of a polypeptide product by (b) or (c).

The invention also provides for a method for treating a disease associated with muscle tissue, comprising administering a composition that is selected from the group consisting of:
(a) a polypeptide according to the present invention;
(b) a polynucleotide comprising a nucleotide sequence that encodes a polypeptide according to the present invention, or a complementary sequence thereto;
(c) a polynucleotide that is selected from the group consisting of:
(i) a polynucleotide comprising a nucleotide sequence of any one of SEQ ID NOS: 1 to 47 or 96,
(ii) a polynucleotide that comprises a fragment or variant of a polynucleotide in (i),
(iii) a polynucleotide having 95%, 90%, 80% or 70% sequence identity with a polynucleotide in (i), and
(iv) a polynucleotide which comprises a nucleotide sequence that is a complement of any one of (i) to (iii);
(d) a vector comprising the polynucleotide of (b) or (c);
(e) a vector comprising the polynucleotide of (b) or (c) wherein the vector is an expression vector;
(f) a vector comprising in operable linkage a promoter, a polynucleotide according to (b) or (c) and a gene termination sequence; and
(g) an antisense polynucleotide that is capable of inhibiting or substantially impairing expression of a polypeptide product by (b) or (c).

The method can be to treat a disease associated with muscle tissue comprises a condition that is associated with muscle atrophy and may be selected from the group consisting of muscular dystrophy, muscle cachexia, atrophy, hypertrophy, disease-associated muscle atrophy and amyotrophic lateral sclerosis (ALS). The method also includes the treatment of a disease-associated muscle wasting associated with cancer or HIV/AIDS.

The disease also includes a disease associated with cardiac muscle, such as comprises infarct.

The present invention also provides for a modulator of MSV gene expression comprising a composition that is able to specifically bind to a polynucleotide selected from the group consisting of:
(a) a polynucleotide comprising a nucleotide sequence that encodes a polypeptide as disclosed herein, or a complementary sequence thereto;
(b) a polynucleotide that is selected from the group consisting of:
(i) a polynucleotide comprising a nucleotide sequence of any one of SEQ ID NOS: 1 to 47 or 96,
(ii) a polynucleotide that comprises a fragment or variant of a polynucleotide in (i),
(iii) a polynucleotide having 95%, 90%, 80% or 70% sequence identity with a polynucleotide in (i), and
(iv) a polynucleotide which comprises a nucleotide sequence that is a complement of any one of (i) to (iii);
(c) an antisense polynucleotide that is capable of inhibiting or substantially impairing expression of a polypeptide product by (a) or (b); and
(d) an interfering RNA molecule.

The modulator of MSV gene can comprises an anti-sense polynucleotide, such as an RNAi or siRNA molecule.

The present invention also provides for a method for treating a disease associated with muscle tissue in a patient, comprising administering to said patient a modulator according to the present invention. The disease can be muscle atrophy, and may be selected from the group consisting of muscular dystrophy, muscle cachexia, atrophy, hypertrophy, disease-associated muscle atrophy, and amyotrophic lateral sclerosis (ALS). The disease may also be a disease-associated muscle atrophy comprising muscle wasting associated with cancer or HIV/AIDS.

The disease can also be associated with cardiac muscle, and includes infarct.

The present invention also provides for a method for modulating MSV activity, comprising contacting a MSV propeptide with a propeptide convertase, under conditions and for a time sufficient for the convertase to alter proteolytic processing of the MSV propeptide into an active MSV peptide, and thereby modulating MSV activity.

The contacting step can further comprise contacting the MSV propeptide with an agonist or antagonist of the convertase, such as a furin endoprotease.

The present invention also provides for a method for treating a disease associated with muscle tissue, comprising administering a propeptide convertase to a subject having a disease associated with muscle tissue, said subject comprising a MSV propeptide, under conditions and for a time sufficient for the convertase to alter proteolytic processing of the MSV propeptide into an active MSV peptide, and thereby treating the disease.

The administering step can further comprise contacting the MSV propeptide with an agonist or antagonist of the convertase, such as furin endoprotease.

The method can be for the treatment of a disease associated with muscle atrophy, and can be selected from any one muscular dystrophy, muscle cachexia, atrophy, hypertrophy, disease-associated muscle atrophy and amyotrophic lateral sclerosis (ALS). The method can also be for the treatment of a disease-associated muscle atrophy comprising muscle wasting associated with cancer or HIV/AIDS.

The method can also be for the treatment of a disease associated with cardiac muscle, including infarct.

The present invention also provides for a method of regulating muscle growth of an animal comprising administering to said animal any one of: a composition according to the present invention; a modulator of MSV gene expression according to the present invention; a propeptide convertase or a agonist or antagonist of a propeptide convertase, such as a furin endoprotease.

The method may also be used to produce an animal having an increased muscle mass.

The present invention also provides for a method of predicting muscle mass in an animal, comprising the steps of:
i) obtaining a sample from the animal,
ii) determining a gene expression level from a polynucleotide having a sequence of any one of SEQ ID NOS: 1 to 47 or 96, a polynucleotide having 95%, 90%, 80% or 70% identity to SEQ ID NOS: 1 to 47 or 96, or a fragment or variant thereof,
iii) comparing the gene expression level to an average; and
iv) predicting the muscle mass of said animal.

The level of gene expression can be determined by a method comprising nucleic acid hybridization under stringent conditions to the polynucleotide, including RT-PCR or northern analysis.

The present invention also provides for a method of predicting muscle mass in an animal, including the steps of:
i) obtaining a sample from the animal,
ii) determining an amount of a polypeptide having a sequence of any one of SEQ ID NOS: 48 to 95, a polypeptide having 95%, 90%, 80% or 70% identity to any one of SEQ ID NOS: 48 to 95, or a fragment or variant thereof,
iii) comparing amount of polypeptide to an average; and
iv) predicting the muscle mass of said animal.

The amount of polypeptide can be determined by a method comprising detection of the polypeptide with an antibody that specifically binds to said polypeptide, including ELISA or western blot analysis.

The present invention also provides for a method of increasing the muscle mass of one or more offspring of an animal comprising the steps of:
i) selecting one or more animals predicted to have an increase in muscle mass by the method above, and
ii) breeding the one or more animals selected to have an increased muscle mass to produce one or more offspring having increased muscle mass.

The method can be preformed on an selected from a sheep, cattle, deer, poultry, turkey, pig, horse, mouse, rat or human.

The present invention also provides for a protein that preferentially binds a polypeptide having
(a) a sequence of any one of SEQ ID NOS: 48 to 95, or
(b) a sequence having 95%, 90%, 80% or 70% sequence identity to any one of SEQ ID NOS: 48 to 95.

The protein according can be selected from any one of an antibody; a non-mammalian antibody; bacterial immunity proteins, or any other class of binding protein known in the art, or a fragment or derivative derived from any such protein that is able to bind polypeptide having a sequence of any one of SEQ ID NOS: 48 to 95 or a polypeptide having 95%, 90%, 80% or 70% sequence identity to any one of SEQ ID NOS: 48 to 95. The non-mammalian antibody can be a IgNAR class of antibodies from sharks. The bacterial immunity proteins can be a IMM7 immunity protein from *E. coli*.

BRIEF DESCRIPTION OF THE FIGURES

The invention will now be further described with reference to the following figures.

DETAILED DESCRIPTION

Figure 1:
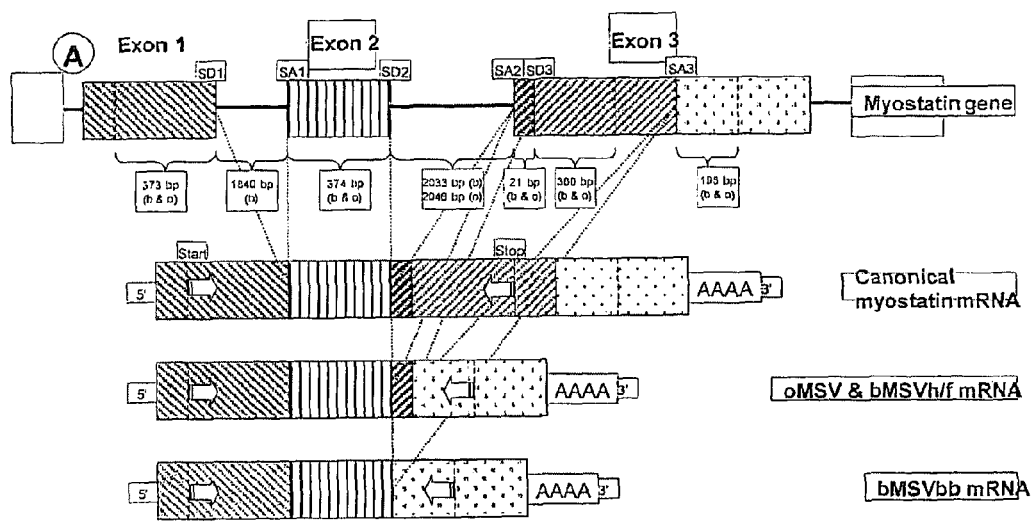
FIG. 1: shows a schematic representation of the myostatin gene and the RNA splicing giving rise to the canonical mRNA and the variant mRNAs (oMSV, bMSVh/f and bMSVbb).

The present invention relates in certain embodiments to the surprising discovery of a functional and biologically active myostatin variant mRNA molecule, which is the unexpected product of alternative splicing in the course of myostatin gene expression. As described in greater detail below, flanking PCR primers specific for nucleotide sequences in and adjacent to a myostatin-encoding open reading frame (ORF) were used in a reverse transcription-polymerase chain reaction (RT-PCR). Using this strategy in concert with subsequent cloning and sequencing of reaction products so obtained, a novel and unanticipated ovine myostatin splice variant (oMSV) was identified, having an ORF of 966 nucleotides (SEQ ID NO:1) that encoded a 321 amino acid polypeptide (SEQ ID NO: 48). The new 966 nt myostatin splice variant ORF was readily distinguishable from a previously identified ovine myostatin ORF (1128 nucleotides). Based on the DNA sequence information and cloning strategy described herein to identify for the first time oMSV, a surprising new bovine myostatin splice variant ortholog was also identified from skeletal muscle of Hereford/Friesian cross animals (bMSVh/f, SEQ ID NO: 5 & 52). As also described below, other myostatin splice variant orthologs from a number of additional mammalian species were subsequently identified through determination of alternative splice sites in myostatin gene sequences as disclosed herein.

The term "polynucleotide" is to be understood as meaning a polymer of deoxyribonucleic acids or ribonucleic acids, and includes both single stranded and double stranded polymers, including DNA, RNA, cDNA, genomic DNA, recombinant DNA, nucleic acid molecules prepared from natural or artificial nucleosides or nucleotides, and all other known forms of polynucleotides. The polynucleotide may be isolated from a naturally occurring source, produced using recombinant or molecular biological techniques, or produced synthetically. A polynucleotide may include a whole gene or any part thereof, and does not have to include an open reading frame.

The compliments and Reverse Compliments are also included in the present invention for a sequence 5'-CGTATT-3', these would be as follows:

Compliment: 3'GCATAA-5'

Reverse Compliment: 3'AAATACG-5'

The use of all polynucleotides according to the present invention includes any and all open reading frames. Open reading frames can be established using known techniques in the art. These techniques include the analysis of polynucleotide sequences to identify known start and stop codons. Many computer software programmes that can perform this function are known in the art.

A "polypeptide" is to be understood as meaning a polymer of naturally occurring and/or artificial amino acids covalently linked via peptide bonds. A polypeptide includes a polypeptide that has been isolated from a naturally occurring source, a polypeptide that has been produced using recombinant techniques, or a polypeptide that has been produced synthetically. It is to be appreciated that a polypeptide that includes a leader or pro-sequence, or a polypeptide that undergoes a post translational modification is intended to come within the definition of a polypeptide.

The term "fragment or variant" is to be understood to mean any polynucleotide or polypeptide sequence or partial sequence that has been modified by substitution, insertion or deletion of one or more nucleotides or one or more amino acids, but that has substantially the same activity or function as the unmodified sequence or partial sequence. Polynucleotide or polypeptide variants have at least 70% similarity (preferably a 70% sequence identity), 80% similarity (preferably a 80% sequence identity), 85% similarity (preferably a 85% sequence identity), and more preferably 90% similarity (more preferably a 90% sequence identity) to the reported polynucleotides or polypeptides, more preferably 95% similarity (more preferably a 95% sequence identity), and still more preferably a 98% similarity (still more preferably a 98% sequence identity) to the reported polynucleotides or polypeptides. As known in the art "similarity" between two such biopolymers, for example between two polypeptides, is determined by comparing the amino acid sequence and conserved amino acid substitutes thereto of the polypeptide to the sequence of a second polypeptide. Fragments or portions of the nucleic acid molecules encoding polypeptides of the present invention may be used to synthesize full-length polynucleotides. As used herein, "% identity" refers to the percentage of identical amino acids situated at corresponding amino acid residue positions in a sequence when two or more polypeptide are aligned and their sequences analyzed using a gapped BLAST algorithm (e.g., Altschul et al., Nucleic Acids Res. 25:3389 (1997)), which weights sequence gaps and sequence mismatches according to the default weightings provided by the National Institutes of Health/NCBI database (Bethesda, Md.; available on the internet at ncbi.nim.nih.gov/cgi-bin/BLAST/nph-newblast).

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, and valine; glycine, and alanine; asparagine and glutamine; and serine, threonine, phenylalanine, and tyrosine. Other groups of amino acids that may represent conservative changes include (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Amino acids may be classified according to the nature of their side groups. Amino acids with nonpolar alkyl side groups include glycine, alanine, valine, leucine, and isoleucine. Serine and threonine have hydroxyl groups on their side chains, and because hydroxyl groups are polar and capable of hydrogen bonding, these amino acids are hydrophilic. Sulfur groups may be found in methionine and cysteine. Carboxylic acid groups are part of the side chain of aspartic acid and glutamic acid, which because of the acidity of the carboxylic acid group, the amino acids are not only polar but can become negatively charged in solution. Glutamine and asparagine are similar to glutamic acid and aspartic acid except the side chains contain amide groups. Lysine, arginine, and histidine have one or more amino groups in their side chains, which can accept protons, and thus these amino acids act as bases. Aromatic groups may be found on the side chains of phenylalanine, tyrosine, and tryptophan. Tyrosine is polar because of its hydroxyl group, but tryptophan and phenylalanine are non-polar. A variant may also, or alternatively, contain nonconservative changes.

A MSV variant with at least one substitution, addition, insertion, or deletion may be made according to mutagenesis methods described herein and known in the art. Such modifications in a polynucleotide sequence that encodes a MSV variant or derivative may be introduced using standard mutagenesis techniques, such as oligonucleotide-directed site-specific mutagenesis. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, as described herein in detail and known in the art, oligonucleotide-directed site-specific mutagenesis procedures can be employed to provide an altered encoding polynucleotide wherein predetermined codons can be altered by substitution, deletion, or insertion. A MSV polypeptide for use in the present invention may be a portion or fragment of a full-length MSV polypeptide or a truncated MSV polypeptide as described herein. A truncated MSV polypeptide as described in greater detail herein may be any MSV polypeptide molecule that comprises less than a full-length version of the MSV polypeptide. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. A portion or fragment or a truncated form of a MSV polypeptide may have any number of amino acids fewer than about 320, 300, 275, 250, 225, 200, 175, 170, 160, 155, 150, 149, 148, 147, 146, 145, 144, 143, 142, 141, 140, 139, 138, 137, 135, 130, 125, 120, 115, 100, 95, 90, 85, 80, 75, 70, 65, 60, 65, 50, 45, 40, 35, 35, 25, 20, or 15 amino acids.

It should also be appreciated that software is available to very accurately predict the three dimensional structure of a peptide sequence (Bradely 2005). Therefore, it will be possible for someone skilled in the art to use such software to predict the effect of variations to the peptide sequence on structure of the peptide and therefore any likely effect on the activity of the peptide. Such variations are also incorporated within the scope of the present invention.

A polynucleotide fragment also includes a polynucleotide fragment of sufficient length and specificity to hybridise under stringent conditions to a sequence of any one of SEQ ID NOS: 1-7. An example of "stringent conditions" involves pre-hybridisation with 5×SSC, 0.2% SDS at 65° C.; performing the hybridisation overnight in 5×SSC, 0.2% SDS at 65° C.; two washes of 1×SSC, 0.1% SDS at 65° C. for 30 min each; followed by a further two washes of 0.2×SSC, 0.1% SDS at 65° C., also for 30 min each.

A polypeptide fragment also includes a fragment that retains the activity of promoting muscle growth. This fragment may have altered activity, i.e., activity that is increased or decreased in a statistically significant manner relative to an appropriate control polypeptide (e.g., a full length polypeptide), for example, enhanced activity such that the fragment, when introduced or expressed in a cell, results in an increased (e.g., with statistical significance) ability to promote muscle growth. Alternatively, the fragment may have altered activity that is manifest as a statistically significant decrease in function, for instance, a dominant negative effect. To determine whether a peptide according to the present invention is able to promote muscle growth can be tested by growing myoblasts in the presence of a absence of the peptide as described herein. An increase in growth of the myoblasts indicates that the peptide has muscle growth promoting activity. A suitable cell line could be movine $C_2C_{12}$ myoblasts (ATCC NO: CRL-1772), however, it will be appreciated that any suitable myoblast call line could be used, such as primary ovine or human myoblasts as described herein.

The term "isolated" as used herein refers to removal of a molecule such as a MSV polypeptide or encoding polynucleotide from its natural source, environment or milieu (e.g., removal of a protein from an intact cell source), and the term "purified" as used herein means that the MSV polypeptide or encoding polynucleotide is essentially free of association with other polynucleotides, proteins or polypeptides, for example, as a purification product of recombinant host cell culture, or as a purified product from a non-recombinant source. An "isolated" polypeptide therefore is one that is removed from its original environment. Preferably, such polypeptides are at least about 70%, 75%, 80%, 85% or 90% pure, at least about 95% pure, or at least about 99% pure, for example, where such a degree of purity refers to the percentage of detectable MSV polypeptide or encoding polynucleotide that is present in a preparation relative to other detectable polynucleotides and/or polypeptides. The term "substantially purified" or "substantially isolated" as used herein means a mixture that contains a molecule such as a MSV polypeptide or encoding polynucleotide that is essentially free of association with other polynucleotides, proteins or polypeptides, but for the presence of known proteins that can be removed using conventional methods, such as by affinity chromatography with a specific antibody or ligand, and which substantially purified or substantially isolated MSV polypeptide or encoding polynucleotide retains its biochemical characteristics as described herein or retains at least one of its detectable functional biological activities.

"Gene expression" is to be understood as meaning the initiation of transcription, the transcription of a section of DNA into mRNA, and the translation of the mRNA into a polypeptide. "A modulator of gene expression" is defined as any compound that is able to cause, in a statistically significant fashion, an increase or decrease in gene expression, and may act at any point in the gene expression pathway.

"Muscle growth" is to be understood as meaning the division and/or differentiation of muscle cells and includes the division and/or differentiation of any precursor cell, fusion of such cells with each other and/or with existing muscle fibres, and it also includes increased protein synthesis in myofibers leading to higher protein content and greater muscle fibre volume (muscle fibre hypertrophy).

"A modulator of protein activity" is to be understood as meaning an agent, compound or composition that is able to increase or decrease protein activity or function (e.g., a myostatin biological activity) in a statistically significant fashion.

The presently disclosed myostatin splice variant (MSV) is believed to be the result of an alternative splicing event. As shown in FIG. 1, the precursor canonical myostatin mRNA may be transcribed so as to include polynucleotide sequences of all three exons of the myostatin gene. The three exons are bounded by splice donor and acceptor sites, SD1 and SA1, and SD2 and SA2 respectively. Removal of the two introns, one between SD1 and SA1, and the other between SD2 and SA2, produces the canonical myostatin mRNA. The translation start site is located in exon 1, and the stop codon is located about one third of the way into exon 3, meaning that normally there is a large 3' untranslated region within exon 3.

As disclosed herein for the first time, an alternative splicing event may also take place in the course of myostatin gene expression by a process in which an extra splicing event occurs between SD3 and SA3 or between SD2 and SA3 (FIG. 1), causing the majority of the normally translated portion of the canonical exon 3 to be excised and replaced with the normally 3' untranslated section of exon 3. This unexpected splicing event creates a new open reading frame from which the MSV protein may be translated.

The resulting MSV polypeptide, ovine MSV (oMSV; SEQ ID NO: 48) and bovine MSV (bMSV; SEQ ID NO: 52) shares the first 257 amino acids with native myostatin propeptide, but has a unique 64 amino acid C-terminal end (ovine oMSV65, SEQ ID NO:49 and bovine bMSV, SEQ ID NO: 52). It is important to note that at the mRNA level, the 3' unique end of the MSV ORF differs by 195 nucleotides. The valine residue at position 257 in MSV protein is the same in the canonical myostatin sequence by pure coincidence because the splicing site exactly precedes the nucleotide triplet coding for a valine residue, which is part of the translated sequence of MSV. Therefore, the splice actually results in a 65 amino acid fragment, only 64 amino acids of which differ to the canonical myostatin sequence.

Based on the alternative splice sites identified, the MSV sequence for the following sequences has also been established: bovine (bt) (*Bos taurus*; b1(bt)MSV65, SEQ ID NO: 6 and 53; b2(bt)MSV65, SEQ ID NO: 9 and 56; b3(bt) MSV65, SEQ ID NO: a2 and 59 and b4(bt) MSV65 SEQ ID NO: 15 and 62), bovine (bi) (*Bos indicus*, b(bi)MSV65, SEQ ID NO: 18 and 65), bovine (bg) (*Bos grunniens*, Yak, b(bg) MSV65, SEQ ID NO: 21 and 68), porcine (*Sus scrofa*, pMSV68, SEQ ID NO: 24 and 71), human (*Homo sapiens*, h1MSV38, SEQ ID NO: 27 and 74 and h2MSV38, SEQ ID NO:77), Chimp (*Pan troglodytes*, chMSV38, SEQ ID NO: 33 and 80), dog (*Canis familiaris*, d1MSV36, SEQ ID NO: 36 and 83, d2MSV36, SEQ ID NO: 39 and 86, and d3MSV36, SEQ ID NO: 42 and 89), and cat (*Felis catus*, caMSV38, SEQ ID NO: 45 and 92).

Figure 15:
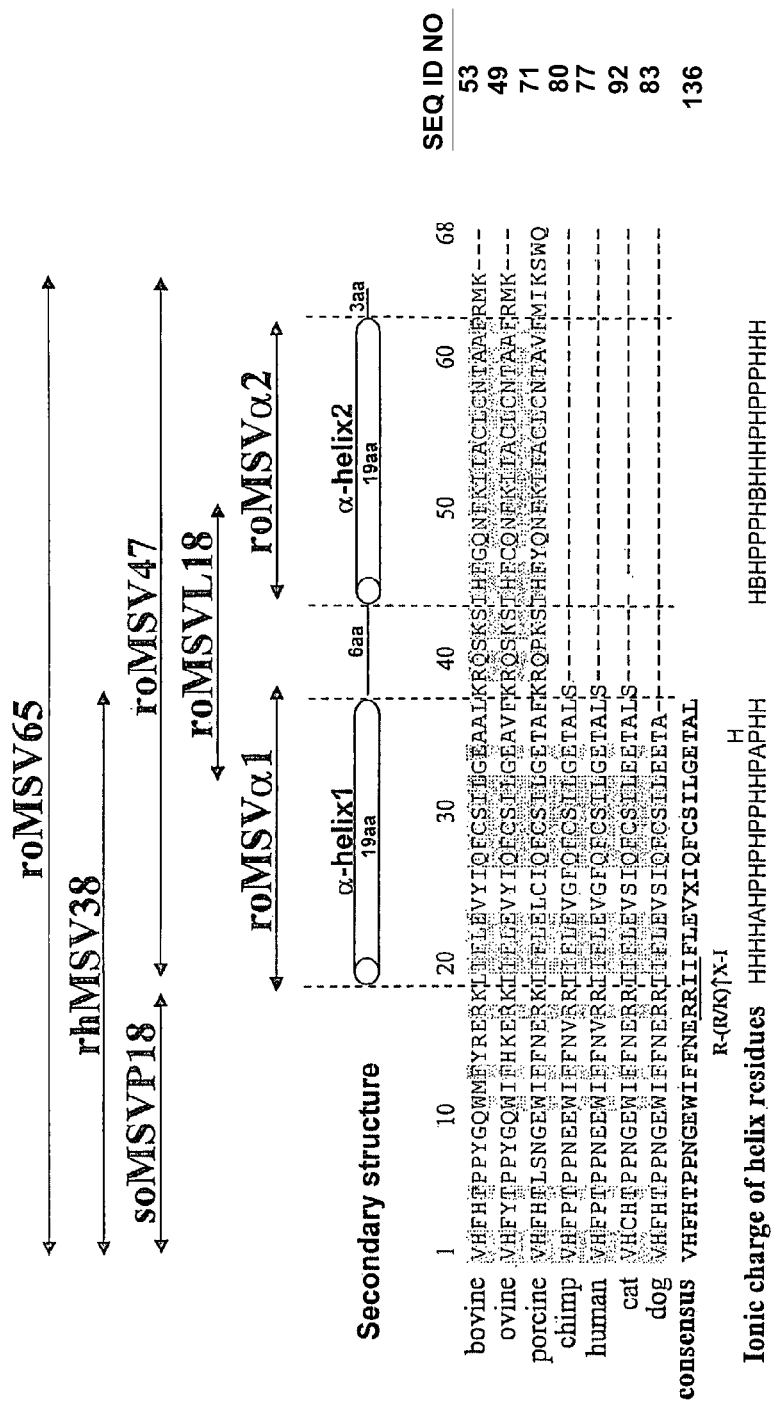
FIG. 15 shows the putative bioactive domains of MSV. In silico analysis (GCG software, Accelrys Inc., San Diego Calif. USA) predicted two alpha helices in bovine (*Bos taurus*), ovine and porcine MSV sequences. In contrast, the peptide sequence is terminated C-terminal to the first alpha helix in the remaining species shown. A putative proteolytic cleavage site (R—(R/K)↑X—I) is indicated below the consensus sequence that was consistent with a site recognised by the proprotein convertase SKI-1 which cleaves peptides C-terminal to the arrow (Seidah and Chretien 1999). The double-ended arrows and accompanying labels identify the peptides that were either synthesised or recombinantly expressed and tested as disclosed herein (s=synthesised, r=recombinantly expressed in *E. coli*, h=human, o=ovine, soMSVP18=preceding 18 amino acids to the putative cleavage site, roMSVL18=linker 18 amino acids that include the C-terminal six amino acids of the first helix through to and including the first N-terminal six amino acids in the second alpha helix). The ionic charge of the amino acids in the helices shows that the α-helix1 has a consistent pattern for all sequences listed and where amino acids differ, they have the same charge. The exception was ovine and bovine MSV which had a hydrophobic (A), rather than a polar (T) residue at residue 17 of α-helix1 (FIG. 15, position 35). A consistent pattern of ionic charge was also apparent for α-helix2. (the α-helix1 has no basic residues, and the α-helix2 has no acidic residues (H=hydrophobic, P=polar, A=acidic, B=basic).

A comparison of the sequences identified is shown in FIG. 15. It should be noted that the porcine sequence (pMSV68, SEQ ID NO: 71) has an extra three amino acid residues, totaling 68. Furthermore, human, chimp, and cat are all truncated, and provide for only 38 amino acid residues. The sequence for the dog is even shorter, being only 36 amino acids long.

Analysis of the various sequences has also identified a number of polymorphisms. Two human variations, have been identified, h1MSV38 (SEQ ID NO: 74), which has a glycine residue at position 1, and h2MSV38 (SEQ ID NO: 77) which has valine residue at position 1. Three polymorphisms have been identified in dog; d1MSV36 (SEQ ID NO: 83) which has an isoleucine residue at position 26, and a phenylalanine at position 28, d2MSV36 (SEQ ID NO: 86) which has phenylalanine residue at position 26 instead of the isoleucine, and d3MSV36 (SEQ ID NO: 89) which has a leucine at position 28 instead of the phenylalanine.

Four separate polymorphisms have also been identified in bovine (*Bos taurus*) b1(bt)MSV65 (SEQ ID NO: 53) has a phenylalanine at position 21, a glutamic acid at position 34 and glutamine at position 48; b2(bt)MSV65 (SEQ ID NO: 56) has a leucine at position 21, a valine at position 34 and a glutamine at position 48; b3(bt)MSV65 (SEQ ID NO: 59) has a leucine at position 21, a glutamic acid at position 34 and a glutamine at position 48; and b4(bt)MSV65 (SEQ ID NO: 62) has a phenylalanine at position 21, a glutamic acid at position 34 and a serine at position 48.

The invention therefore includes the MSV polynucleotide and polypeptide sequences (including polymorphisus) for bovine, ovine, porcine, human, chimp, dog and cat as set out below:

| MSV | DNA SEQUENCE | PROTEIN SEQUENCE |
|---|---|---|
| oMSV | SEQ ID NO. 1 | SEQ ID NO. 48 |
| oMSV65 | SEQ ID NO. 2 | SEQ ID NO. 49 |
| oMSV47 | SEQ ID NO. 3 | SEQ ID NO. 50 |
| oMSVα1 | SEQ ID NO. 4 | SEQ ID NO. 51 |
| bMSV | SEQ ID NO. 5 | SEQ ID NO. 52 |
| b1(bt)MSV65 | SEQ ID NO. 6 | SEQ ID NO. 53 |
| b1(bt)MSV47 | SEQ ID NO. 7 | SEQ ID NO. 54 |
| b1(bt)MSVα1 | SEQ ID NO. 8 | SEQ ID NO. 55 |
| b2(bt)MSV65 | SEQ ID NO. 9 | SEQ ID NO. 56 |
| b2(bt)MSV47 | SEQ ID NO. 10 | SEQ ID NO. 57 |
| b2(bt)MSVα1 | SEQ ID NO. 11 | SEQ ID NO. 58 |
| b3(bt)MSV65 | SEQ ID NO. 12 | SEQ ID NO. 59 |
| b3(bt)MSV47 | SEQ ID NO. 13 | SEQ ID NO. 60 |
| b3(bt)MSVα1 | SEQ ID NO. 14 | SEQ ID NO. 61 |
| b4(bt)MSV65 | SEQ ID NO. 15 | SEQ ID NO. 62 |
| b4(bt)MSV47 | SEQ ID NO. 16 | SEQ ID NO. 63 |
| b4(bt)MSVα1 | SEQ ID NO. 17 | SEQ ID NO. 64 |
| b(bi)MSV65 | SEQ ID NO. 18 | SEQ ID NO. 65 |
| b(bi)MSV47 | SEQ ID NO. 19 | SEQ ID NO. 66 |
| b(bi)MSVα1 | SEQ ID NO. 20 | SEQ ID NO. 67 |
| b(Yak,Bg)MSV65 | SEQ ID NO. 21 | SEQ ID NO. 68 |
| b(Yak,Bg)MSV47 | SEQ ID NO. 22 | SEQ ID NO. 69 |
| b(Yak,Bg)MSVα1 | SEQ ID NO. 23 | SEQ ID NO. 70 |
| pMSV68 | SEQ ID NO. 24 | SEQ ID NO. 71 |
| pMSV50 | SEQ ID NO. 25 | SEQ ID NO. 72 |
| pMSVα1 | SEQ ID NO. 26 | SEQ ID NO. 73 |
| h1MSV38 | SEQ ID NO. 27 | SEQ ID NO. 74 |
| h1MSV20 | SEQ ID NO. 28 | SEQ ID NO. 75 |
| h1MSVα1 | SEQ ID NO. 29 | SEQ ID NO. 76 |
| h2MSV38 | SEQ ID NO. 30 | SEQ ID NO. 77 |
| h2MSV20 | SEQ ID NO. 31 | SEQ ID NO. 78 |
| h2MSVα1 | SEQ ID NO. 32 | SEQ ID NO. 79 |
| chMSV38 | SEQ ID NO. 33 | SEQ ID NO. 80 |
| chMSV20 | SEQ ID NO. 34 | SEQ ID NO. 81 |
| chMSVα1 | SEQ ID NO. 35 | SEQ ID NO. 82 |
| d1MSV36 | SEQ ID NO. 36 | SEQ ID NO. 83 |
| d1MSV18 | SEQ ID NO. 37 | SEQ ID NO. 84 |
| d1MSVα1 | SEQ ID NO. 38 | SEQ ID NO. 85 |
| d2MSV36 | SEQ ID NO. 39 | SEQ ID NO. 86 |
| d2MSV18 | SEQ ID NO. 40 | SEQ ID NO. 87 |
| d2MSVα1 | SEQ ID NO. 41 | SEQ ID NO. 88 |
| d3MSV36 | SEQ ID NO. 42 | SEQ ID NO. 89 |
| d3MSV18 | SEQ ID NO. 43 | SEQ ID NO. 90 |
| d3MSVα1 | SEQ ID NO. 44 | SEQ ID NO. 91 |
| caMSV38 | SEQ ID NO. 45 | SEQ ID NO. 92 |
| caMSV20 | SEQ ID NO. 46 | SEQ ID NO. 93 |
| caMSVα1 | SEQ ID NO. 47 | SEQ ID NO. 94 |
| b(bb)MSV | SEQ ID NO. 96 | SEQ ID NO. 95 |

The polynucleotides of the present invention may be incorporated into vectors. Vectors are intended to include the incorporation of a sequence according to the present invention into a plasmid and/or virus to aid in the introduction and/or maintenance of the sequence in a host cell. Suitable vectors are known in the art and includes expression vectors. An expression vector includes a vector specifically for expressing the protein of interest in a particular host cell. Typically such vectors include a promoter sequence, the polynucleotide of interest and a gene termination in operable linkage, meaning that the promoter will effect gene expression of the polynucleotide of interest, while the gene termination will terminate transcription. Suitable promoters to effect gene expression are well known in the art and may include, but are not limited to, the myostatin promoter. The host cell may include, either, a prokaryotic or a eukaryotic cell. The eukaryotic cell may be in vivo, or may be a primary or transformed cell line.

Compositions based on the novel polynucleotide and/or polypeptides of the present invention are also contemplated. One or more compositions may be used to regulate myostatin or to regulate muscle growth. The regulation of muscle growth is intended to include any change in the rate of muscle growth and/or development and includes the growth and/or differentiation of any muscle precursor cell. This includes any change in the rate at which precursor muscle cells divide, and any change in the rate at which precursor muscle cells differentiate. The change may be either an increase or a decrease.

The composition may comprise a polynucleotide sequence according to the present invention, including any one of SEQ ID NOS: 1 to 47 or 96, a polynucleotide having 95%, 90%, 80% or 75% identity to any one of the polynucleotides, or a fragment or variant thereof. The sequence may be introduced into a cell by incorporation into a suitable vector under the regulation of a promoter, either the myostatin promoter or any other suitable promoter. The promoter may be used to cause expression of a MSV protein according to the present invention, thereby both increasing gene expression and MSV activity within the cell.

The composition may also include compliments, reverse compliments, or anti-sense polynucleotides of the polynucleotides according to the present invention.

The composition may also include a polypeptide sequence according to the present invention, including any one of SEQ ID NOS: 48 TO 95 or a polypeptide having 95%, 90%, 80% or 75% identity to any one of the polypeptides. The peptide can be directly incorporated into a composition suitable for administration to a subject. A suitable composition can include compositions for oral or topical administration, inhalation, administration by injection or any other suitable form.

Sequence identity may be determined by aligning the sequences and determining the number of identical residues. Many computer algorithms are known in the art for determining the sequence identity, for example BLASTN for determining the identity between polynucleotide sequences, and BLASTP for determining the identity between polypeptide sequences.

The composition may also include a modulator of MSV activity. This may comprise a modulator of MSV gene expression or a modulator of MSV protein activity.

The modulator of MSV expression may be a compound that can specifically bind to a polynucleotide according to the present invention and affect the rate of MSV gene expression. An alteration in gene expression can be determined by either an increase or decrease in MSV protein in a cell, or subject. Specifically, the modulator of MSV expression could bind to the MSV promoter, thereby affecting the rate at which gene transcription is initiated. Alternatively, the modulator of MSV gene expression may also bind to the MSV gene or MSV mRNA directly affecting the rate at which the gene is expressed. The modulator of MSV expression may also bind to the MSV gene and introduce alterations into the sequence, for example, by homologous recombination, which may either affect the rate at which the gene is expressed, or may alter the MSV protein activity. Alterations of a sequence include a nucleotide change, insertion or deletion, which may or may not result in an amino acid change, insertion or deletion in the resulting polypeptide. Examples of alterations can include the insertion of a termination codon, such that a truncated polypeptide is produced, or the alteration of one or more codons such that one or more amino acid residues are altered. Alternatively, the variations could be to delete a section of the wild-type MSV gene, or introduce a section into the MSV gene. Techniques are well known in the art to make such alterations. Furthermore, it would be within the scope of a person skilled in the art to introduce such changes into the MSV gene and then test the alterations on MSV activity, for example, using the myoblast proliferation assay as described in the examples.

Alternatively, the modulator of MSV expression may act by altering the RNA processing step. Thereby the modulator of RNA processing would alter the ratio of myostatin to MSV. Both a modulator of RNA transcription could be used in conjunction with a modulator of RNA processing to control both the rate at which the native RNA molecule is transcribed and the amount of resulting MSV. For example, using RNAi or siRNA technology the ratio of canonical myostatin and MSV can be altered. In doing so, for example, the inhibitory effect of myostatin on muscle growth can be reduced, and at the same time the MSV muscle growth enhancing effect can be increased. The effect of an interfering RNA molecule can be established by a reduction in the amount of the MSV peptide.

The MSV gene expression may also be altered by introducing polynucleotides that interfere with transcription and/or translation. For example, anti-sense polynucleotides could be introduced, which may include; an anti-sense expression vector, anti-sense oligodeoxyribonucleotides, anti-sense phosphorothioate oligodeoxyribonucleotides, anti-sense oligoribonucleotides, anti-sense phosphorothioate oligonucleotides, or any other means that is known in the art, which includes the use of chemical modifications to enhance the efficiency of anti-sense polynucleotides.

It will be appreciated that any anti-sense polynucleotide need not be 100% complementary to the polynucleotides in question, but only needs to have sufficient identity to allow the anti-sense polynucleotide to bind to the gene, or mRNA to disrupt gene expression, without substantially disrupting the expression of other genes. It will also be understood that polynucleotides that are complementary to the gene, including 5' untranslated regions may also be used to disrupt translation of the MSV protein. Likewise, these complementary polynucleotides need not have 100% complementary, but be sufficient to bind the mRNA and disrupt translation, without substantially disrupting the translation of other genes.

The modulation of gene expression may also comprise the use of an interfering RNA molecule as is known in the art, and includes RNA interference (RNAi) and small interfering RNA (siRNA).

Use of interfering RNA's are now well known in the art and suitable interfering RNA's could be designed and tested given the sequences disclosed in the present invention. Use of therapeutic RNA interference is known in the art (Uprichard 2005) as is the use of exon specific interference RNA to alter alternative splicing (Celolto 2002).

Modulation of gene expression may also be achieved by the use of catalytic RNA molecules or ribozymes. It is known in the art that such ribozymes can be designed to pair with a specifically targeted RNA molecule. The ribozymes bind to and cleave the targeted RNA.

Any other techniques known in the art of regulating gene expression and RNA processing can also be used to regulate MSV gene expression.

The composition may also include a modulator of MSV activity. A modulator of MSV activity in a composition that is able to increase or decrease the ability of MSV to promote muscle growth. A modulator of MSV may include a dominant negative mutant of the polypeptides according to the present invention. A dominant negative effect arises where a mutant acts to block the physiological activity of a wild type protein.

This may occur by the dominant negative protein binding to, but not activating, a receptor, while also preventing the wild type protein from binding. Alternatively the dominant negative may act by binding directly to, and inactivating, the wild type protein. Thus the polynucleotides of the present invention can be used to make suitable compositions, or be used to design suitable compositions that regulate MSV gene expression, and thereby regulate muscle growth. Such techniques could be used to regulate MSV gene expression within a cell, for example within a primary or transformed cell line, or to regulate muscle growth within an animal.

The modulator of MSV activity may also include a modulator of proteolytic processing of the propeptide. Such a modulator could include propeptide convertase, for example furin endopeptidase, or an agonist or antagonist of propeptide convertases.

One possible application of one or more compositions of the present invention is to promote or inhibit muscle cell growth and/or differentiation. The muscle cell can be either a primary or transformed cell line, or the cell can be an in vivo cell of a host animal. Suitable host animals may include sheep, cattle, deer, poultry, pigs, fish, horses, mice, rats or humans.

One or more compositions of the present invention may also be used for the treatment of diseases associated with muscle tissue. A disease associated with muscle tissue includes any disease or medical condition that involves a change in muscle tissue compared to normal muscle tissue. Such changes may indicate an increase or decrease in muscle mass, or an increase or decrease in muscle fibres. Such diseases may include muscular dystrophy, muscle cachexia, atrophy, hypertrophy and muscle wasting associated with diseases such as cancer or HIV, or amyotrophic lateral sclerosis (ALS). Diseases associated with cardiac muscle growth, including infarct are also contemplated. Suitable methods for diagnosing such diseases is well known in the art and can involve both physical examination of a subject or more detailed analysis of a muscle, or other body sample. Such diseases as listed above, or similar such diseases could be diagnosed by a suitable clinician.

The composition can be administered in any suitable form, which may include oral, topical, inhalation, injection or any other suitable form of administration as known in the art. The composition can be applied for a sufficient time and amount to effect an improvement in the condition.

Similarly one or more compositions could be used to produce transgenic animals. The compositions could be used to produce transgenic animals having an increase in muscle mass. Suitable animals may include sheep, cattle, deer, poultry, pigs, fish, horses, mice, rats or humans. Many techniques are known in the art for producing transgenic animals, and any suitable method could be used.

Another application of the present invention may be to predict the muscle mass of an animal. To do this a sample is obtained from an animal. Any body sample containing a representative amount of MSV will be suitable and can include a blood sample, a biopsy sample, or a sample of muscle tissue. The sample is then analysed for the level of MSV gene expression, or a MSV protein. Many techniques are known in the art for measuring gene expression or protein amount. For example, gene expression can be analysed using quantitative RT-PCR or northern analysis. Protein content can be determined using ELISA [Enzyme-linked Immunosorbant Assay] or Western blot analysis. Any suitable method can be used, for example as set out in any text, for example Maniatis (Molecular Cloning, 2$^{nd}$ edition, Cold spring Harbor Laboratory Press, 1989).

The level of MSV gene expression, or amount of the MSV protein, is then compared to an average. An average level of MSV gene expression is the average level obtained from a sample of animals of average muscle mass. Similarly, the average amount of MSV protein is the amount of protein observed in a sample of animals of average muscle mass.

An increased level of MSV gene expression or MSV protein, compared to the average, means that the muscle mass of the animal will be predicted to have an above average muscle mass. A decreased level of MSV gene expression or MSV protein, compared to the average, means that the muscle mass will be predicted to be less than average.

The method may be used to pick animals to be involved in a breeding programme to produce offspring with increased or decreased muscle mass.

The invention also provides for polypeptides that are able to preferentially bind any one of the polypeptides according to the present invention. Many such polypeptides are known in the art, which includes but is not limited to antibodies; a non-mammalian antibodies, for example the IgNAR class of antibodies from sharks; bacterial immunity proteins, for example a IMM7 immunity protein from *E. coli*, or any other class of binding protein known in the art. Given the sequences disclosed in the present specification, a person skilled in the art would be able to produce such a polypeptide or screen a library of known binding polypeptides to obtain a polypeptide that preferentially binds to a polypeptide of the present invention. Examples of how antibodies can be produced including the production of hybridoma cells can be found in Eryl Liddell and Cryer or Javois. It will be appreciated that a polypeptide includes a fragment from such a polypeptide that that confers the preferential binding activity, for example, the variable domain of an antibody.

Experimental:

To explore the biological function of the novel C-terminal sequence of ovine MSV, the 65 amino acid peptide (SEQ ID NO: 49) was expressed as a recombinant protein in *E. coli* (called recombinant ovine myostatin splice variant 65, (roMSV65) and its function was tested in a muscle cell culture system.

Figure 2:
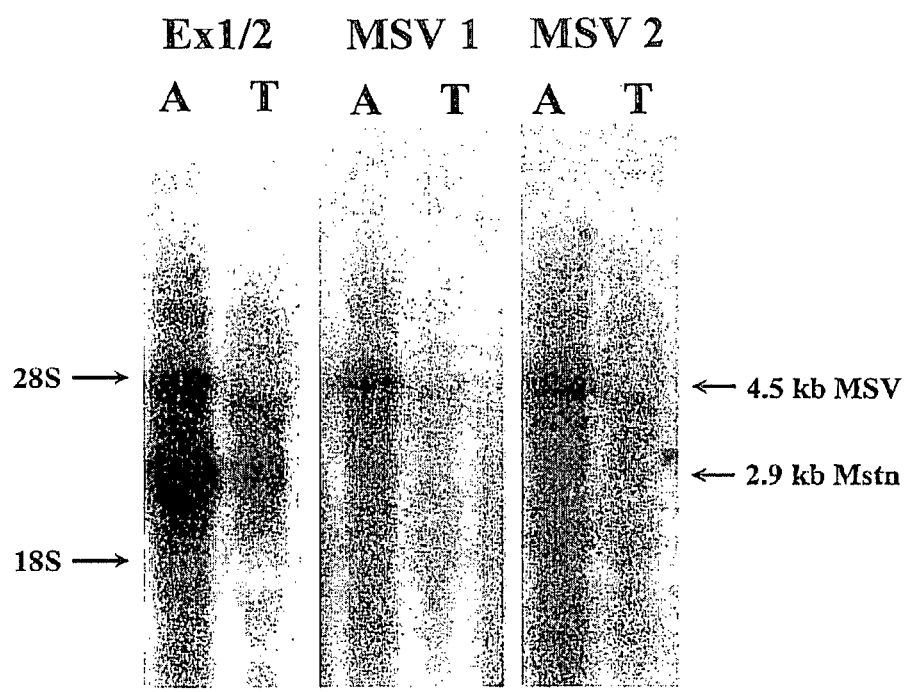
FIG. 2 shows northern blots detecting the presence of canonical ovine myostatin (Mstn) and MSV mRNAs using a probe extending across the boundary of Exons 1 and 2 (Ex1/2), and probes complementary to the 3'-UTR of ovine myostatin gene beyond the polyadenylation sites of canonical myostatin (designated MSV 1 and MSV 2). These data show that two mRNA species were detected when a probe sequence was used that was common to both mRNA species. However, only a single mRNA species was present when probes specific for a region distal to the 3'-UTR of the polyadenylation sites of canonical myostatin, but within the longer 3'-UTR of MSV were used (A=polyadenylated RNA, T=total RNA). These data suggest that the ovine MSV protein is encoded by a 4.5 kb mRNA molecule.

Northern blot analysis was preformed to identify MSV mRNA species in total or poly(A)+ RNA isolated from tissue. Because ovine MSV was first identified in sheep skeletal muscle via RT-PCR, total RNA was isolated from *M. semitendinosus* for Northern analysis and subsequently poly(A)+ RNA was purified to eliminate ribosomal RNA associated non-specific binding of radio-labelled DNA probes and to enrich mRNA content. First, a probe complementary to Exon1/2 was used. As shown in FIG. 2 this Ex1/2 probe detected two bands corresponding to canonical myostatin mRNA at 2.9 kb and larger, 4.5 kb mRNA species, which identifies MSV. This is consistent with the expected two positive hybridisation signals because canonical myostatin and MSV mRNA share the same exon1 and 2 sequences. To identify MSV mRNA separately from canonical myostatin, two probes were employed homologous to 3'UTR sequences downstream of polyadenylation sites of canonical myostatin. These probes should not hybridise to canonical myostatin mRNA (2.9 kb) because it is terminated at close proximity to the polyadenylation signals. As expected a single hybridisation signal was detected with both probes at the same 4.5 kb size, suggesting that it corresponds to the MSV mRNA (MSV1 and 2, FIG. 2). This Northern blot analysis confirmed the existence of two mRNA species transcribed from the ovine myostatin gene in sheep muscle. The smaller 2.9 kb mRNA species corresponds to canonical myostatin, while the larger 4.5 kb mRNA species identifies MSV.

Figure 3:
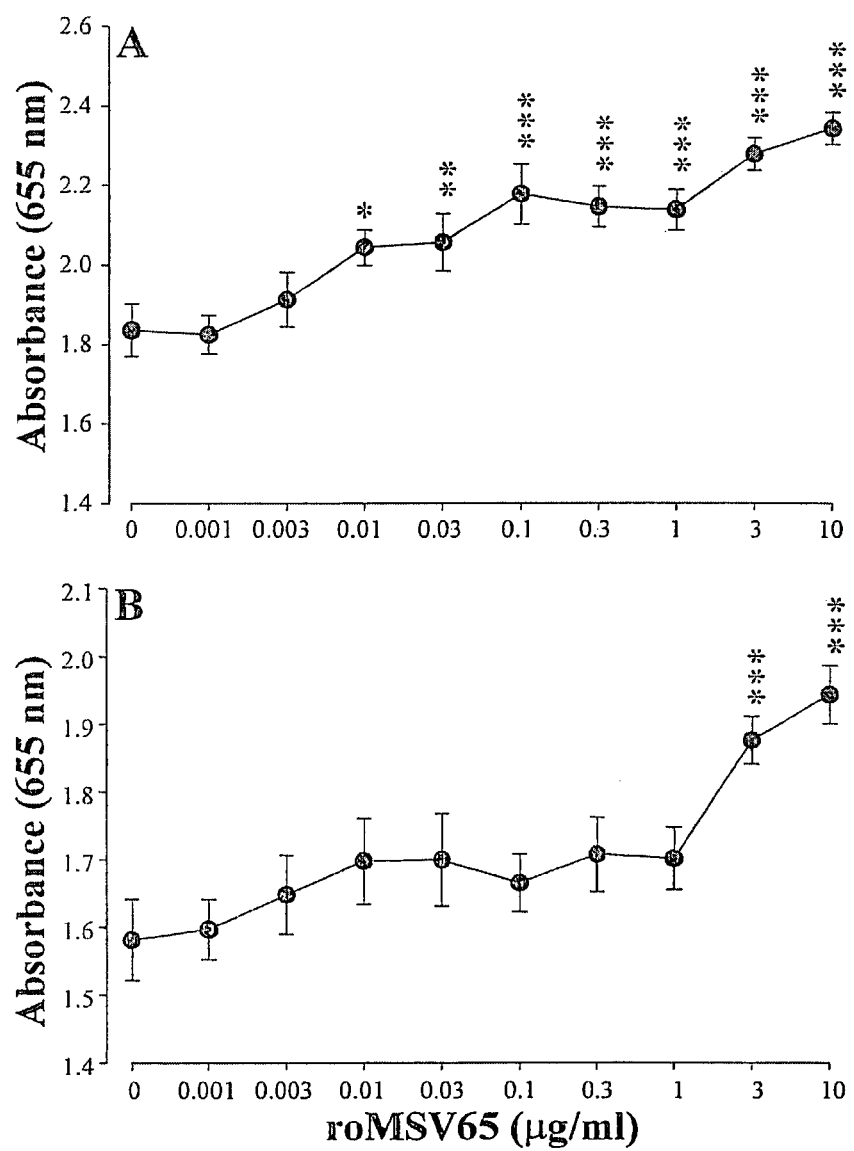
FIGS. 3A & B: show the effect of recombinant ovine MSV65 protein on the proliferation of murine $C_2C_{12}$ (3A) and ovine primary myoblasts (3B). Myoblasts were grown in the presence of increasing concentrations of roMSV65 (0 to 10 µg/ml) for 72 h. Cell proliferation was determined by methylene blue assay (optical density at 655 nm). Values are mean±SEM ($*p<0.05$, $p<0.01$, $*p<0.001$).

As shown in FIG. 3, the 65 amino acid peptide (roMSV65; SEQ ID NO: 49) when added to $C_2C_{12}$ myoblasts (FIG. 3a) and primary ovine myoblasts (FIG. 3B), is able to stimulate myoblast cell growth in a dose dependent manner. This confirms that MSV is acting as a promoter of muscle cell growth, or an antagonist to myostatin.

Figure 4:
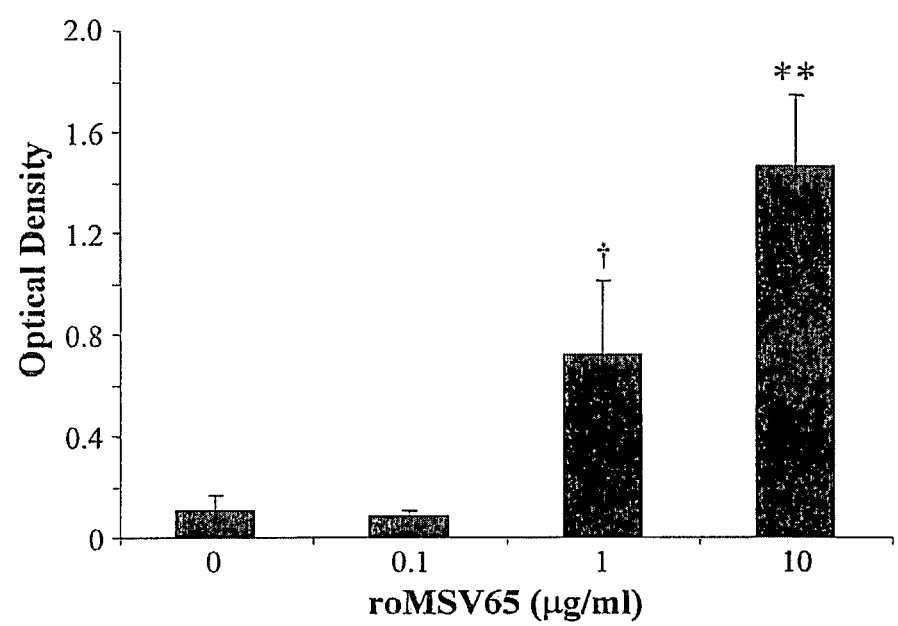
FIG. 4: shows the effect of recombinant ovine MSV65 protein on the amount (Mean±SEM) of myogenin protein in differentiated $C_2C_{12}$ myotubes. Myoblasts differentiated in the presence of increasing concentrations of MSV65 (0, 0.1, 1, 10 µg/ml, n=3) or its absence (control, n=3) for 72 h. Total protein was extracted from the cells and the abundance of myogenin was determined by Western blot analysis ($†p<0.1$, $**p<0.01$).

To investigate whether the MSV peptide was also stimulating muscle development, $C_2C_{12}$ myoblasts were treated with roMSV65 during the course of differentiation, and then the levels of myogenin and myosin heavy chain protein, molecular markers of early and late myoblast differentiation were measured by Western immunoblotting. Interestingly, it was found that roMSV65 dose-dependently increases myogenin protein levels in $C_2C_{12}$ myotubes (FIG. 4). This shows that roMSV65 also induces myoblast differentiation by up-regulating myogenin, a basic helix-loop-helix transcription factor, responsible for the induction of muscle specific genes involved in the terminal differentiation program (Montarras et al. 1991). Myostatin inhibits myoblast differentiation by down-regulating myogenin, MyoD and p21 through a Smad 3 mediated mechanism (McCroskery et al. 2003, Joulia et al. 2003, Langley et al. 2002). Here, it has been shown that MSV65 counteracts myostatin by oppositely regulating myogenin levels in $C_2C_{12}$ myotubes.

Figure 5:
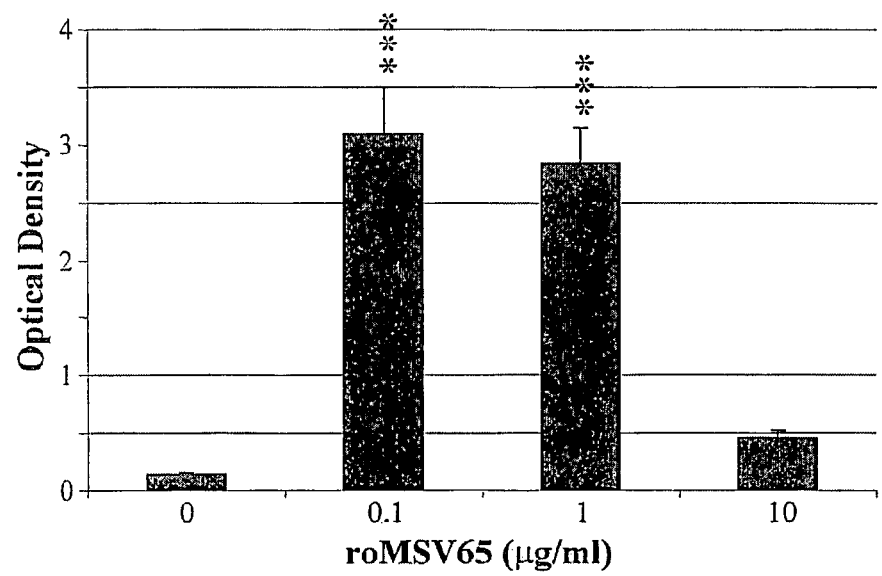
FIG. 5: shows the effect of recombinant ovine MSV65 on the amount of developmental myosin heavy chain (dMHC) protein expression in $C_2C_{12}$ myotubes. Myoblasts were treated with roMSV65 at 0, 0.1, 1 and 10 µg/ml (n=3) for 72 h in differentiation medium, and dMHC protein levels were detected in the total protein extracted from muscle cells using Western blot analysis. Values are mean±SEM (***p<0.001).

Myosin heavy chain (MHC) proteins are essential structural components of sarcomeres, the contractile units of muscle fibers. These large proteins of 230 kDa are abundantly expressed in myotubes, formed by fusion of terminally differentiated mononucleated myoblasts, and in myofibers of the muscle tissue. As shown in FIG. 5 developmental myosin heavy chain (dMHC) protein expression is greatly up-regulated in response to roMSV treatment in $C_2C_{12}$ myotubes. Interestingly, there is a 18- to 20-fold increase in dMHC abundance at 0.1 and 1 µg/ml roMSV65 concentrations compared to untreated controls, respectively. However, at the highest dose of roMSV65 (10 µg/ml) only a 2-fold increase in dMHC abundance was detected. These data suggest that roMSV65 might be able to induce muscle fiber hypertrophy via the up-regulation of MHC protein synthesis. It is unclear why the extent of MHC up-regulation is not concentration dependent and the result at 10 µg/ml may just be an artifact. The molecular pathway responsible for the induction of MHC expression is yet to be identified. This confirms that MSV is not only able to stimulate myoblast division, but is also stimulating the cells to differentiate into muscle fibres.

During muscle development, myoblasts initially undergo cell division during myogenesis, before withdrawing from the cell cycle. On withdrawing from the cell cycle the myoblasts begin to differentiate into myotubes. Progression through, and arresting from, the cell cycle is controlled by cyclin-dependent kinase and cyclin-dependent kinase inhibitor (CDK/CKI) complexes. Myostatin has been shown to regulate myoblast transition from the G1 to S and G2 to M transitions through modulation of p21cip1 and Cdk2 protein levels. As well as down regulating expression of Cdk2, myostatin also upregulates the cyclin-dependent kinase inhibitor p21 thereby inactivating the cyclin/CDK complex, which stimulates progression from G1 to S phase (Thomas et al 2000).

Figure 6:
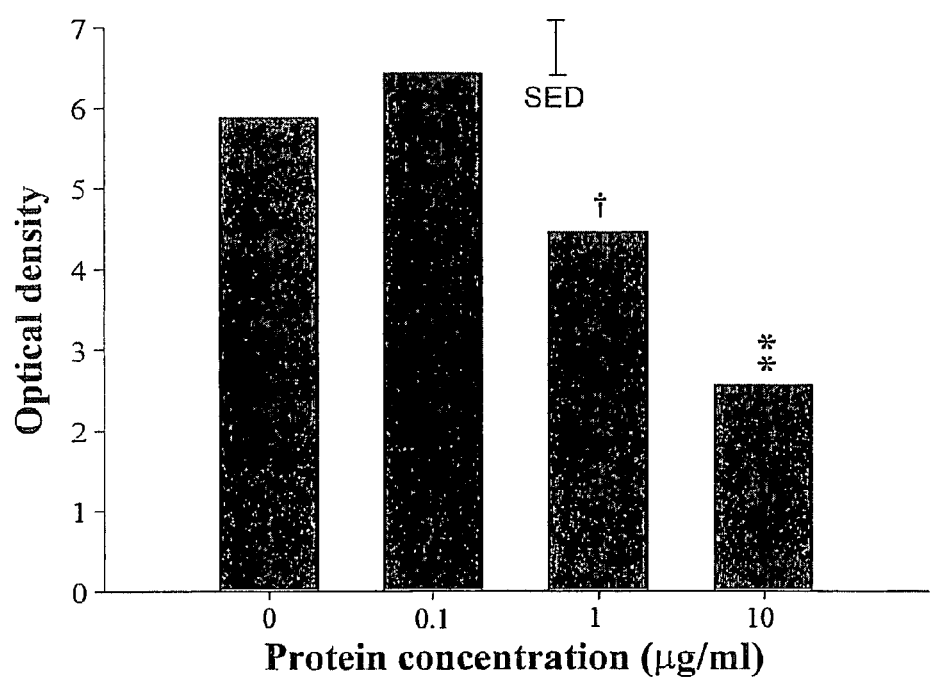
FIG. 6: shows the effect of recombinant ovine MSV65 on the amount (Mean±SEM) of p21 protein levels in proliferating $C_2C_{12}$ myoblasts. Myoblasts were grown in the presence of increasing concentrations of roMSV65 (0, 0.1, 1 and 10 µg/ml, n=3) or its absence (control, n=2) for 48 h. Total protein was extracted from the cells and p21 levels were determined by Western blot analysis (* p<0.05, ** p<0.01).

As shown in FIG. 6, western blot analysis revealed that roMSV65 dose-dependently decreases p21 protein levels in proliferating $C_2C_{12}$ myoblasts having the opposite effect on p21 expression as that of mature myostatin. Lower levels of p21 allow cell cycle progression from G1 to S and G2 to M phases promoting cell replication. This confirms that, mature myostatin and MSV regulate the same downstream target molecule p21 but in opposite ways. This finding is consistent with the hypothesis that MSV is a naturally occurring antagonist of myostatin bioactivity.

Figure 7:
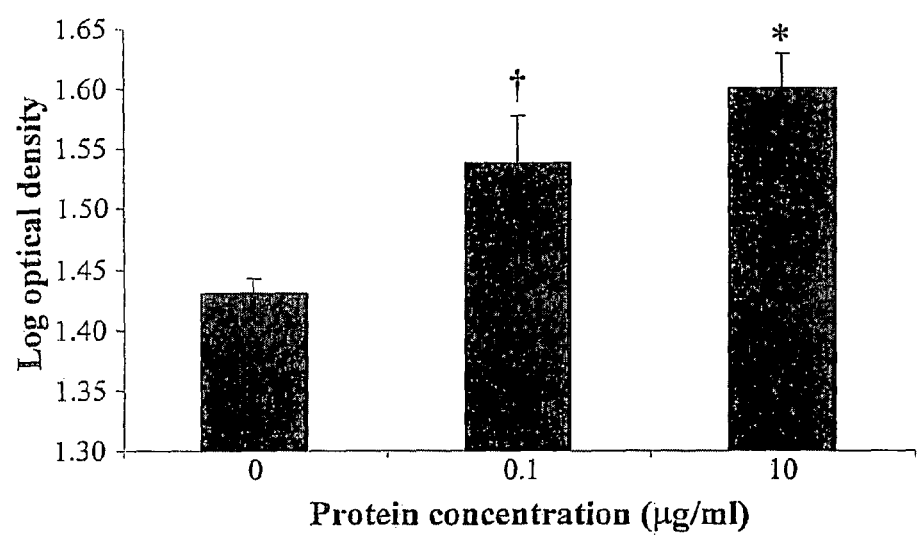
FIG. 7: shows the effect of recombinant ovine MSV65 on the amount (Mean±SEM) of proliferating cell nuclear antigen (PCNA) protein levels in proliferating $C_2C_{12}$ myoblasts. Myoblasts were grown in the presence of increasing concentrations of oMSV65 (0, 0.1, 1 and 10 µg/ml, n=3) or its absence (control, n=2) for 48 h. Total protein was extracted from the cells and PCNA levels were determined by Western blot analysis (†p<0.1, * p<0.05).

The mitogenic activity of roMSV65 was confirmed with proliferating cell nuclear antigen (PCNA), a positive molecular marker of cell proliferation. Higher level of PCNA protein expression is associated with higher number of cells entering the DNA replication phase of the cell cycle. As shown in FIG. 7, western immunoblotting of $C_2C_{12}$ myoblasts treated with roMSV65 showed a concentration-dependent increase in PCNA protein levels.

Figure 9:
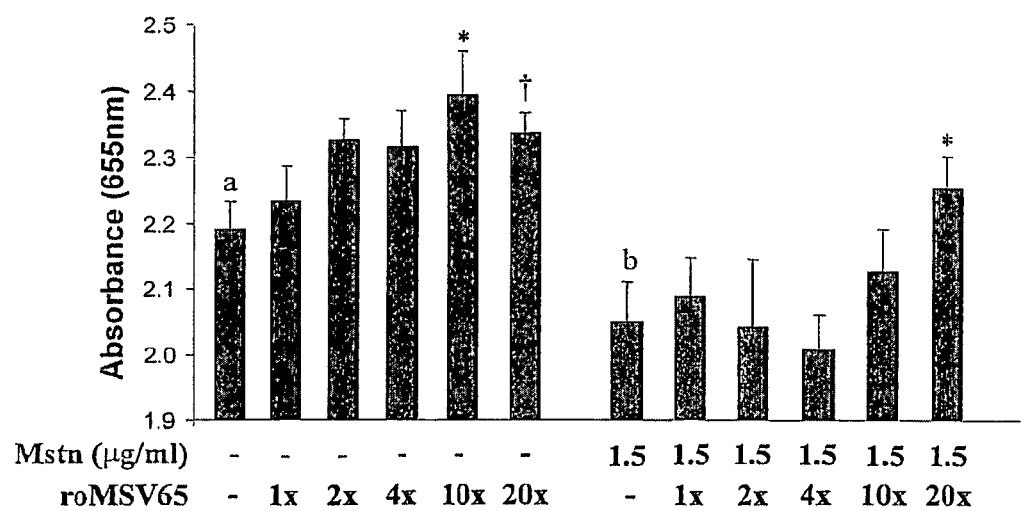
FIG. 9 shows mean (±SEM) proliferation of murine $C_2C_{12}$ myoblasts treated with and without myostatin (Mstn) and roMSV65 as indicated for 48 h. These data indicate that roMSV65 firstly, stimulated proliferation of murine myoblasts and, secondly overcame myostatin-induced inhibition of proliferation of primary human myoblasts and stimulated proliferation beyond restoration. Doses of roMSV65 are depicted in molar amounts (x) relative to the 1.5 µg/ml Mstn used in the second part of the assay. Unlike letters indicate significance (a,b P<0.1). Symbols and asterisks indicate significance relative to the first bar in each grouping (†P<0.1, *P<0.05, n=8).

To further confirm that MSV is able to regulate myostatin activity the ability of roMSV65 to out-compete myostatin in a $C_2C_{12}$ proliferation assay was tested. As shown in FIG. 9 roMSV65 was able to rescue myostatin inhibited myoblast proliferation at 1:20 (myostatin:roMSV65) molar ratio at 1.5 µg/ml myostatin concentration (FIG. 9). These data confirm that MSV65 is acting as an antagonist of mature myostatin.

These data confirm that MSV65 is able to promote muscle growth and differentiation, and is able to regulate or oppose the inhibitory effect of myostatin.

Proteolytic Processing of the MSV

Figure 8:
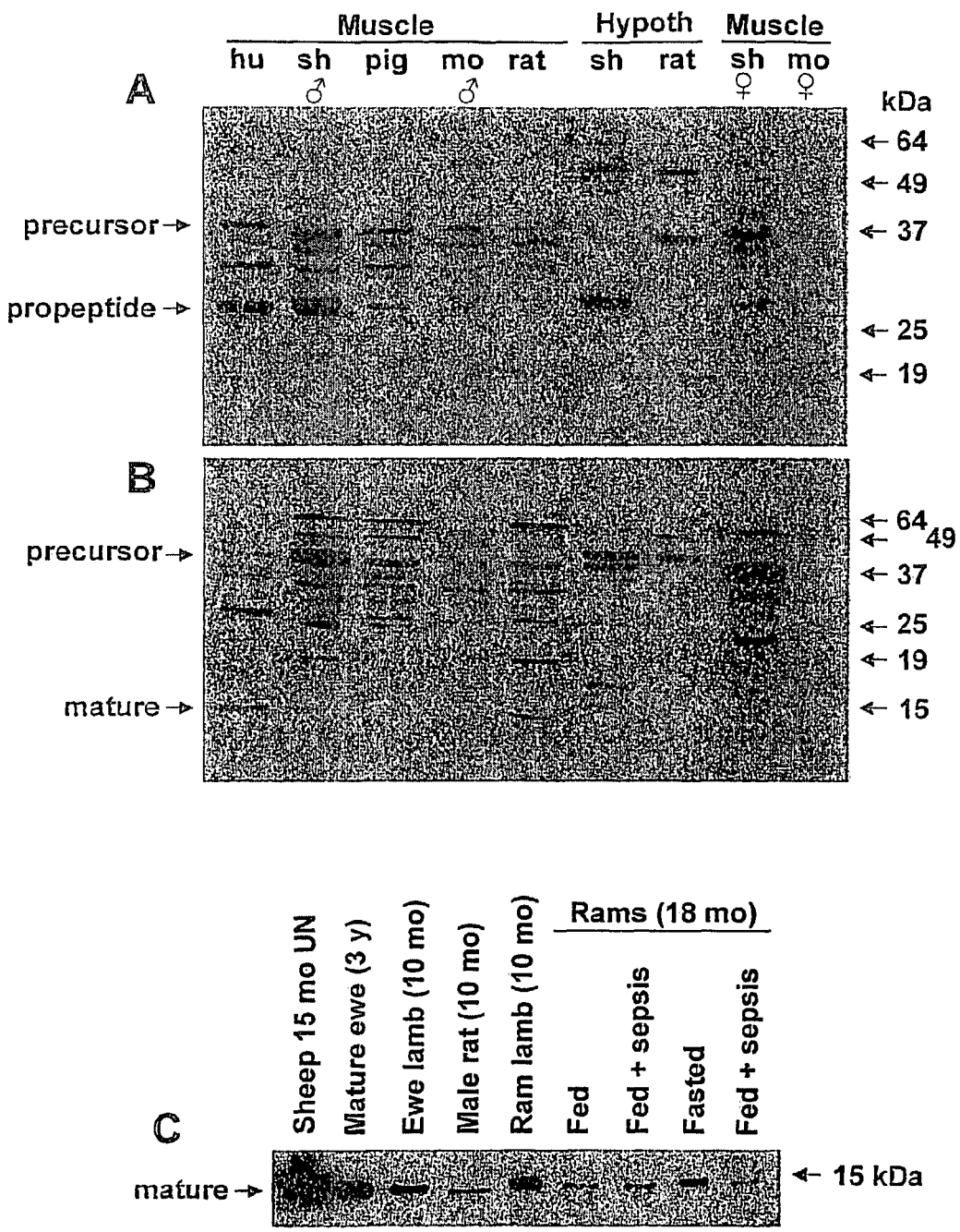
FIG. 8: shows the identification of MSV proteins in tissues of different species using Western immunoblots. Protein samples were separated by 10% (8A) or 15% (8B, C) SDS-PAGE and transferred to nitrocellulose membranes. Blots were probed with propeptide-specific (8A) or mature MSV-specific polyclonal antibodies (8B & C). Expected sizes of precursor (37 kDa), propeptide (29 kDa) and putative mature dimmer (11 kDa) MSV proteins in sheep are indicated by arrows. Abbreviations used: hypoth-hypothalamus, hu-human, sh-sheep, mo-mouse (8A, B), mo-month (8C), UN-undernourished, y-year, ♀-female, ♂-male.

The fragment excised from normal myostatin mRNA during alternative splicing includes the normal catalytic cleavage site at Arg 266. However, it has been determined that a potential (KERK/RXXR) cleavage site exists at position 271 to 274 by propeptide convertases (PC1-7) including furin endopeptidase (Steiner 1998). Furin proprotein convertases (PC) have to have a consensus motif $(K/R)$—$(X)_n$—$(K/R)\downarrow$, where n=0, 2, 4, or 6, and X is any amino acid, but usually not a Cys (Seidah 1999, Seidah 1997). More common to the TGF-β family is an R—X—K/R—R motif, where K and R are interchangeable, but an R—X—K/R—R sequence is optimal (Dubois 2001). Cleavage at position 274, would release a 47 amino acid C-terminal mature MSV fragment from ovine and bovine (ovine: oMSV47, SEQ ID NO: 50 and bovine: bMSV47, SEQ ID NO: 54). Cleavage of the porcine sequence result in the release of 50 amino acid fragments (pMSV50, SEQ ID NO: 72), a 20 amino fragment for human, chimp and cat ($h_{1-2}$MSV20, SEQ ID NOS: 75 and 78; chMSV20, SEQ ID NO: 81; and caMSV20, SEQ ID NO: 93), and a 18 amino acid peptide is released from the dog sequence ($d_{1-3}$MSV18, SEQ ID NOS: 84, 87 and 90). The existence of the mature C-terminal peptide was confirmed using an antibody against the MSV47 peptide (FIG. 8C).

Figure 10:
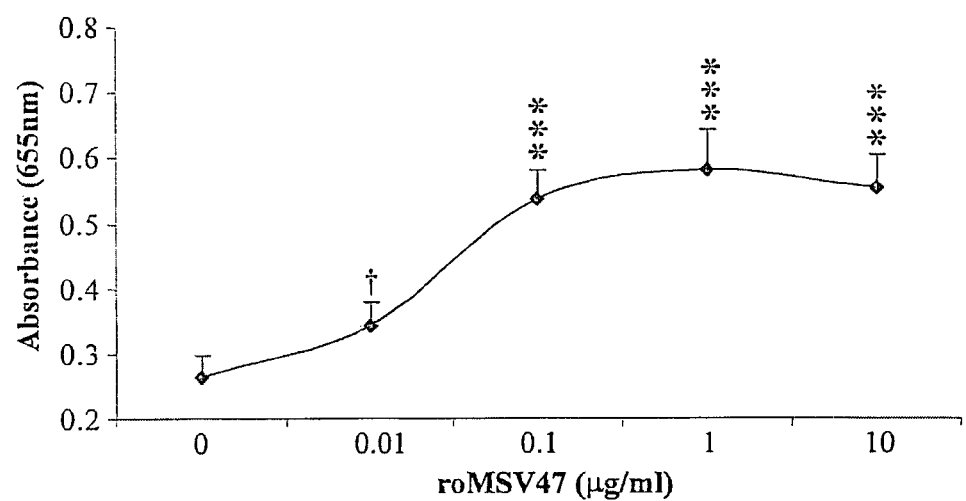
FIG. 10 shows the effect of roMSV47 protein on the proliferation of murine $C_2C_{12}$ myoblasts. Myoblasts were grown in the presence of increasing concentrations of roMSV47 (1-10,000 ng/ml) for 60 h. Cell proliferation was determined by methylene blue assay (absorbance at 655 nm). The dagger and asterisks indicate significant differences from time 0 (†P<0.1, ***P<0.001).

As shown in FIG. 10, recombinant ovine MSV47 (roMSV47) stimulates murine $C_2C_{12}$ myoblast proliferation. The cell replication curve of FIG. 10 indicates a characteristic dose-response to roMSV47 protein reaching maximum proliferation enhancing activity at about 0.1-0.5 µg/ml concentration. roMSV47 treatment results in a more than 2-fold increase in myoblast proliferation.

Figure 11:
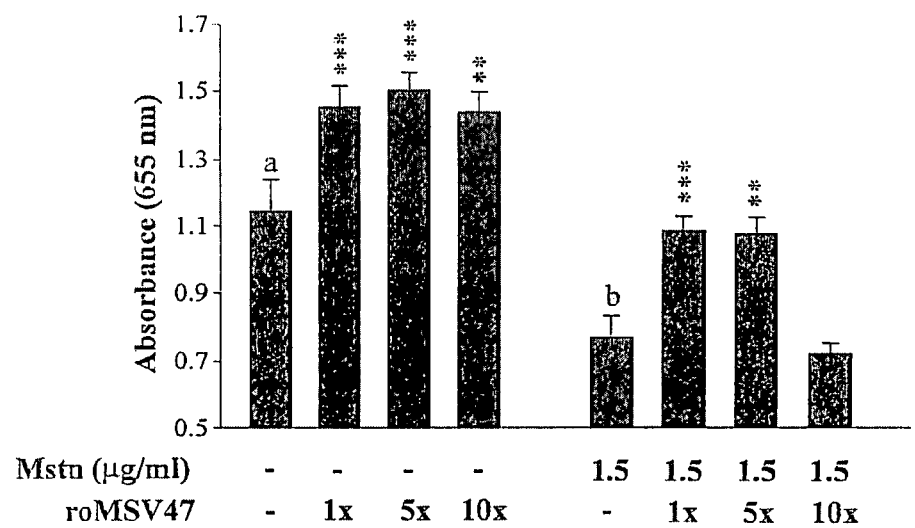
FIG. 11 shows mean (±SEM) proliferation of murine $C_2C_{12}$ myoblasts treated with and without myostatin (Mstn) and roMSV47 as indicated for 69 h. Doses of roMSV47 are in molar amounts (x) relative to the 1.5 µg/ml Mstn used in the second part of the assay. Unlike letters indicate significance (a,b P<0.001). Asterisks indicate significance relative to the first bar in each grouping (P<0.01, *P<0.001, n=8).

The ability of roMSV47 to out-compete myostatin in a $C_2C_{12}$ proliferation assay is shown in FIG. 11. roMSV47 was able to rescue myostatin inhibited myoblast proliferation at 1:1 (canonical myostatin:roMSV47) molar ratio at 1.5 µg/ml myostatin concentration. This recovery is greater than that seen for roMSV65, where rescue from myostatin inhibited proliferation required 1:20 molar ratio of myostatin: roMSV65. These data show that MSV47 acts as a potent antagonist of mature myostatin.

Figure 13:
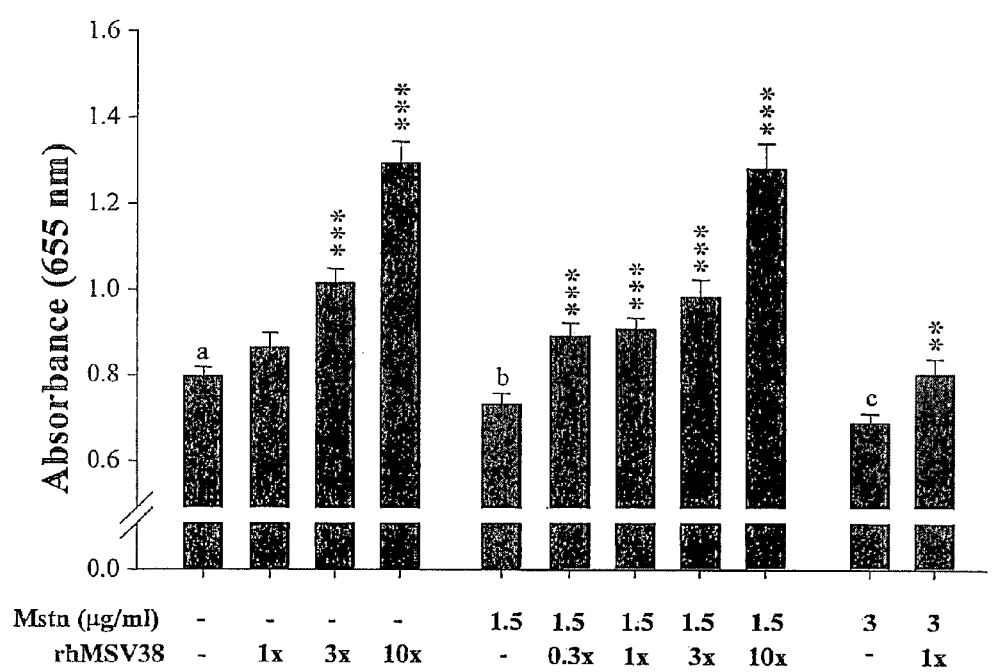
FIG. 13 shows the mean (±SEM) proliferation of primary human myoblasts treated with and without myostatin (Mstn) and rhMSV38 as indicated for 48 h. Doses of rhMSV38 are in molar amounts (x) relative to the 1.5 µg/ml Mstn used in the second part, or the 3 µg/ml Mstn used in the third part. Unlike letters indicate significance (a,b P<0.1, a,c P<0.01). Asterisks indicate significance relative to the first bar in each grouping (P<0.01, * P<0.001, n=8).

It is unclear why a 1:10 molar ratio of myostatin to MSV is ineffective at restoring proliferation in FIG. 11 and it is speculated that this is a spurious observation given that a 1:10 molar ratio of myostatin to rhMSV38, not only antagonises the action of myostatin, but increases proliferation beyond that of controls (FIG. 13). Alternatively, roMSV47 is a longer peptide than rhMSV38 and has two putative alpha helices (as opposed to the one of rhMSV38) and it is possible that the longer peptide cannot antagonise the actions of myostatin as effectively at higher concentrations due to steric hindrance at cognate receptors.

Figure 12:
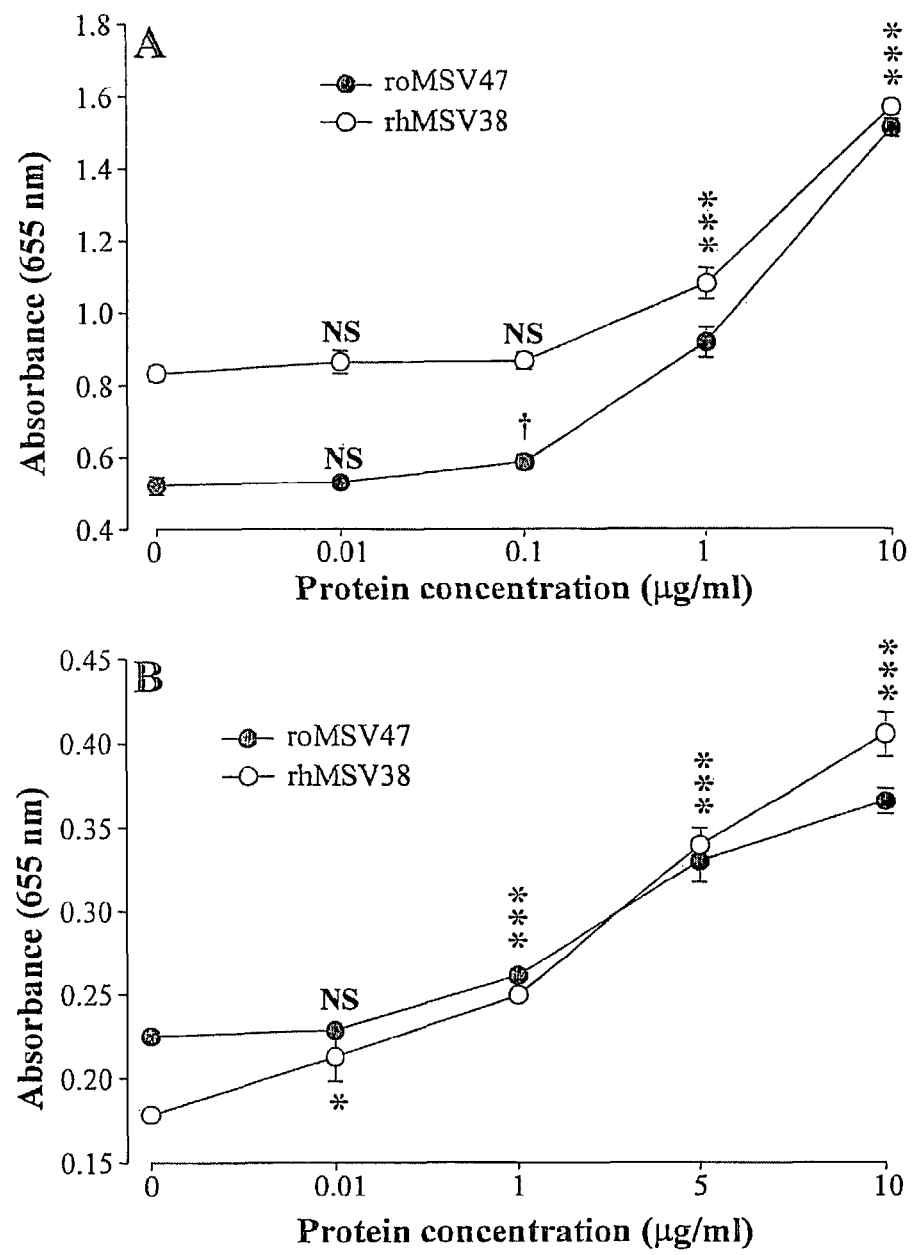
FIGS. 12A & B A, shows the effect of roMSV47 and rhMSV38 on proliferation of murine $C_2C_{12}$ myoblasts over 80 h. B, shows the effect of roMSV47 and rhMSV38 on proliferation of human myoblasts over 96 h (n=8). Cell proliferation was determined by methylene blue assay (absorbance at 655 nm). Symbols indicate significance (NS=not significant, †P<0.1, *P<0.05, ***P<0.001) from controls (0 µg/ml MSV) and where only one asterisk is used for a particular concentration, then that significance applies to both roMSV47 and rhMSV38.

The ability of recombinant ovine MSV47 (roMSV47) and recombinant human MSV38 (rhMSV38) to stimulate myoblast proliferation is shown in FIG. 12. FIG. 12A shows the effect of roMSV47 and rhMSV38 on proliferation of murine $C_2C_{12}$ myoblasts over 80 hours, while FIG. 12B shows the effect on proliferation of human myoblasts over 96 hours. These results show that MSV from one species is active on myoblasts of different species, and more importantly that the mature peptide is active and able to stimulate human myoblast proliferation indicating that the peptides offer a therapeutic activity for the treatment of muscle diseases in human, as well as other animals. FIG. 12 also shows that the preceding novel 18 amino acids, that remains with the LAP peptide after cleavage, is not required for proliferation as the roMSV47 is active.

The ability of rhMSV38 to out-compete myostatin in a human primary myoblast proliferation assay is shown in FIG. 13. The first of four columns show that rhMSV38 is able to stimulate proliferation of human primary myoblasts in a dose dependent manner. The middle five columns show that rhMSV38 is able to overcome the inhibitory effect of myostatin on the proliferation of the human myoblasts, beyond restoration to the control treatment receiving no myostatin. Restoration was also achieved at double the concentration of myostatin at a 1× molar ratio of rhMSV38:myostatin as shown in the final two columns of FIG. 13. These results further show that hMSV38 is active on human muscle and is able to counteract the inhibitory effect of myostatin on muscle growth and development.

Figure 14:
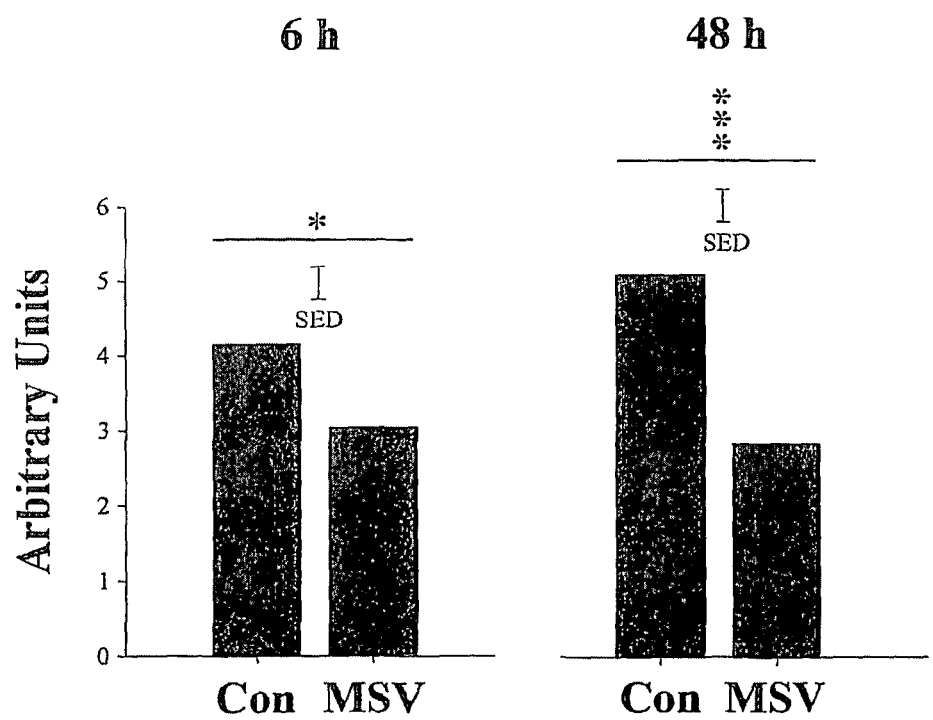
FIG. 14 shows the mean (±SEM) expression of myostatin as determined by real-time PCR in proliferating murine $C_2C_{12}$ myoblasts treated with or without roMSV47 (MSV) either chronically (from seeding to 48 h, n=4) or acutely for 6 h (from 48 to 54 h, n=4) in a separate population of $C_2C_{12}$ myoblasts grown to 48 h in DMEM medium supplemented with 2.5% fetal calf serum. Asterisks indicate significant differences from controls (Con, * P<0.05, *** P<0.001).

In addition to stimulating proliferation and antagonising the actions of myostatin, the effect of MSV on myostatin expression was also investigated. FIG. 14 shows that MSV (roMSV47) suppresses the expression of myostatin both chronically (from seeding to 48 h) and acutely (6 h from 48 to 54 h) in proliferating murine $C_2C_{12}$ myoblasts (FIG. 14). These data support the action of MSV acting to directly counteract the effect of myostatin and also to directly regulate the expression of myostatin, rather than merely competing against myostatin.

Functional Domain

A comparison of the different sequences is shown in FIG. 15, with the various fragments shown. Analysis of the sequences using In Silico analysis (GCG software) predicted the presence of two alpha helices separated by a six amino acid residue linker in the mature peptide. Interestingly, human, chimp cat and dog all only contain the first alpha helix, while bovine, ovine and porcine all contain both alpha helices. Because human, chimp cat and dog all only contain the first alpha helix, this implies that the first alpha helix may be responsible for the growth promoting activity of the MSV peptide. Supporting this is the fact that in the comparison there is greater conservation of residues in the putative alpha helices (58% in the first and 89% in the second helix). In an effort to identify the bioactive domain(s) of MSV, a number of recombinant and synthesised peptides were made. Recombinant alpha helix 1 (MSVα1, SEQ ID NO: 51) and recombinant alpha helix 2 (MSVα2, SEQ ID NO: 98) were produced. A third linker peptide (MSVL18, SEQ ID NO:100) was also constructed comprising the six C-terminal residues of the first alpha helix, the six linker residues, and the six N-terminal residues of the second alpha helix.

Figure 16:
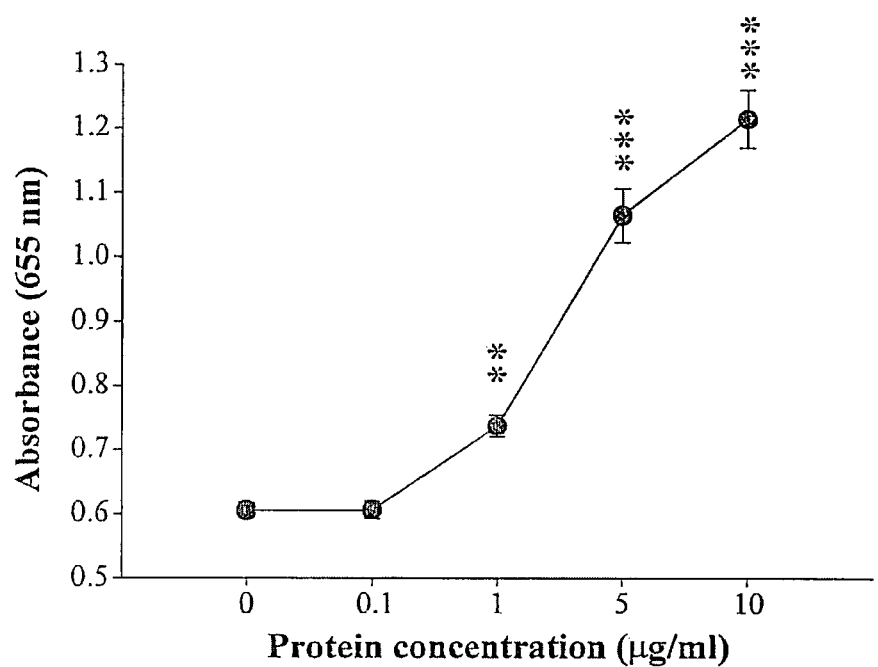
FIG. 16 shows the mean (±SEM) proliferation of murine $C_2C_{12}$ myoblasts treated with increasing amounts of the first alpha helix of ovine MSV (roMSVα1) for 72 h (n=8). Cell proliferation was determined by methylene blue assay (absorbance at 655 nm). Asterisks indicate significance from controls (no added roMSVα1,  P<0.01, * P<0.001).
Figure 17:
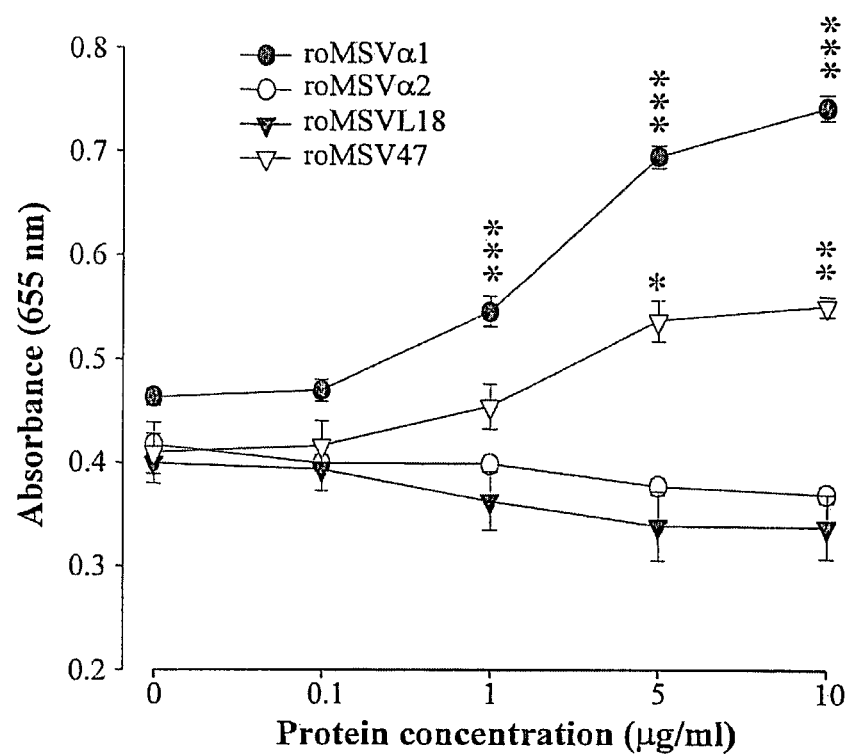
FIG. 17 shows the mean (±SEM) proliferation of murine $C_2C_{12}$ myoblasts treated with increasing amounts of roMSV47, roMSVα1, roMSVα2 and roMSVL18 for 80 h (n=8). Cell proliferation was determined by methylene blue assay (absorbance at 655 nm). Asterisks indicate significance from controls (no added peptide, * P<0.05,  P<0.01, * P<0.001).

To test whether MSVα1 is able to stimulate muscle proliferation, murine $C_2C_{12}$ myoblasts were grown in the presence of the peptide. As shown in FIG. 16, MSVα1 greatly stimulated the growth of the $C_2C_{12}$ cells in a dose dependent manner. A comparison of the effect of MSVα1, MSVα2, MSVL18 and roMSV47 on $C_2C_{12}$ proliferation is shown in FIG. 17. Both roMSV47 and MSVα1 were able to stimulate $C_2C_{12}$ cell growth in a dose dependent manner, while MSVα2 and MSVL18 had no effect.

These results show that the muscle growth stimulating activity of MSV is located in the first alpha helix. Furthermore, because both the MSV47 and MSV65 were active implies that any peptide containing this alpha helix will have muscle promoting activity.

The alignment of the sequences as shown in FIG. 15. allows a consensus sequence to be determined for the first alpha helix:

IIFLEVXIQFCSILGETAL (SEQ ID NO: 135)

Furthermore, by comparing the various sequences and the various polymorphisms identified, a formula for the base sequence for the first alpha helix can be established, which is as follows:

$X_1$ I F L E $X_2X_3X_4$Q $X_5$C S I L $X_6X_7X_8X_9X_{10}$ wherein; $X_1$ is I or L; $X_2$ is V or L; $X_3$ is Y, C, G or S; $X_4$ is I or F; $X_5$ is F or L; $X_6$ is G or E; $X_7$ is E or V, $X_8$ is A or T; $X_9$ is A or V, and $X_{10}$ is absent, F or L.

It should also be noted that the ionic charge of all of the amino acid residues in the first alpha helix have a consistent pattern for all of the sequences. That is, where there is a substitution, the different amino acid has been found to be similar in charge. The exception being residue 17 where both ovine and bovine have a hydrophobic residue rather than a polar residue. It will therefore be possible to make further changes in the sequence, retaining the ionic charge of that position, without substantially altering the activity of the peptide. It will be appreciated that such changes are incorporated within the scope of the present invention. The ionic charges for the 19 amino acid alpha helix are as follows:

HHHHAHPHPHPPHHPAP/HHH (Where; H=Hydrophobic, P=Polar, A=Acidic, B=Basic).

Cancer Induced Muscle Wasting

It has been shown that MSV is effective in antagonising that action of myostatin and promoting muscle growth in vitro. Therefore, MSV appears to be a good candidate for the treatment or prophylaxis for muscle wasting conditions. In order to test this, the effect of roMSV47 on muscle wasting in a rat model of cancer cachexia was tested.

In this study, 21 male rats (three months of age) were allocated at random into three groups of seven. Group one was injected i.p. with sterile saline (non-cancer controls), groups two and three were inoculated i.p. with 100 µl of the AH130 tumour (Baracos et al 1995). Groups one and two were injected twice daily s.c. for six days with sterile saline, while group three was injected twice daily s.c. for six days with 1 µg/g bodymass with roMSV47. Rats were killed at day six and, at death, skeletal muscles (biceps femoris, gastrocnemius, tibialis anterior, quadriceps femoris, plantaris and soleus) were excised from the right hind limb of each rat and the wet mass expressed as a percent of the initial body mass on day 0.

Figure 18:
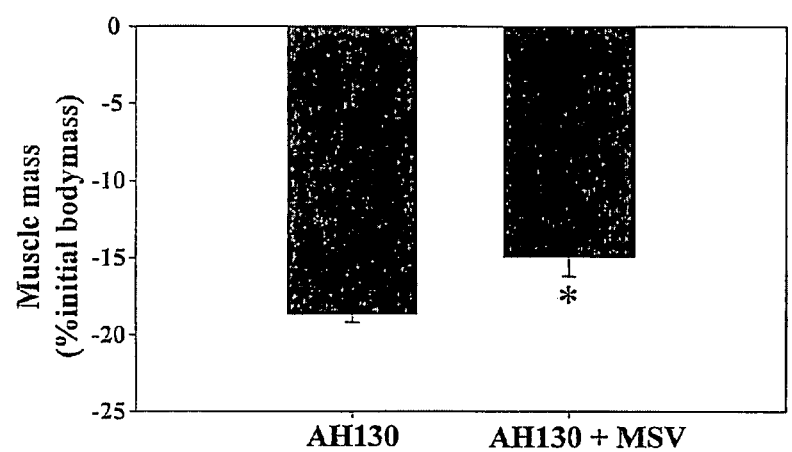
FIG. 18 shows the effect of recombinant ovine (ro) MSV47 protein on the extent of muscle wasting in rats injected with the AH130 tumour. Rats were inoculated on day zero with sterile saline (controls, n=7), and two groups were injected with 100 µl of AH130 i.p. and killed on day six. Control and one group of AH130 treated rats (AH130 controls, n=7) were injected twice daily s.c. for 6 d with sterile saline, while the second group of AH130 inoculated rats were injected twice daily s.c. with 1 µg roMSV47/g bodymass (n=7). Muscle mass from the combined wet mass of biceps femoris, gastrocnemius, tibialis anterior, quadriceps femoris, plantaris and soleus is expressed as percent of initial bodymass relative to non-cancer controls. Asterisks indicates significant difference from the AH130 cancer controls (*P<0.05).

As shown in FIG. 18, generalised wasting of skeletal muscle induced by cancer was reduced by 20%. Therefore these data show that roMS47 is effective in vivo and can reduce the severity of muscle wasting in cancer cachexia.

Creatine kinase catalyses the reversible transfer of a high-energy phosphate group between ATP and creatine and is an important energy generating enzyme in skeletal and heart muscle in situations of increased metabolic demand (Wyss and Kaddurah-Daouk 2000). When muscle is damaged CK is often released into blood and, therefore, increased concentrations of CK have been used as markers of injury as occurs after myocardial infarct and in muscular dystrophy (Wyss and Kaddurah-Daouk 2000). However, in skeletal muscle during cancer expression of CK has been found to be reduced (Buck and Chojkier 1996).

Figure 19:
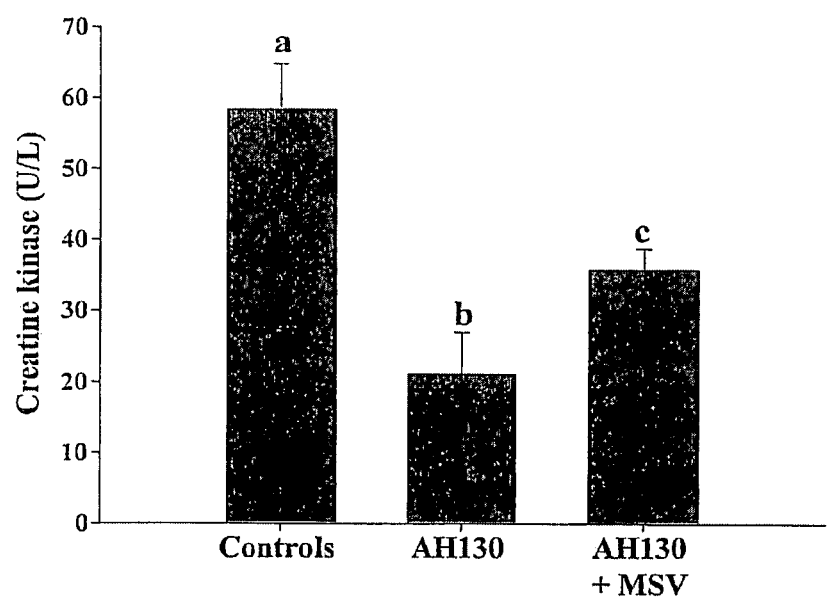
FIG. 19 shows that mean concentrations of creatine kinase (CK) were reduced at 6 d in rats bearing the AH130 tumour compared to the control rats. In contrast, concentrations of CK were not as markedly reduced in rats bearing the AH130 tumour, but injected twice daily with roMSV47 (MSV) (1 µg/g bodymass, s.c.) for 6 d. Unlike letters indicate significance (a,b $P<0.01$, a,c $P<0.01$, b,c $P<0.05$).

As shown in FIG. 19, levels of CK dropped in the untreated AH130 rats compared to the control rats that were not inoculated with the AH130 cells. However, treatment with roMSV47 partially restores concentrations of CK back to that of non-cancer controls.

These results show that MSV can act to prevent muscle wasting in pathological conditions. It should also be kept in mind that AH130 is an extremely aggressive cancer model, which induces severe cachexia in a very short period of time (days). It is very surprising that MSV was able to suppress such rapid muscle wasting and therefore MSV is likely to be effective in other less aggressive cancers and muscle wasting conditions.

Belgian Blue:

A deletion in myostatin has been found to be the cause of the muscular hypertrophy, commonly referred to as double muscling, observed in the Belgian Blue cattle breed. Belgian Blue cattle have been shown to have an 11-bp deletion in the coding region of mature myostatin causing a frameshift and a premature stop codon in exon 3, which results in the abolition of myostatin activity. The MSV of Belgian Blue cattle (bMSVbb) has also been isolated and characterised (SEQ ID NOS: 96 and 95). The bMSVbb gene (SEQ ID NO: 96) contains a 21-nucleotides deletion between nucleotides 749-770 of bMSV (SEQ ID NO: 5). The bMSVbb protein (SEQ ID NO: 95) is 314 amino acids long, seven amino acids shorter than bMSV (SEQ ID NO: 52). However, the deleted seven amino acids does not occur within the unique 65 amino acid C-terminal peptide and therefore the bMSV65 (SEQ ID NO: 53) and bMSV47 (SEQ ID NO: 54) are identical between normal cattle and the Belgian Blue breed. This conservation of the unique 65 amino acid C-terminal peptide indicates a functional importance of the MSV protein.

Two MSV-specific polyclonal antibodies were developed in rabbits using oligopeptides specific to the propeptide (N-terminal) and mature (C-terminal) region of ovine MSV. The localization of oligopeptides is based on the proposed processing of the precursor MSV at the KERK amino acid motif by propeptide convertases (PC1-7) including furin endopeptidase (Steiner 1998). The MSV propeptide-specific antibody (MPSA) can identify MSV precursor (37 kDa) and propeptide (29 kDa). The mature MSV-specific antibody (MMSA) is able to detect precursor (37 kDa) and mature (5.4 kDa monomer or a putative 11 kDa homo-dimer) MSV. Western immunoblotting employing MPSA consistently detects the precursor and propeptide of MSV in ovine skeletal muscle and brain but their ratio was different in these tissues (FIG. 8A). This may suggest that the efficiency of propeptide processing is vastly different in muscle and brain.

The PSA also identified MSV orthologs in human, pig, mouse and rat muscle and/or brain. There are other immunoreactive bands on the Western blot, which may be cleavage products of MSV precursor or covalently linked complexes of MSV proteins (Jiang et al. 2004). MMSA identifies the precursor protein in ovine muscle and brain but either the matured monomer (5.4 kDa) or homo-dimer (11 kDa) is undetectable (FIG. 8B).

FIG. 8B also shows immunoreactive bands at 11-12 kDa corresponding to the homo-dimers of mature MSV in human and rat muscle. This shows that MSV protein expression and processing also occurs in species other than sheep and cattle. MMSA identified mature MSV protein in a range of sheep serum samples (FIG. 8c). These data show that:

1) mature MSV protein may be secreted to the blood and circulates like other peptide hormones, and
2) a homo-dimer of mature MSV may be present in blood.

Putting the data together, MSV has been shown to be a potent antagonist of mature myostatin in myoblast replication and differentiation in vitro and able to reduce cancer muscle cachexia in vivo. MSV proteins have been detected in muscle of sheep and other species (cattle, human, pig, rat and mouse) and their abundance differ in genders and different physiological states. Mature MSV is also present in circulation in sheep. Furthermore, both the oMSV and hMSV have been shown to be active in cells from different species. These features make MSV a useful composition for enhancing muscle growth, regeneration, countering muscular dystrophies, altering body composition, bone and glucose metabolism. Furthermore it may be capable of promoting brain and spinal cord regeneration after injury.

EXPERIMENTAL PROCEDURES

Example 1

Identification and Cloning of Ovine and Bovine MSV

Ovine MSV

Ovine myostatin spice variant was first identified by reverse transcription polymerase chain reaction (RT-PCR) using flanking PCR primers around the open reading frame (ORF) of myostatin cDNA (complementary DNA sequence to myostatin messenger RNA). The forward primer (5'-TCAGACTGGGCAGGCATTAACG-3', SEQ ID NO: 101) located in the 5' untranslated region (UTR) and the reverse primer (5'-GCATATGGAGTTTTAAGACCA-3', SEQ ID NO: 102) in the distant 3'UTR. The PCR reaction was carried out with 20 of ovine muscle cDNA (reverse transcribed from mRNA of Texel sheep Muscle semitendinosus) as a template at 94° C. for 2 min for pre-amplification denaturation, and then at 94° C. for 30 sec, 55° C. for 1 min, and 72° C. for 2 min for 45 cycles. The PCR product was gel-purified using the Perfect Prep kit (Eppendorf, Germany) and cloned into the pGEM-T Easy E. coli plasmid vector according to the manufacturer's instructions (Promega, USA). The plasmid clone was given the name of pFJ106/3 and the insert was analysed at the Waikato DNA Sequencing Facility (Hamilton, New Zealand) by bi-directional sequencing from the T7 and Sp6 primers. The complete insert of pFJ106/3 was assembled in GSG/SeqLab software (Accelrys Inc., USA, SEQ ID NO: 1).

The completed sequence was then aligned with the canonical cDNA sequence of myostatin (GenBank accession number: AF019622). The alignment revealed 100% DNA sequence homology from nucleotide 1 (translational start site ATG in exon 1) to nucleotide 770 (exon 3) with the canonical myostatin cDNA, except a single silent mutation at position of 435 nucleotide (G→A transition). Furthermore, the alignment identified a novel translated DNA region of 195 nucleotides and a novel translational stop site (TAA). From the DNA sequence analysis it was concluded that clone pFJ106/3 identified a novel ovine myostatin isoform, which was generated by alternative splicing of a cryptic intron within exon 3 sequence of canonical ovine myostatin mRNA. The new myostatin isoform was named as an ovine myostatin splice variant (oMSV). The sequence identity of oMSV (SEQ ID NO: 1) was confirmed by RT-PCR amplification, cloning and sequencing of four independent clones of full-length ORF of oMSV.

Further cloning and sequencing of 3'UTR of the canonical ovine myostatin cDNA identified the position of splicing site at nucleotide 768, consensus splicing donor (SD3: GT) and acceptor (SA3: AG) sites of the cryptic intron (FIG. 1).

The ORF of oMSV encodes for a 321 amino acid protein (SEQ ID NO: 48). Amino acids 1 to 257 are identical with the canonical myostatin propeptide or LAP sequence. However, amino acids 257 to 321 (65aa) forms a novel C-terminal polypeptide sequence of oMSV dissimilar to canonical myostatin protein. Protein sequence and Western blot analysis using oMSV-specific antibody suggest that the 321aa full length oMSV protein may be processed at amino acid 275 following a KERK motif giving rise to a 274aa oMSV propeptide or LAP and a 47aa mature oMSV polypeptide.

Bovine MSV:

Bovine myostatin splice variants (bMSV) were identified with RT-PCR, and subsequent cloning and sequencing of the full-length ORF. The forward primer (5'-ACCATG-GAAAAACTCCAAATCTTT-3', SEQ ID NO: 103) located at the translational start site of bovine myostatin and the reverse primer (5'-GTCATCGTCATCTTTCATC-CTAAAAGCTGCAGT-3', SEQ ID NO: 104) at the predicted translational stop site of bMSV. The PCR reaction was carried out with 4 l of bovine muscle cDNA (reverse transcribed from mRNA of fetal Muscle semitendinosus of Hereford/Friesian cross or the double-muscled Belgian Blue cattle) as a template at 94° C. for 2 min for pre-amplification denaturation, and then at 94° C. for 30 sec, 55° C. for 30 sec, and 68° C. for 1 min for 45 cycles. The PCR products were gel-purified using the Perfect Prep kit (Eppendorf, Germany) and cloned into the pMT/V5-His-TOPO plasmid vector according to the manufacturer's instructions (Invitrogen, California). The inserts were analysed at the Waikato DNA Sequencing Facility (Hamilton, New Zealand) by bi-directional sequencing from the MTF1 and BGH primers. The complete insert sequences were assembled in GSG/SeqLab software (SEQ ID NO: 4).

The completed sequence bMSV (SEQ ID NO: 4) was aligned with the canonical cDNA sequence of myostatin (GenBank accession number: AF019620). The alignment revealed 100% DNA sequence homology from nucleotide 1 (translational start site ATG in exon 1) to nucleotide 770 (exon 3) with the canonical myostatin cDNA for the Hereford/Friesian cross, and 100% DNA sequence homology from nucleotide 1. (translational start site ATG in exon 1) to nucleotide 749 (exon 3) with the canonical myostatin cDNA for Belgian Blue cattle. It also identified a novel translated DNA region of 195 nucleotides and a novel translational stop site (TAA) in both cattle breeds.

Alignment of the full-length Hereford/Friesian cross (SEQ ID NO: 5) with the Belgian Blue (SEQ ID NO: 96) sequences identified a 21-nucleotide deletion in the Belgian Blue isoform of bMSV locating at nucleotides 749-770. The new bovine myostatin splice variants (bMSV) were named according to their specific breeds as Hereford/Friesian cross bovine myostatin splice variants (bMSVh/f: SEQ ID NO: 5) and Belgian Blue bovine myostatin splice variants (bMSVbb): SEQ ID NO: 96). Sequence identity of bMSV Was confirmed by RT-PCR amplification, cloning and sequencing of two independent clones of full-length ORF of bMSV and partial sequences spanning across the alternative splicing site. Alignment of bMSV cDNA with the genomic sequence of the bovine myostatin gene (GenBank accession number: AF320998) identified the consensus splicing donor (SD3: GT) and acceptor (SA3: AG) sites of the cryptic intron (FIG. 1).

The ORF of bMSVh/f encodes for a 321 amino acid protein (SEQ ID NO: 52), but the ORF of bMSVbb encodes for a 7aa shorter 314aa protein (SEQ ID NO: 95) but the rest of the protein sequence shows complete homology in the two breeds examined. Interestingly, the unique 65aa C-terminal peptide (SEQ ID NO: 53) is conserved in bMSVbb, which may indicate functional importance of this protein sequence region. Amino acids 1 to 257 in bMSVh/f racket SEQ ID NO: 52) and 1 to 250 in bbMSVbb (SEQ ID NO: 95) are identical with the canonical myostatin propeptide or LAP sequence. However, amino acids 257 to 321 (65aa) in bMSVh/f (SEQ ID NO: 52) and 250 to 314 in bMSVbb (SEQ ID NO: 95) represent a novel C-terminal polypeptide sequence of bMSV dissimilar to canonical bovine myostatin protein. Protein sequence and Western blot analysis using oMSV-specific antibody suggest that the 321aa full length bMSVh/f (314aa full length bMSVbb) protein may be processed at amino acid 275 (268) following a RERK motif giving rise to a 274aa bMSVh/f (267aa bMSVbb) propeptide or LAP and the same 47aa mature bMSVh/f or bMSVbb polypeptide (SEQ ID NO: 54).

Example 2

Northern Blot Analyses of Ovine MSV

To identify the size and abundance of ovine MSV, mRNA Northern blot analysis was employed. Frozen semitendinosus muscles of six adult male Romney sheep were homogenized on ice in Trizol Reagent (Invitrogen, California) for 30 seconds at 13 500 rpm using an Ultra Turrax homogenizer (Janke & Kunkel GmbH, Germany). Debris was removed by centrifugation for 10 minutes at 10,000 g and total RNA was isolated following the manufacturer's protocol (Invitrogen, California). RNA was re-suspended in diethyl pyrocarbonate-treated water and the total RNA concentration determined by measuring absorbance at 260 nm. About 600 microgram of total RNA were pooled and poly(A)+ RNA was purified with an mRNA Purification kit (Amersham Biosciences, UK) according to the manufacturer's instructions. Ten microgram of total and five microgram of poly(A)+ RNA were separated on a 1.2% formaldehyde-agarose gel, then transferred to uncharged nylon membrane (Hybond-N, Amersham Biosciences, UK) by capillary action. Membranes were cross-linked using ultra-violet radiation and stained with methylene blue to verify the integrity of RNA and the uniformity of transfer.

To identify canonical ovine myostatin and MSV mRNA species on Northern blot, specific DNA probes were made using reverse transcription polymerase chain reaction (RT-PCR). 5 microgram of total RNA from ovine skeletal muscle was reverse transcribed using a Superscript II Pre-Amplification kit (Invitrogen, California) according to the manufacturer's protocol. PCR was carried out with 2 ul of the reverse transcriptase reaction (94° C. for 30 sec, 55° C. for 1 min and 72° C. for 1 min) for 35 cycles and a final extension of 5 min at 72° C. Oligonucleotide primers homologous to exon1/2 of ovine myostatin were: 5'-ATGCAAAAACTG-CAAATCTCTG-3' (SEQ ID NO: 116) (forward, nt 1-22) and 5'-ATCAATGCTCTGCCAAATACC-3' (SEQ ID NO: 117) (reverse, nt 601-621). Two primer pairs were used to identify mRNA species having complementary sequences to the far 3' untranslated region (3'UTR) of ovine myostatin gene. These probes were called MSV1 and MSV2 could not hybridise to the canonical ovine myostatin mRNA (2.9 kb). PCR primers were the following: 5'-GCAAGGGTATATGGTCCTAGAG-3' Exon1/2 OMSV P1 (SEQ ID NO: 118) (forward, nt 2911-2932, MSV1), 5'-CACCAGAGAGAATTAGTCACTG-3' (SEQ ID NO: 119) (reverse, nt 3177-3198, MSV1), 5'-TAAAAGTCTGGGTCAGCAG-3' (SEQ ID NO: 120) (forward, nt 3461-3479, MSV2) and 5'-GCAAAAT-AGGGGGGGAAATG-3'(SEQ ID NO: 121) (reverse, nt 3731-3750, MSV2). Radio-labeled cDNA probes were prepared using [α-32P]dCTP and the Rediprime II Labeling Kit (Amersham Biosciences, UK) according to the manufacturer's instructions. The membrane was pre-hybridized in Church and Gilbert buffer for two hours (0.5 M Na2HPO4 pH 7.2, 7% SDS, 1 mM EDTA) at 55° C. The membrane was then hybridized at 55° C. overnight in fresh Church and Gilbert buffer with the appropriate radio-labeled probe. Following hybridization, they were washed at 55° C. for 15 minutes in each of 2×SSC/0.5% SDS, 1×SSC/0.5% SDS and 0.2×SSC/0.5% SDS and exposed against BioMax X-ray film (Eastman Kodak Company, Rochester, N.Y.) at −80° C. The autoradiograph was scanned using a densitometer (GS 800, BioRad Laboratories, Hercules, Calif.) and Quantity One software (BioRad). The blot was stripped with 0.5% SDS at 80° C., checked with autoradiography and then re-probed.

Example 3

Effect of Recombinant MSV on Myoblast Proliferation and Differentiation

Recombinant Expression and Purification of MSV Proteins

To test the biological effect of MSV proteins, the following recombinant peptides were made: ovine MSV65 (aa 257-321), ovine MSV47 (aa 275-321), ovine MSVα1 helix (aa 275-293), ovine MSV interlinking sequence (aa 287-305), ovine MSVα2 helix (aa 300-321), human MSV38 (aa 257-298). The appropriate DNA inserts for each were cloned, expressed and purified as a recombinant protein in $E.\ coli$. Pooled cDNA of human or sheep (Romney) skeletal muscle was used as a template to amplify MSV DNA inserts by polymerase chain reaction (PCR). The PCR products were obtained with the following forward and reverse primers, respectively: ovine MSV65 (aa 257-321) 5'-CACCGTG-CATTTTTACACTCCTCCCT-3' (SEQ ID NO: 122), 5'-TTATTTCATCCTAAAAGCTGCAG-3' (SEQ ID NO:123); ovine MSV47 (aa 275-321) 5'-CACCAT-CATTTTTCTAGAGGTCTAC-3' (SEQ ID NO:124), 5'-TTATTTCATCCTAAAAGCTGCAG-3' (SEQ ID NO:125); ovine MSVα1 helix (aa 275-297) 5'-CACCAT-CATTTTTCTAGAGGTCTAC-3' (SEQ ID NO:106), 5'-TTATGACTGCCTTTTAAACACAGC-3' (SEQ ID NO:107); ovine MSV interlinking sequence (aa 287-306) 5'-CACCATACTTGGAGAAGCTGTGTTT-3' (SEQ ID NO:126), 5'-TTAGAAATTTTGACAAAAATGAAT-3' (SEQ ID NO:127); ovine MSVα2 helix (aa 298-321) 5'-CACCAAAAGTATTCATTTTTGTCAA-3' (SEQ ID NO:128), 5'-TTATTTCATCCTAAAAGCTGCAG-3' (SEQ ID NO:129); human MSV38 (aa 257-298) 5'-CACCGTG-CATTTTCCTACACCTCCA-3' (SEQ ID NO:130), 5'-TTAAGATAATGCAGTTTCTCCAAG-3' (SEQ ID NO:131); PCR was carried out with 2 μl ovine muscle cDNA at 94° C. for 2 min as a pre-amplification denaturation, and then at 94° C. for 30 sec, 55° C. for 30 sec, and 72° C. for 30 sec for 35-45 cycles.

The PCR product was gel-purified using the Perfect Prep kit (Eppendorf, Germany) and cloned into pET100/D-TOPO (Invitrogen, California) $E.\ coli$ protein expression vector according to the manufacturer's instructions. The protein expression construct contains a 36 amino acid N-terminal tag including an Enterokinase cleavage site, Xpress epitope and a poly-His sequence. The resulting plasmid DNA construct was sequenced at the Waikato DNA Sequencing Facility (Hamilton, New Zealand) to confirm sequence identity. Twenty-five nanograms of plasmid DNA was transformed into BL21 A1 or BL21 Star $E.\ coli$ chemically competent protein expression $E.\ coli$ strain (Invitrogen, California) and a pilot protein expression experiment was carried out following the manufacturer's protocol (Invitrogen, California). Western blot analysis employing mouse monoclonal anti-Xpress-HRP (Invitrogen, California) and/or rabbit polyclonal anti-MSV65 or anti-MSV47 antibody (Functional Muscle Genomics Group, AgResearch, New Zealand) were used to confirm the expression of recombinant proteins in induced BL21 Star or BL21 A1 $E.\ coli$ cell extracts. The $E.\ coli$ host providing higher yield of recombinant protein was selected for large scale expression.

For large-scale expression of the recombinant proteins, 1 liter of Terrific Broth (Sigma, Missouri) supplemented with 100 μg/ml carbenicillin (Promega, California) was inoculated with 100 ml of overnight culture of the protein expression $E.\ coli$ strain. The protein expression was induced by the addition of 1 mM IPTG and 0.20% arabinose for BL21 A1 $E.\ coli$ or 1 mM IPTG BL21 Star $E.\ coli$ to the culture medium at the density of 0.4 $OD_{600}$ for BL21 A1 $E.\ coli$ or 0.8 $OD_{600}$ for BL21 Star $E.\ coli$, and the cells were allowed to express the recombinant protein for 4 h at 37° C. with shaking at 250 rpm. Protein expressing cells were collected by centrifugation of the culture at 6000×g for 15 min at 4° C., and washed with distilled water. The $E.\ coli$ cells were then frozen at −80° C. The following day the cells (5 g) were lysed in 25 ml of lysis buffer (25 mM $NaHPO_4$ pH 8.0, 500 mM NaCl, 250 μl protease inhibitor [P8849, Sigma, Missouri]) and mixed for 30 min at 4° C. on a rotating wheel. The lysate was then freeze/thawed in a dry ice/ethanol bath. The lysate was sonicated 10 times at an amplitude of 80 with 1 sec bursts for 1 min with 1 min breaks in between on wet ice and then passed through an 18-gauge needle to break genomic DNA. Cell debris was removed by centrifugation at 16000×g for 20 min at 4° C. and the supernatant incubated with 3 ml of Ni-NTA agarose resin with gentle shaking for 1 hour at 4° C. The lysate/resin mixture was applied to a column and the lysate allowed to flow through. The remaining resin was washed four times with 10 ml of wash buffer (25 mM NaHPO4 pH 7.0, 500 mM NaCl, 20 mM imidazole).

The recombinant protein was eluted from the resin with 5 ml elution buffer (25 mM $NaHPO_4$ pH 7.0, 500 mM NaCl, 250 mM imidazole) and dialysed in a SnakeSkin dialysis tube (MWCO 3,500, Pierce, Ill.) against 500 ml of dialysis buffer (20 mM TRIS-HCl pH 7.0, 150 mM NaCl) at 4° C. overnight. To remove endotoxins, the protein was then mixed with 25 μl of polymixin (BioRad) and incubated overnight on a rotating wheel. The polymixin was removed from the sample using a column and the resulting protein was dialyzed further two times in dialysis buffer (20 mM TRIS-HCl pH 7.0, 150 mM NaCl). The endotoxin-free recombinant protein solution was filter sterilized by passing it through a 0.22 μm filter unit (MillexGS, Millipore, Ireland). The protein concentration was determined using the bicinchoninic acid (BCA, Sigma, Missouri) protein assay. Size, purity and identity of the recombinant protein were verified by Western blot analysis and SDS-PAGE followed by Coomassie Brilliant Blue staining, and its bioactivity was tested in a murine $C_2C_{12}$ or human primary myoblast proliferation assay.

Proliferation Assays Using $C_2C_{12}$ Murine and Primary Ovine Myoblasts:

$C_2C_{12}$ murine and primary ovine myoblasts were employed to demonstrate that MSV promotes the proliferation of muscle cells. Myoblasts were seeded in 96-well tissue culture plates (Nunc, Roskilde, Denmark) at a cell density of 1000 cells per well in 200 μl of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. Medium was replaced with DMEM 10% FBS test medium containing 0, 0.001, 0.003, 0.01, 0.03, 0.1, 0.3, 1, 3 or 10 μg/ml oMSV65 in a semi-random arrangement of eight replicates (n=8) for each test medium. Plates were incubated at 37° C. with 5% $CO_2$ for 72 hours, and then the medium was removed. The wells were washed with 200 μl of phosphate buffered saline (PBS, Oxoid, UK) and fixed with 100 μl of 10% formaldehyde, 0.9% NaCl solution for at least one hour. The fixative was then removed and 100 μl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 μl 1:1 (v/v) ethanol/0.1 HCl. The plates were gently shaken and the absorbance was measured at 655 nm using a microplate photometer (FIGS. 3a and 3b). A plot of absorbance versus cell number was found to be linear in the range of interest (4000 to 30000 cells per cm2, Oliver et al. 1989).

p21 and PCNA Expression in roMSV65 Treated Proliferating $C_2C_{12}$ Myoblasts:

To further demonstrate that roMSV65 regulates the cell cycle of muscle cells two molecular markers: p21 and PCNA were used. p21 is a cycle-dependent kinase inhibitor, which regulates cell cycle progression by inducing G1 arrest and block entry into S phase by inactivating Cdks or by inhibiting activity of proliferating cell nuclear antigen (PCNA). Thus, a decrease in p21 protein expression may indicate an increased cell proliferation rate. PCNA is a positive marker of cell proliferation. It is a subunit of DNA polymerase-delta during DNA replication in the cell cycle. Higher level of PCNA protein expression is associated with higher number of cells entering the DNA replication phase of the cell cycle.

$C_2C_{12}$ myoblasts were seeded in 10 cm diameter tissue culture plates (Nunc, Roskilde, Denmark) at a cell density of 3000 cells per cm$^2$ in 10 ml of Dulbecco's modified Eagle's medium (DMEM, Invitrogen, California) supplemented with foetal bovine serum (FBS, 10% v/v, Invitrogen), penicillin ($1 \times 105$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. The medium was replaced with the test medium: DMEM with 10% FBS supplemented with, 0.1, 1 or 10 μg/ml oMSV65 (n=3). The plates were then incubated at 37° C. with 5% $CO_2$ for 48 hours. Cells were removed from the plate by trypsin treatment, washed with phosphate buffered saline (PBS, Oxoid, UK) and resuspended in 100 μl of lysis buffer (10 mM Hepes pH 7.9, 1.5 mM $MgCl_2$, 10 mM KCl, 0.5% NP40, one Complete protease inhibitor tablet [Roche Diagnostics, USA] per 50 ml buffer). The protein concentration was estimated using the bicinchoninic acid (BCA, Sigma, Missouri) protein assay. Twenty micrograms of total protein was separated by SDS-PAGE (12%) and transferred to nitrocellulose membrane by electroblotting. The blots were stained with Ponceau S stain to check equal loading. After washing the blot in TBST buffer they were blocked in TBST/5% non-fat milk for at least one hour and then incubated with 1:1000 dilution of mouse monoclonal anti-p21 (BD Pharmigen) or 1:500 dilution of rabbit polyclonal anti-PCNA (sc-7907, Santa Cruz) primary antibodies at 4° C. overnight. The membranes were washed with TBST (5×5 min) and incubated with either 1:2000 dilution of rabbit anti-mouse IgG-HRP (P0161, DAKO) or 1:2000 dilution of goat anti-rabbit IgG-HRP (P0448, DAKO) secondary antibodies at room temperature for 1 hour. The membranes were washed again with TBST (5×5 min) and developed with enhanced chemiluminescence. Band intensities were measured with a GS800 densitometer (BioRad, USA).

Developmental Myosin Heavy Chain (dMHC) and Myogenin Protein Expression in roMSV65 Treated Differentiating $C_2C_{12}$ Myoblasts:

To investigate whether roMSV65 regulates myoblast differentiation or myotube hypertrophy, $C_2C_{12}$ myoblast cultures were employed. Levels of well-established early and late molecular markers of myogenic differentiation like myogenin and dMHC were measured in the presence and absence of roMSV65 protein.

$C_2C_{12}$ myoblasts were seeded in 10 cm diameter tissue culture plates (Nunc, Roskilde, Denmark) at a cell density of 25,000 cells per cm$^2$ in 10 ml of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$.

To study myoblast differentiation, the medium was replaced with the test medium: DMEM with 2% Horse Serum supplemented with 0, 0.1, 1 or 10 μg/ml roMSV65 in three replicates for each concentration (n=3). Plates were incubated at 37° C. with 5% $CO_2$ for 72 hours.

Cells were removed from the plate by trypsin treatment, washed with phosphate buffered saline (PBS, Oxoid, UK) and resuspended in 200 μl of lysis buffer (10 mM Hepes pH 7.9, 1.5 mM $MgCl_2$, 10 mM KCl, 0.5% NP40, one Complete protease inhibitor tablet [Roche Diagnostics, USA] per 50 ml buffer). The protein concentration was estimated using the bicinchoninic acid (BCA, Sigma, Missouri) protein assay. 20 μg of total protein was separated by SDS-PAGE (8% for MHC or 12% for myogenin) and transferred to nitrocellulose membrane by electroblotting. The blots were stained with Ponceau S stain to check equal loading. After washing the blot in TBST buffer they were blocked in TBST/5% non-fat milk for myogenin, or in TBS buffer supplemented with 1% PVP-10, 1% PEG 4000, 0.3% BSA, 0.1% Tween 20 for dMHC and MHC for at least one hour and then incubated with the following primary antibodies: 1:1000 dilution of rabbit polyclonal anti-myogenin (sc-576, Santa Cruz Biotechnology, CA), 1:500 dilution of mouse monoclonal anti-rat dMHC (Novocastra Laboratories, Newcastle upon Tyne, UK) at 4° C. overnight. The membranes were washed with TBST (5×5 min) and incubated with either 1:2000 dilution of rabbit anti-mouse IgG-HRP (P0161, DAKO) or 1:2000 dilution of goat anti-rabbit IgG-HRP (P0448, DAKO) secondary antibodies at room temperature for 1 hour. The membranes were washed again with TBST (5×5 min) and developed with enhanced chemiluminescence. Band intensities were measured with a GS800 densitometer (Bio-Rad, CA).

Example 4 oMSV65 Competes with Canonical Myostatin

Competition of roMSV65 with canonical myostatin was carried out with $C_2C_{12}$ murine myoblasts. Myoblasts were seeded in 96-well tissue culture plates (Nunc, Roskilde, Denmark) at a cell density of 1000 cells per well in 200 µl of Dulbecco's modified Eagle's medium (DMEM, Invitrogen, California) supplemented with foetal bovine serum (FBS, 10% v/v, Invitrogen), penicillin ($1\times10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. The medium was replaced with DMEM 10% FBS test medium containing no added protein, 1.5 or 2.5 µg/ml recombinant myostatin alone and with combination of 1, 2, 4, 10, 20 molar ratio of roMSV65, and the same amounts of roMSV65 without myostatin in a semi-random arrangement of eight replicates (n=8) for each test medium. Plates were incubated at 37° C. with 5% $CO_2$ for 72 hours, and then the medium was removed. The wells were washed with 200 µl of phosphate buffered saline (PBS, Oxoid, UK) buffer and fixed with 100 µl of 10% formaldehyde, 0.9% NaCl solution for at least one hour. The fixative was then removed and 100 µl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 µl 1:1 (v/v) ethanol/0.1 HCl. The plates were gently shaken and the absorbance was measured at 655 nm using a microplate photometer (VersaMax, Molecular Devices, CA).

Example 5

MSV-Specific Antibodies and its Use for Detection of MSV Proteins in Tissues and Blood To specifically detect and quantitatively measure MSV proteins, two polyclonal anti-MSV antibodies were developed in rabbits.

Oligopeptides located at C-terminus of ovine MSV were synthesized, purified and conjugated to keyhole limpet haemocyanin (KLH) by Auspep (Parkville, Australia) for immunizations. The amino acid sequences of the oligopeptides were: CYTPPYGQWIFHKERK (aa 260-274 (SEQ ID NO: 1, MSV-FJ1) and CKRQSKSIHFGQNFK (aa 294-307 (SEQ ID NO: 1, MSV-FJ3). With the approval of the local Animal Ethics Committee (Ruakura Research Centre, Hamilton, New Zealand) two female New Zealand white rabbits were injected with each antigen separately. Primary injection consisted of the equivalent of 200 µg of test peptide in Freund's complete adjuvant followed by two booster injections at four-week intervals in Freund's incomplete adjuvant. Rabbits were then bled and left in collection tubes to clot for 4 hours at room temperature and serum was separated by centrifugation at 1000×g for 30 min at 4° C. Serum was stored at −80° C. until purification.

Immunoglobulin-G (IgG) was purified in two steps; first it was enriched by ammonium sulphate precipitation and further purified using a Protein A column. Briefly, 10 ml of serum was diluted 1:1 with 100 mM Tris pH 8.0 and solid $(NH_4)_2SO_4$ was added to a final concentration of 5% (m/v) with continuous stirring on ice. After incubation on ice for 30 min, the solution was centrifuged at 2000×g for 5 min at 4° C. and the clear supernatant was transferred to a beaker. The $(NH_4)_2SO_4$ concentration was increased to 50% (m/v) by adding solid $(NH_4)_2SO_4$ in the same manner as above. The solution was incubated on ice for 30 min and the precipitated protein centrifuged at 2000×g for 5 min at 4° C. The protein pellet was re-solubilised in 10 ml of 0.1 M Tris pH 8.0 and loaded on to an equilibrated Protein A column (P9424, Sigma, USA). The column was washed with 20 ml of 0.1 M glycine pH 8.0 and the IgG was eluted from the column with 10 ml of 0.1 M glycine pH 4.0, followed by 10 ml of 0.1 M glycine pH 3.0. 0.5 ml fractions were collected and mixed with 100 µl of 1 M Tris pH 8.0 on ice.

Protein concentration was estimated in each fraction using the BCA protein assay (Sigma, USA). Protein containing fractions were pooled and dialysed against 2 liters of 0.1 M $NaHCO_3$, 0.5 M NaCl. After dialysis, protein concentration was determined with the BCA protein assay (Sigma, USA) and the antibody solution was mixed 1:1 with glycerol to protect IgG from freeze damage, and stored at −20° C. The purified IgG was tested using a range of dilutions (1:300 to 1:30,000) as a primary antibody in Western immunoblotting.

These two MSV-specific antibodies allow the detection of precursor (37 kDa), pro-peptide (29 kDa) and mature (5.4 kDa) MSV proteins in ovine, bovine and possibly in other species. The antibodies can be used for Western blotting, immunoprecipitation, hystochemistry, cytochemistry and ELISA assays to comparatively measure, localise and quantify MSV proteins in complex protein extracts, cells, tissues and blood samples.

To investigate the specificity of antibodies, Western immunoblotting was employed. Briefly, 100 mg of tissue (for example muscle or brain) was homogenised in 1.0 ml of lysis buffer (10 mM Hepes pH 7.9, 1.5 mM $MgCl_2$, 10 mM KCl, 0.5% NP40, one Complete [Roche Diagnostics, USA] protease inhibitor tablet per 50 ml buffer) at 13,500 rpm for 30 sec on ice. The homogenate was centrifuged at 10,000×g for 5 min at 4° C. to remove tissue debris. The protein concentration of the supernatant was estimated using the bicinchoninic acid (BCA, Sigma, Missouri) protein assay with BSA standard. Protein extracts were mixed 2:1 with 3× Laemmli sample (6% SDS, 15% 2-mercaptoethanol, 30% glycerol, 187.5 mM Tris pH 6.8, 0.05% bromophenol blue buffer and incubated in boiling water for 5 min. 20 µg of total protein was separated by SDS-PAGE (15% for mature MSV or 10% for MSV propeptide) and transferred to nitrocellulose membrane by electroblotting. For blood samples, serum was mixed 1:1:1 with sterile water and 3× Laemmli sample buffer and incubated in boiling water for 5 min. Serum proteins equivalent to 2 µl neat serum was separated by 15% SDS-PAGE and transferred to nitrocellulose membrane by electroblotting. The blots were stained with Ponceau S stain to check equal loading. After washing the blots in TBST buffer they were blocked in TBS buffer supplemented with 1% PVP-10, 1% PEG 4000, 0.3% BSA, 0.1% Tween 20 for at least one hour and then incubated with MSV-specific primary antibodies (MPSA or MMSA) at 1:1000 dilution in the above blocking buffer at 4° C. overnight. The membranes were washed with TBST (5×5 min) and incubated with either 1:5000 dilution of goat anti-rabbit IgG-HRP (P0448, DAKO) secondary antibody at room temperature for 2 hour. The membranes were washed again with TBST (5×5 min) and developed with enhanced chemiluminescence.

Example 6

Effect of MSV Fragments

Cloning, Expression and Purification of Ovine MSV47:
To test the biological effect of oMSV47 on myoblast proliferation, it was cloned, expressed and purified as a recombinant protein in *E. coli*. Pooled sheep (Romney) skeletal muscle cDNA was used as a template to amplify oMSV47 by polymerase chain reaction (PCR). The PCR product was obtained with the following forward and reverse primers: 5'-CACCATCATTTTTCTAGAGGTCTAC-3' (SEQ ID NO: 106) and 5'-TTATTTCATCCTAAAAGCTGCAG-3 (SEQ ID NO: 107). PCR was carried out with 2 µl ovine muscle cDNA at 94° C. for 2 min as a pre-amplification denaturation, and then at 94° C. for 15 sec, 55° C. for 30 sec, and 68° C. for 30 sec for 40 cycles using Pfx Platinum Taq DNA polymerase (Invitrogen, California).

The PCR product was gel-purified using the Perfect Prep kit (Eppendorf, Germany) and cloned into pET100/D-TOPO (Invitrogen, California) *E. coli* protein expression vector according to the manufacturer's instructions. The protein expression construct contains a 36 amino acid N-terminal tag including an Enterokinase cleavage site, Xpress epitope and a hexa-His sequence. The resulting pFJMSV47.3/8 plasmid DNA construct was sequenced at the Waikato DNA Sequencing Facility (Hamilton, New Zealand) to confirm sequence identity. 46 ng of pFJMSV47.3/8 plasmid DNA was transformed into BL21 Star chemically competent protein expression *E. coli* strain (Invitrogen, California) and a pilot protein expression experiment was carried out following the manufacturer's protocol (Invitrogen, California). Western blot analysis using mouse monoclonal anti-Xpress-HRP (Invitrogen, California) and anti-MSV rabbit polyclonal (Agresearch) antibodies confirmed the expression of the roMSV47 protein in IPTG-induced BL21 Star *E. coli* cell extracts.

For large-scale expression of the recombinant oMSV47 protein, 3.6 liters of Terrific Broth (Sigma, Missouri) supplemented with 100 µg/ml carbenicillin (Invitrogen, California) and 1% glucose, and it was inoculated with 400 ml of overnight culture of the protein expression *E. coli* strain. The protein expression was induced by the addition of IPTG to the culture medium (at 1 mM final concentration) at the density of 0.8 $OD_{600}$, and the cells were allowed to express the recombinant protein for 4 h at 37° C. with shaking at 250 rpm. Protein expressing cells were collected by centrifugation of the culture at 5000×g for 10 min at 4° C., and washed with distilled water. The *E. coli* cells were lysed in 100 ml of lysis buffer (6M guanidine HCl, 20 mM $NaHPO_4$ pH 7.8, 500 mM NaCl, 5 mM 2-mercaptoethanol, Complete protease inhibitor [Roche Diagnostics, USA]) and sonicated on ice to complete cell lysis. The *E. coli* cell lysate was passed through an 18-gauge needle five times to break genomic DNA. Cell debris was removed by centrifugation at 3000×g for 15 min at 4° C. The lysate was then incubated with 5 ml of Ni-NTA agarose resin with gentle shaking for 1 hour at room temperature. The resin was separated from the cell lysate and washed twice with 10 ml of denaturing binding buffer (8M urea, 20 mM $NaHPO_4$ pH 7.8, 500 mM NaCl, 5 mM 2-mercaptoethanol). The resin was washed a further four times with denaturing wash buffer (8M urea, 20 mM NaHPO4 pH 6.0, 500 mM NaCl, 5 mM 2-mercaptoethanol).

The recombinant protein was eluted from the resin with 10 ml denaturing elution buffer (8M urea, 20 mM $NaHPO_4$ pH 4.0, 500 mM NaCl, 5 mM beta-mercaptoethanol) and dialysed in a SnakeSkin dialysis tube (MWCO 3,500, Pierce, Ill.) against 500 volume of dialysis buffer (20 mM TRIS-HCl pH 8.5, 150 mM NaCl) at 4° C. for 24 h. The protein concentration of the dialysed protein was determined using the bicinchoninic acid (BCA, Sigma, Missouri) protein assay. Size, purity and identity of the recombinant protein were verified by Western blot analysis, and its bioactivity was tested in a murine $C_2C_{12}$ myoblast proliferation assay.

Proliferation Assays Using $C_2C_{12}$ Murine and Primary Ovine Myoblasts:

$C_2C_{12}$ murine and primary ovine myoblasts were employed to demonstrate that roMSV47 promotes the proliferation of muscle cells. Myoblasts were seeded in 96-well tissue culture plates (Nunc, Roskilde, Denmark) at a cell density of 1000 cells per well in 200 µl of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. Medium was replaced with DMEM 10% FBS test medium containing 0, 0.01, 0.1, 1 or 10 µg/ml oMSV47 in a semi-random arrangement of eight replicates (n=8) for each test medium. Plates were incubated at 37° C. with 5% $CO_2$ for 60 hours, and then the medium was removed. The wells were washed with 200 µl of phosphate buffered saline (PBS, Oxoid, UK) and fixed with 100 µl of 10% formaldehyde, 0.9% NaCl solution for at least one hour. The fixative was then removed and 100 µl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 µl 1:1 (v/v) ethanol/0.1 HCl. The plates were gently shaken and the absorbance was measured at 655 nm using a microplate photometer (FIG. 9). A plot of absorbance versus cell number was found to be linear in the range of interest (4000 to 30000 cells per cm2, Oliver et al. 1989).

roMSV47/Canonical Myostatin Competition Assay:

Competition of roMSV47 with canonical myostatin was carried out with $C_2C_{12}$ murine myoblasts. Myoblasts were seeded in 96-well tissue culture plates (Nunc, Roskilde, Denmark) at a cell density of 1000 cells per well in 200 µl of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. The medium was replaced with DMEM 10% FBS test medium containing no added protein, 1.5 µg/ml recombinant bovine myostatin alone and with combination of 1, 5 and 10 molar ratio of roMSV47, and the same amounts of roMSV47 without myostatin in a semi-random arrangement of eight replicates (n=8) for each test medium. Plates were incubated at 37° C. with 5% $CO_2$ for 60 hours, and then the medium was removed. The wells were washed with 200 µl of phosphate buffered saline (PBS, Oxoid, UK) buffer and fixed with 100 µl of 10% formaldehyde, 0.9% NaCl solution for at least one hour. The fixative was then removed and 100 µl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 µl 1:1 (v/v) ethanol/0.1 HCl. The plates were gently shaken and the absorbance was measured at 655 nm using a microplate photometer (VersaMax, Molecular Devices, CA).

Effect of roMSV47, roMSVα1, roMSVα2, roMSVL18, rhMSV38 on Proliferation of $C_2C_{12}$ Murine Myoblasts.

$C_2C_{12}$ murine myoblasts were employed to demonstrate that the respective MSV peptides promote the proliferation of muscle cells. Myoblasts were seeded in 96-well tissue culture plates (Nunc, Roskilde, Denmark) at a cell density of 1000 cells per well in 2000 of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. Medium was replaced with DMEM 2.5% FBS test medium containing 0, 0.01, 0.1, 1, 5 or 10 μg/ml of the respective peptides in a semi-random arrangement of eight replicates (n=8) for each test medium. Plates were incubated at 37° C. with 5% $CO_2$ for 80 hours, and then the medium was removed. The wells were washed with 200 μl of phosphate buffered saline (PBS, Oxoid, UK) and fixed with 100 μl of 10% formaldehyde, 0.9% NaCl solution for at least one hour. The fixative was then removed and 100 μl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 μl 1:1 (v/v) ethanol/0.1 HCl. The plates were gently shaken and the absorbance was measured at 655 nm using a microplate photometer (VersaMax, Molecular Devices, CA).

rhMSV38 and roMSV47 Stimulate the Proliferation of Human Primary Myoblasts.

To demonstrate that rhMSV38 and roMSV47 are able to stimulate the replication of human skeletal muscle cells, they were tested in a proliferation assay. Human skeletal muscle myoblasts (Cambrex, Australia) were seeded in 96-well tissue culture plates (Nunc, Roskilde, Denmark) at a cell density of 2000 cells per well in 200 μl of Skeletal Muscle Basal Medium (Cambrex, Australia) supplemented with foetal bovine serum (FBS, 10% v/v, Cambrex, Australia), and incubated overnight at 37° C. with 5% $CO_2$. The medium was replaced with Dulbecco's modified Eagle's medium (DMEM, Invitrogen, California) supplemented with 5% foetal bovine serum (FBS, Invitrogen, California), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator with 0, 0.1, 1, 5 and 10 μg/ml rhMSV38 or roMSV47 protein in a semi-random arrangement of eight replicates (n=8) for each test medium. Plates were incubated at 37° C. with 5% $CO_2$ for 96 hours, and then the medium was removed. The wells were washed with 200 μl of phosphate buffered saline (PBS, Oxoid, UK) buffer and fixed with 100 μl of 10% formaldehyde, 0.9% NaCl solution for at least one hour. The fixative was then removed and 100 μl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 μl 1:1 (v/v) ethanol/0.1 HCl. The plates were gently shaken and the absorbance was measured at 655 nm using a microplate photometer (VersaMax, Molecular Devices, CA).

roMSV47 Outcompetes Mature Myostatin in a Proliferation Assay of Murine $C_2C_{12}$ Myoblasts.

Myoblasts were seeded in 96-well tissue culture plates (Nunc, Roskilde, Denmark) at a cell density of 1000 cells per well in 2000 of Dulbecco's modified Eagle's medium (DMEM, Invitrogen, California) supplemented with foetal bovine serum (FBS, 10% v/v, Invitrogen), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. The medium was replaced with DMEM 10% FBS test medium containing no added protein, 1.5 μg/ml recombinant bovine myostatin alone and with combination of 1, 5 and 10 molar ratio of roMSV47, and the same amounts of roMSV47 without myostatin in a semi-random arrangement of eight replicates (n=8) for each test medium. Plates were incubated at 37° C. with 5% $CO_2$ for 69 hours, and then the medium was removed. The wells were washed with 200 μl of phosphate buffered saline (PBS, Oxoid, UK) buffer and fixed with 100 μl of 10% formaldehyde, 0.9% NaCl solution for at least one hour. The fixative was then removed and 100 μl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 μl 1:1 (v/v) ethanol/0.1 HCl. The plates were gently shaken and the absorbance was measured at 655 nm using a microplate photometer (VersaMax, Molecular Devices, CA).

rhMSV38 Outcompetes Mature Myostatin in a Proliferation Assay of Human Primary Myoblasts Human skeletal muscle myoblasts (Cambrex, Australia) were seeded in 96-well tissue culture plates (Nunc, Roskilde, Denmark) at a cell density of 2000 cells per well in 200 μl of Skeletal Muscle Basal Medium (Cambrex, Australia) supplemented with foetal bovine serum (FBS, 10% v/v, Cambrex, Australia), and incubated overnight at 37° C. with 5% $CO_2$. The medium was replaced with Dulbecco's modified Eagle's medium (DMEM, Invitrogen, California) supplemented with 5% foetal bovine serum (FBS, Invitrogen, California), penicillin ($1 \times 10^5$ IU/l, Sigma, St Louis, Mo., USA) and streptomycin (100 mg/l, Sigma) buffered with $NaHCO_3$ containing phenol red (7.22 nmol/l) as a pH indicator with no added protein, 1.5 or 3.0 μg/ml recombinant bovine mature myostatin alone and with combination of 0.3, 1, 3, 10 molar ratio of rhMSV38 to myostatin, and the same amounts of rhMSV38 without myostatin in a semi-random arrangement of eight replicates (n=8) for each test medium. Plates were incubated at 37° C. with 5% $CO_2$ for 48 hours, and then the medium was removed. The wells were washed with 200 μl of phosphate buffered saline (PBS, Oxoid, UK) buffer and fixed with 100 μl of 10% formaldehyde, 0.9% NaCl solution for at least one hour. The fixative was then removed and 100 μl of 1% methylene blue stain in 0.01 M borate buffer (pH 8.5) was added to each well and incubated for 30 min at room temperature. Excess stain was removed by four sequential washes in borate buffer. Methylene blue was eluted from the cells by the addition of 100 μl 1:1 (v/v) ethanol/0.1 HCl. The plates were gently shaken and the absorbance was measured at 655 nm using a microplate photometer (VersaMax, Molecular Devices, CA).

roMSV47 Acutely and Chronically Down-Regulates Myostatin mRNA Expression in $C_2C_{12}$ Murine Myoblasts.

$C_2C_{12}$ myoblasts were seeded in 10 cm diameter tissue culture plates (Nunc, Roskilde, Denmark) at a cell density of 3000 cells per $cm^2$ in 10 ml of Dulbecco's modified Eagle's medium (DMEM, Invitrogen, California) supplemented with foetal bovine serum (FBS, 10% v/v, Invitrogen), penicillin ($1 \times 10^5$ IU/I, Sigma, St Louis, Mo., USA) and streptomycin (100 mg/l, Sigma) buffered with $NaHCO_3$ containing phenol red (7.22 nmol/l) as a pH indicator, and incubated overnight at 37° C. with 5% $CO_2$. For a set of eight plates (chronic treatment, designated "A") the medium was replaced with the test medium: DMEM with 2.5% FBS supplemented with 0 or 10 μg/ml oMSV47 (n=4). The plates "A" were then incubated at 37° C. with 5% $CO_2$ for 48 hours. For another set of eight plates (acute treatment, designated "B") the plating medium was replaced with DMEM with 2.5% FBS, and incubated at 37° C. with 5% $CO_2$ for 48 h, and then it was replaced with fresh test medium: DMEM with 2.5% FBS supplemented with 0 or 10 µg/ml oMSV47 (n=4). The plates "B" were then incubated at 37° C. with 5% $CO_2$ for 6 hours. After given treatments, the plates were washed with 10 ml PBS buffer and the cells were harvested with 2 ml of Trizol reagent. Total RNA was isolated with Trizol reagent following the manufacturer's protocol (Invitrogen, California). RNA was re-suspended in diethyl pyrocarbonate-treated water and the total RNA concentration determined by measuring absorbance at 260 nm (Nanodrop Spectrophotometer, Delaware, USA). Five micrograms of total RNA was reverse transcribed using a Superscript III Pre-Amplification kit (Invitrogen, California) according to the manufacturer's protocol. Oligonucleotide primers were used that span across the exon2/3 boundary of mouse myostatin (nt 715-796): forward primer 5'-GCTGTAACCTTCCCAGGACC-3' (SEQ ID NO: 132) and reverse primer 5'-GGGACCTCTTGGGTGTGTCT-3' (SEQ ID NO: 133). PCR was carried out with 2.5 µl of the reverse transcriptase reaction with following master mix for each LightCycler reaction: 4.5 µl water, 0.5 µl of 10 µM primers and 2.0 µl LightCycler FastStart DNA Master plus SYBR Green I reagent (Roche Diagnostics). A dilution series of mouse muscle reverse transcriptase reaction was used as a standard. The following experimental run protocol was used: denaturation (95° C. for 5 min), amplification (95° C. for 5 sec, 62° C. for 10 sec, 72° C. for 20 sec, with a single fluorescence measurement, 50 cycles), melt curve (60-95° C. with a heating rate of 0.1° C. per sec with continuous fluorescence measurement) on a LightCycler 2.0 PCR machine (Roche Diagnostics). Arbitrary concentrations were calculated by the Lightcycler software using a standard curve (Roche Diagnostics).

11. Effect of MSV on Muscle Mass During Cancer-Induced Cachexia.

The ascites hepatoma 130 (AH130) was obtained as a gift from Dr Vicki Baracos (University of Alberta, Edmonton, Alberta, Canada) and stored in cryovials in liquid nitrogen in a solution of 50% DMSO and 10% BSA. An aliquot was retrieved and thawed and 1 ml was injected i.p. into each of three donor rats and allowed to grow for seven days. The rats were killed by $CO_2$ asphyxiation followed by cervical dislocation. The ascites was harvested and 100 µl was injected i.p. into each of 14 recipient male rats (280±6 g). An equal volume of saline was injected i.p. into seven control rats. Of the 14 rats inoculated with the AH130 tumour, seven were injected s.c. twice daily with roMSV47 at a dose of 1 µg/g body mass diluted in sterile saline to a volume of 1 ml. The remaining seven rats inoculated with the tumour and the seven control rats were each injected s.c. twice daily with 1 ml of sterile saline. Growth of the tumour was allowed to progress for six days at which point all rats were killed as described above. At death, a blood sample was obtained from each rat via cardiac puncture and placed into tubes containing EDTA as anticoagulant. Serum was harvested and an aliquot was stored frozen at −20° C. for assay of creatine kinase (CK). The volume of ascites in the peritoneal cavity was removed with a syringe and the volume recorded. Six muscles in the right hind limb (biceps femoris, gastrocnemius, soleus, plantaris, tibialis anterior and quadriceps femoris) were excised and their mass recorded.

Mass of skeletal muscles in the AH130 experiment are presented pooled as a percent of the initial body mass (d0) and data are expressed relative to the muscle mass of control rats (those not inoculated with the tumour).

Creatine Kinase Assay

CK-NAC was assayed in a commercial kit (Randox laboratories Ltd, UK). Reaction volumes were scaled down proportionately so that the assays could be performed in 96-well microtitre plates with samples assayed in triplicate (CK-NAC) and read as a change in U/L per min as per manufacturer's instructions.

Assays, proliferation and competition studies were analyses using students t-tests or ANOVA with the statistical software package Genstat 8.0 (1).

Wherein in the foregoing description reference has been made to integers or components having known equivalents, such equivalents are herein incorporated as if individually set forth.

Although the invention has been described by way of example and with reference to possible embodiments thereof, it is to be appreciated that improvements and/or modifications may be made without departing from the scope or spirit thereof.

REFERENCES

Baracos V E, C DeVivo, D H R Hoyle and A L Goldberg. Activation of the ATP-ubiquitin-proteasome pathway in skeletal muscle of cachectic rats bearing a hepatoma. Am J Physiol 268:E996-E1006, 1995.

Bogdanovich S, Krag T O, Barton E R, Morris L D, Whittemore L A, Ahima R S, Khurana T S. (2002) Functional improvement of dystrophic muscle by myostatin blockade. Nature 420: 418-21.

Bradley, P., Misura, K. M. S, and Baker, D. (2005) Toward High-Resolution de Novo Structure Prediction for Small Proteins. Science 309, 1868-1871.

Buck M and M Chojkier. Muscle wasting and dedifferentiation induced by oxidative stress in a murine model of cachexia is prevented by inhibitors of nitric oxide synthesis and antioxidants. EMBO J 15: 1753-1765, 1996.

Celotto, A. M. and Graveley B. R. (2002) Exon-specific RNAi: A tool for dissecting the functional relevance of alternate splicing. RNA 8:718-724.

Dubois C M, Blanchette F, Laprise M H, Leduc R, Grondin F, Seidah N G (2001) Evidence that furin is an authentic transforming growth factor-beta1-converting enzyme. Am J Pathol 158:305-16.

Dubois C M, Blanchette F, Laprise M H, Leduc R, Grondin F, Seidah N G. (2001) Evidence that furin is an authentic transforming growth factor-beta1-converting enzyme. Am J Pathol 158: 305-16.

Gonzalez-Cadavid N F, Taylor W E, Yarasheski K, Sinha-Hikim I, Ma K, Ezzat S, Shen R, Lalani R, Asa S, Mamita M, Nair G, Arver S, Bhasin S. (1998) Organization of the human myostatin gene and expression in healthy men and HIV-infected men with muscle wasting. Proc Natl Acad Sci USA 95: 14938-43.

Grobet L, Martin Li, Poncelet D, et al. (1997) A deletion in the bovine myostatin gene causes the double-muscled phenotype in cattle. Nat Genet 17:71-74.

Hamrick M W (2003) Increased bone mineral density in the femora of GDF8 knockout mice. Anat Rec 272A(1): 388-91.

Hill J J, Davies M V, Pearson A A, et al. (2002) The myostatin propeptide and the follistatin-related gene are inhibitory binding proteins of myostatin in normal serum. J Biol Chem 277: 40735-40741.

Hill J J, Qiu Y, Hewick R M. (2003) Regulation of myostatin in vivo by growth and differentiation factor-associated serum protein-1: a novel protein with protease inhibitor and follistatin domains. Mol Endocrinol 17: 1144-1154.

Jiang M S, Liang L F, Wang S, Ratovitski T, Holmstrom J, Barker C, Stotish R. (2004) Characterization and identification of the inhibitory domain of GDF-8 propeptide. Biochem Biophys Res Commun 315: 525-31.

Joulia D, Bernardi H, Garandel V, Rabenoelina F, Vernus B, Cabello G. (2003) Mechanisms involved in the inhibition of myoblast proliferation and differentiation by myostatin. Exp Cell Res 286: 263-75.

Kambadur, R., Sharma, M., Smith, T. P. and Bass, J. J. (1997) Mutations in myostatin (GDF-8) in double muscled Belgian Blue and Piedmontese Cattle. Genome Res 7: 910-916.

Langley B, Thomas M, Bishop A, et al. (2002) Myostatin inhibits myoblast differentiation by down-regulating MyoD expression. J Biol Chem 277: 49831-49840.

Langley B, Thomas M, McFarlane C, Gilmour S, Sharma M, Kambadur R. (2004) Myostatin inhibits rhabdomyosarcoma cell proliferation through an Rb-independent pathway. Oncogene 23: 524-34.

Lee S J, McPherron A C. (2001) Regulation of myostatin activity and muscle growth. Proc Natl Acad Sci USA 98: 9306-9311.

Ma K, Mallidis C, Bhasin S, Mahabadi V, Artaza J, Gonzalez-Cadavid N, Arias J, Salehian B. (2003) Glucocorticoid-induced skeletal muscle atrophy is associated with upregulation of myostatin gene expression. Am J Physiol Endocrinol Metab 285: E363-E371.

McCroskery S, Thomas M, Maxwell L, Sharma M, Kambadur R. (2003) Myostatin negatively regulates satellite cell activation and self-renewal. J Cell Biol 162: 1135-47.

McPherron A C, Lawler A M, Lee S J. (1997) Regulation of skeletal muscle mass in mice by a new TGF-beta superfamily member. Nature 387: 83-90.

McPherron A C, Lee S J. (1997) Double muscling in cattle due to mutations in the myostatin gene. Proc Natl Acad Sci USA 94:12457-12461.

McPherron A C, Lee S J (2002) Suppression of body fat accumulation in myostatin-deficient mice. J Clin Invest 109: 595-601.

Montarras D, Chelly J, Bober E, Arnold H, Ott M O, Gros F, Pinset C. (1991) Developmental patterns in the expression of Myf5, MyoD, myogenin, and MRF4 during myogenesis. New Biol 3: 592-600.

Nicholas G, Thomas M, Langley B, et al. (2002) Titin-cap associates with, and regulates secretion of, myostatin. J Cell Physiol 193: 120-131.

Oliver M H, Harrison N K, Bishop J E, Cole P J, Laurent G J. (1989) A rapid and convenient assay for counting cells cultured in microwell plates: application for assessment of growth factors. J Cell Sci 92: 513-518.

Rebbapragada A, Benchabane H, Wrana J L, Celeste A J, Attisano L. (2003) Myostatin signals through a transforming growth factor beta-like signaling pathway to block adipogenesis. Mol Cell Biol 23: 7230-42.

Rios R, Carneiro I, Arce V M, Devesa J. (2001) Myostatin regulates cell survival during $C_2C_{12}$ myogenesis. Biochem Biophys Res Commun 280: 561-566.

Seidah N G, Chretien M (1997) Eukaryotic protein processing: endoproteolysis of precursor proteins. Curr Opin Biotechnol 8:602-7.

Seidah N G, Chretien M (1999) Proprotein and prohormone convertases: a family of subtilases generating diverse bioactive polypeptides. Brain Res 848:45-62.

Sharma M, Kambadur R, Matthews K G, Somers W G, Devlin G P, Conaglen J V, Fowke P J, Bass J J. (1999) Myostatin, a transforming growth factor-beta superfamily member, is expressed in heart muscle and is upregulated in cardiomyocytes after infarct. J Cell Physiol 180:1-9.

Spiller M P, Kambadur R, Jeanplong F, Thomas M, Martyn J K, Bass J J, Sharma M. (2002) The myostatin gene is a downstream target gene of basic helix-loop-helix transcription factor MyoD. Mol Cell Biol 22: 7066-82.

Steiner F D (1998) The protein convertases. Curr Opin Chem Biol 2:31-39.

Taylor W E, Bashin S, Artaza J, et al. (2001) Myostatin inhibits cell proliferation and protein synthesis in $C_2C_{12}$ muscle cells. Am J Physiol Endocrinol Metab 280: E221-E228.

Thies R S, Chen T, Davies M V, Tomkinson K N, Pearson A A, Shakey Q A, Wolfman N M. (2001) GDF-8 propeptide binds to GDF-8 and antagonizes biological activity by inhibiting GDF-8 receptor binding. Growth Factors 18:251-9.

Thomas M, Langley B, Berry C, et al. (2000) Myostatin, a negative regulator of muscle growth, functions by inhibiting myoblast proliferation. J Biol Chem 275: 40235-40243.

Uprichard, S. L. (In Press) The therapeutic potential of RNA interference. Febs letters.

Wang H, Zhang Q, Zhu D. (2003) hSGT interacts with tha N-terminal region of myostatin. Biochem Biophys Res Commun 311: 877-883.

Wyss M and R Kaddurah-Daouk. Creatine and creatinine metabolism. Physiological Reviews 80: 1107-1213, 2000.

Yang J, Ratovitski T, Brady J P, Solomon M B, Wells K D, Wall R J. (2001) Expression of myostatin pro domain results in muscular transgenic mice. Mol Reprod Dev 60: 351-61.

Zachwieja J J, Smith S R, Sinha-Hikim I, Gonzalez-Cadavid N, Bhasin S (1999) Plasma myostatin-immunoreactive protein is increased after prolonged bed rest with low-dose T3 administration. J Gravit Physiol 6: 11-5.

Zimmers T A, Davies M V, Koniaris L G, Haynes P, Esquela A F, Tomkinson K N, McPherron A C, Wolfman N M, Lee S J. (2002) Induction of cachexia in mice by systemically administered myostatin. Science 296:1486-s8.

What is claimed is:

1. An isolated polypeptide comprising an amino acid sequence having the formula:

$X_1$ I F L E $X_2$ $X_3$ $X_4$ Q $X_5$ C S I L $X_6$ $X_7$ $X_8$ $X_9$ $X_{10}$
(SEQ ID NO: 134)

wherein $X_1$ is I or L, $X_2$ is V or L, $X_3$ is Y, C, G or S, $X_4$ is I or F, $X_5$ is F or L, $X_6$ is G or E, $X_7$ is E or V, $X_8$ is A or T, $X_9$ is A or V and $X_{10}$ is absent, F or L, wherein the polypeptide promotes is capable of promoting myoblast cell growth.

2. An isolated polypeptide that is selected from:
(a) a polypeptide comprising an amino acid sequence of any one of SEQ ID NOS: 48-54, 56-62, 64-66, 68-77, 83-87, 89, 90 and 92-95; and (b) a polypeptide having at least 90% sequence identity with the polypeptide of (a), wherein the polypeptide promotes myoblast cell growth.

3. A method for regulating muscle growth, comprising administering to a subject in need thereof a composition comprising the polypeptide of claim 1 or 2.

4. A method for treating muscle cachexia in a subject a disease associated with muscle tissue, comprising administering to the subject in need thereof a composition comprising the polypeptide of claim 1 or 2.

* * * * *

SEQUENCE LISTING

<160> NUMBER OF SEQ ID NOS: 136

<210> SEQ ID NO 1
<211> LENGTH: 966
<212> TYPE: DNA
<213> ORGANISM: Ovis aries

<400> SEQUENCE: 1
atgcaaaaac tgcaaatctt tgtttatatt tacctattta tgctgcttgt tgctggccca       60

```
gtggatctga atgagaacag cgagcagaag gaaaatgtgg aaaaaaaggg gctgtgtaat    120
gcatgcttgt ggagacaaaa caataaatcc tcaagactag aagccataaa aatccaaatc    180
ctcagtaagc ttcgcctgga aacagctcct aacatcagca aagatgctat aagacaactt    240
ttgcccaagg ctcctccact ccgggaactg attgatcagt acgatgtcca gagagatgac    300
agcagcgacg gctccttgga agacgatgac taccacgtta cgacggaaac ggtcattacc    360
atgcccacgg agtctgatct tctagcagaa gtgcaagaaa acccaaatg ttgcttcttt    420 aaatttagct ctaaaataca acacaataaa gtagtaaagg cccaactgtg atatatctg    480 agacctgtca agactcctac aacagtgttt gtgcaaatcc tgagactcat caaacccatg    540
aaagacggta caaggtatac tggaatccga tctctgaaac ttgacatgaa cccaggcact    600
ggtatttggc agagcattga tgtgaagaca gtgttgcaaa actggctcaa acaacctgaa    660
tccaacttag gcattgaaat caaagcttta gatgagaatg gtcatgatct tgctgtaacc    720
ttcccagaac caggagaaga aggactgaat ccttttttag aagtcaaggt gcattttac    780 actcctccct atgggcaatg gattttccat aaagaaagaa aaatcatttt tctagaggtc    840
tacattcaat tctgtagcat acttggagaa gctgtgttta aaaggcagtc aaaaagtatt    900 cattttgtc aaaatttcaa aattatagcc tgcctttgca atactgcagc ttttaggatg    960
aaataa                                                               966

<210> SEQ ID NO 2
<211> LENGTH: 195
<212> TYPE: DNA
<213> ORGANISM: Ovis aries

<400> SEQUENCE: 2
gtgcattttt acactcctcc ctatgggcaa tggattttcc ataaagaaag aaaaatcatt     60
tttctagagg tctacattca attctgtagc atacttggag aagctgtgtt taaaaggcag    120
tcaaaaagta ttcatttttg tcaaaatttc aaaattatag cctgcctttg caatactgca    180
gcttttagga tgaaa                                                      195

<210> SEQ ID NO 3
<211> LENGTH: 141
<212> TYPE: DNA
<213> ORGANISM: Ovis aries

<400> SEQUENCE: 3 atcattttc tagaggtcta cattcaattc tgtagcatac ttggagaagc tgtgtttaaa      60
aggcagtcaa aaagtattca tttttgtcaa aatttcaaaa ttatagcctg cctttgcaat    120
actgcagctt ttaggatgaa a                                              141

<210> SEQ ID NO 4
<211> LENGTH: 57
<212> TYPE: DNA
<213> ORGANISM: Ovis aries

<400> SEQUENCE: 4 atcattttc tagaggtcta cattcaattc tgtagcatac ttggagaagc tgtgttt        57

<210> SEQ ID NO 5
<211> LENGTH: 966
<212> TYPE: DNA
<213> ORGANISM: Bos taurus

<400> SEQUENCE: 5
```

```
atgcaaaaac tgcaaatctc tgtttatatt tacctattta tgctgattgt tgctggccca      60
gtggatctga atgagaacag cgagcagaag gaaaatgtgg aaaaagaggg gctgtgtaat     120
gcatgtttgt ggagggaaaa cactacatcc tcaagactag aagccataaa aatccaaatc     180
ctcagtaaac ttcgcctgga aacagctcct aacatcagca aagatgctat cagacaactt     240
ttgcccaagg ctcctccact cctggaactg attgatcagt tcgatgtcca gagagatgcc     300
agcagtgacg gctccttgga agacgatgac taccacgcca ggacggaaac ggtcattacc     360
atgcccacgg agtctgatct tctaacgcaa gtggaaggaa acccaaatg ttgtttcttt      420 aaatttagct ctaagataca atacaataaa ctagtaaagg cccaactgtg gatatatctg     480
aggcctgtca agactcctgc gacagtgttt gtgcaaatcc tgagactcat caaacccatg     540
aaagacggta caaggtatac tggaatccga tctctgaaac ttgacatgaa cccaggcact     600
ggtatttggc agagcattga tgtgaagaca gtgttgcaga actggctcaa caacctgaa      660 tccaacttag gcattgaaat caaagcttta gatgagaatg ccatgatcct tgctgtaacc     720
ttcccagaac caggagaaga tggactgact cctttttag aagtcaaggt gcattttcac      780
actcctccct atgggcaatg gatgttctat agagaaagaa aactcatttt cctagaggtc     840
tacattcaat tctgtagcat acttggagaa gctgcattga aaaggcagtc aaaaagtatt     900
cattttggtc aaaatttcaa aattatagcc tgcctttgca atactgcagc ttttaggatg     960
aaataa                                                                966

<210> SEQ ID NO 6
<211> LENGTH: 195
<212> TYPE: DNA
<213> ORGANISM: Bos taurus

<400> SEQUENCE: 6
gtgcattttc acactcctcc ctatgggcaa tggatgttct atagagaaag aaaactcatt      60
ttcctagagg tctacattca attctgtagc atacttggag aagctgcatt gaaaaggcag     120
tcaaaaagta ttcattttgg tcaaaatttc aaaattatag cctgcctttg caatactgca     180
gcttttagga tgaaa                                                      195

<210> SEQ ID NO 7
<211> LENGTH: 141
<212> TYPE: DNA
<213> ORGANISM: Bos taurus

<400> SEQUENCE: 7
ctcattttcc tagaggtcta cattcaattc tgtagcatac ttggagaagc tgcattgaaa      60
aggcagtcaa aaagtattca ttttggtcaa aatttcaaaa ttatagcctg cctttgcaat     120
actgcagctt ttaggatgaa a                                               141

<210> SEQ ID NO 8
<211> LENGTH: 57
<212> TYPE: DNA
<213> ORGANISM: Bos taurus

<400> SEQUENCE: 8
ctcattttcc tagaggtcta cattcaattc tgtagcatac ttggagaagc tgcattg        57

<210> SEQ ID NO 9
<211> LENGTH: 195
<212> TYPE: DNA
<213> ORGANISM: Bos taurus
```

```
<400> SEQUENCE: 9
gtgcattttc acactcctcc ctatgggcaa tggatgttct atagagaaag aaaactcatt    60
ctcctagagg tctacattca attctgtagc atacttggag tagctgcatt gaaaaggcag   120
tcaaaaagta ttcattttgg tcaaaatttc aaaattatag cctgcctttg caatactgca   180
gcttttagga tgaaa                                                    195

<210> SEQ ID NO 10
<211> LENGTH: 141
<212> TYPE: DNA
<213> ORGANISM: Bos taurus

<400> SEQUENCE: 10
ctcattctcc tagaggtcta cattcaattc tgtagcatac ttggagtagc tgcattgaaa    60
aggcagtcaa aaagtattca ttttggtcaa aatttcaaaa ttatagcctg cctttgcaat   120
actgcagctt ttaggatgaa a                                             141

<210> SEQ ID NO 11
<211> LENGTH: 57
<212> TYPE: DNA
<213> ORGANISM: Bos taurus

<400> SEQUENCE: 11
ctcattctcc tagaggtcta cattcaattc tgtagcatac ttggagtagc tgcattg       57

<210> SEQ ID NO 12
<211> LENGTH: 195
<212> TYPE: DNA
<213> ORGANISM: Bos taurus

<400> SEQUENCE: 12
gtgcattttc acactcctcc ctatgggcaa tggatgttct atagagaaag aaaactcatt    60
ctcctagagg tctacattca attctgtagc atacttggag aagctgcatt gaaaaggcag   120
tcaaaaagta ttcattttgg tcaaaatttc aaaattatag cctgcctttg caatactgca   180
gcttttagga tgaaa                                                    195

<210> SEQ ID NO 13
<211> LENGTH: 141
<212> TYPE: DNA
<213> ORGANISM: Bos taurus

<400> SEQUENCE: 13
ctcattctcc tagaggtcta cattcaattc tgtagcatac ttggagaagc tgcattgaaa    60
aggcagtcaa aaagtattca ttttggtcaa aatttcaaaa ttatagcctg cctttgcaat   120
actgcagctt ttaggatgaa a                                             141

<210> SEQ ID NO 14
<211> LENGTH: 57
<212> TYPE: DNA
<213> ORGANISM: Bos taurus

<400> SEQUENCE: 14
ctcattctcc tagaggtcta cattcaattc tgtagcatac ttggagaagc tgcattg       57

<210> SEQ ID NO 15
<211> LENGTH: 195
<212> TYPE: DNA
<213> ORGANISM: Bos taurus
```

```
<400> SEQUENCE: 15
gtgcattttc acactcctcc ctatgggcaa tggatgttct atagagaaag aaaactcatt      60
ttcctagagg tctacattca attctgtagc atacttggag aagctgcatt gaaaaggcag     120
tcaaaaagta ttcattttgg ttcaaatttc aaaattatag cctgcctttg caatactgca     180
gcttttagga tgaaa                                                      195

<210> SEQ ID NO 16
<211> LENGTH: 141
<212> TYPE: DNA
<213> ORGANISM: Bos taurus

<400> SEQUENCE: 16 ctcatttttcc tagaggtcta cattcaattc tgtagcatac ttggagaagc tgcattgaaa     60
aggcagtcaa aaagtattca ttttggtcaa aatttcaaaa ttatagcctg cctttgcaat    120
actgcagctt ttaggatgaa a                                              141

<210> SEQ ID NO 17
<211> LENGTH: 57
<212> TYPE: DNA
<213> ORGANISM: Bos taurus

<400> SEQUENCE: 17
ctcattttcc tagaggtcta cattcaattc tgtagcatac ttggagaagc tgcattg         57

<210> SEQ ID NO 18
<211> LENGTH: 195
<212> TYPE: DNA
<213> ORGANISM: Bos indicus

<400> SEQUENCE: 18
gtgcattttc acactcctcc ctatgggcaa tggatgttct ataaagaaag aaaactcatt      60
ttcctagagg tctacattca attctgtagc atacttggag aagctgcatt gaaaaggcag     120
tcaaaaagta ttcattttgg tcaaaatttc aaaattatag cctgcctttg caatactgca    180
gcttttagga tgaaa                                                      195

<210> SEQ ID NO 19
<211> LENGTH: 141
<212> TYPE: DNA
<213> ORGANISM: Bos indicus

<400> SEQUENCE: 19
ctcattttcc tagaggtcta cattcaattc tgtagcatac ttggagaagc tgcattgaaa      60
aggcagtcaa aaagtattca ttttggtcaa aatttcaaaa ttatagcctg cctttgcaat    120
actgcagctt ttaggatgaa a                                              141

<210> SEQ ID NO 20
<211> LENGTH: 57
<212> TYPE: DNA
<213> ORGANISM: Bos indicus

<400> SEQUENCE: 20
ctcattttcc tagaggtcta cattcaattc tgtagcatac ttggagaagc tgcattg         57

<210> SEQ ID NO 21
<211> LENGTH: 195
<212> TYPE: DNA
<213> ORGANISM: Bos grunniens, Yak
```

```
<400> SEQUENCE: 21
gtgcattttc acactcctcc ctatgggcaa tggatgttct ataaagaaag gaaaatcatt    60
ttcctagagg tctacattca attctgtagc atacttggag aagctgcact gaaaaggcag   120
tcaaaaagta ttcattttgg tcaaaatttc aaaattatag cctgcctttg caatactgca   180
gcttttaggg tgaaa                                                    195

<210> SEQ ID NO 22
<211> LENGTH: 141
<212> TYPE: DNA
<213> ORGANISM: Bos grunniens, Yak

<400> SEQUENCE: 22
atcattttcc tagaggtcta cattcaattc tgtagcatac ttggagaagc tgcactgaaa    60
aggcagtcaa aaagtattca ttttggtcaa aatttcaaaa ttatagcctg cctttgcaat   120
actgcagctt tagggtgaaa a                                             141

<210> SEQ ID NO 23
<211> LENGTH: 57
<212> TYPE: DNA
<213> ORGANISM: Bos grunniens, Yak

<400> SEQUENCE: 23
atcattttcc tagaggtcta cattcaattc tgtagcatac ttggagaagc tgcactg       57

<210> SEQ ID NO 24
<211> LENGTH: 204
<212> TYPE: DNA
<213> ORGANISM: Sus scrofa

<400> SEQUENCE: 24
gtgcattttc atactctttc aaatggagaa tggattttct ttaatgaaag aaaaatcatt    60
tttctagagc tctgcattca attctgtagc atacttggag aaactgcatt taaaaggcag   120
ccaaaaagta ttcattttta tcaaaatttc aaaattatag cctgcctttg caacactgca   180
gtttttatga taaaatcatg gcaa                                          204

<210> SEQ ID NO 25
<211> LENGTH: 150
<212> TYPE: DNA
<213> ORGANISM: Sus scrofa

<400> SEQUENCE: 25 atcattttc tagagctctg cattcaattc tgtagcatac ttggagaaac tgcatttaaa     60
aggcagccaa aaagtattca tttttatcaa aatttcaaaa ttatagcctg cctttgcaac   120
actgcagttt ttatgataaa atcatggcaa                                    150

<210> SEQ ID NO 26
<211> LENGTH: 57
<212> TYPE: DNA
<213> ORGANISM: Sus scrofa

<400> SEQUENCE: 26 atcattttc tagagctctg cattcaattc tgtagcatac ttggagaaac tgcattt        57

<210> SEQ ID NO 27
<211> LENGTH: 114
<212> TYPE: DNA
<213> ORGANISM: Homo sapiens
```

<400> SEQUENCE: 27
gggcattttc ctacacctcc aaatgaggaa tggattttct ttaatgtaag aagaatcatt    60
tttctagagg ttggctttca attctgtagc atacttggag aaactgcatt atct         114

<210> SEQ ID NO 28
<211> LENGTH: 60
<212> TYPE: DNA
<213> ORGANISM: Homo sapiens

<400> SEQUENCE: 28
atcatttttc tagaggttgg ctttcaattc tgtagcatac ttggagaaac tgcattatct    60

<210> SEQ ID NO 29
<211> LENGTH: 57
<212> TYPE: DNA
<213> ORGANISM: Homo sapiens

<400> SEQUENCE: 29
atcatttttc tagaggttgg ctttcaattc tgtagcatac ttggagaaac tgcatta       57

<210> SEQ ID NO 30
<211> LENGTH: 114
<212> TYPE: DNA
<213> ORGANISM: Homo sapiens

<400> SEQUENCE: 30
gtgcattttc ctacacctcc aaatgaggaa tggattttct ttaatgtaag aagaatcatt    60
tttctagagg ttggctttca attctgtagc atacttggag aaactgcatt atct         114

<210> SEQ ID NO 31
<211> LENGTH: 60
<212> TYPE: DNA
<213> ORGANISM: Homo sapiens

<400> SEQUENCE: 31
atcatttttc tagaggttgg ctttcaattc tgtagcatac ttggagaaac tgcattatct    60

<210> SEQ ID NO 32
<211> LENGTH: 57
<212> TYPE: DNA
<213> ORGANISM: Homo sapiens

<400> SEQUENCE: 32
atcatttttc tagaggttgg ctttcaattc tgtagcatac ttggagaaac tgcatta       57

<210> SEQ ID NO 33
<211> LENGTH: 114
<212> TYPE: DNA
<213> ORGANISM: Pan troglodytes

<400> SEQUENCE: 33
gtgcattttc ctacacctcc aaatgaggaa tggattttct ttaatgtaag aagaatcatt    60
tttctagagg ttggctttca attctgtagc atacttggag aaactgcatt atct         114

<210> SEQ ID NO 34
<211> LENGTH: 60
<212> TYPE: DNA
<213> ORGANISM: Pan troglodytes

<400> SEQUENCE: 34
atcatttttc tagaggttgg ctttcaattc tgtagcatac ttggagaaac tgcattatct    60

```
<210> SEQ ID NO 35
<211> LENGTH: 57
<212> TYPE: DNA
<213> ORGANISM: Pan troglodytes

<400> SEQUENCE: 35 atcattttc tagaggttgg ctttcaattc tgtagcatac ttggagaaac tgcatta        57

<210> SEQ ID NO 36
<211> LENGTH: 108
<212> TYPE: DNA
<213> ORGANISM: Canis familiaris

<400> SEQUENCE: 36
gtgcattttc acacacctcc caatggggaa tggattttct ttaatgaaag aagaatcatt     60
tttctagagg tcagcattca attctgtagc atacttgaag aaactgca               108

<210> SEQ ID NO 37
<211> LENGTH: 54
<212> TYPE: DNA
<213> ORGANISM: Canis familiaris

<400> SEQUENCE: 37 atcattttc tagaggtcag cattcaattc tgtagcatac ttgaagaaac tgca           54

<210> SEQ ID NO 38
<211> LENGTH: 54
<212> TYPE: DNA
<213> ORGANISM: Canis familiaris

<400> SEQUENCE: 38 atcattttc tagaggtcag cattcaattc tgtagcatac ttgaagaaac tgca           54

<210> SEQ ID NO 39
<211> LENGTH: 108
<212> TYPE: DNA
<213> ORGANISM: Canis familiaris

<400> SEQUENCE: 39
gtgcattttc acacacctcc caatggggaa tggattttct ttaatgaaag aagaatcatt     60
tttctagagg tcagctttca attctgtagc atacttgaag aaactgca               108

<210> SEQ ID NO 40
<211> LENGTH: 54
<212> TYPE: DNA
<213> ORGANISM: Canis familiaris

<400> SEQUENCE: 40 atcattttc tagaggtcag ctttcaattc tgtagcatac ttgaagaaac tgca           54

<210> SEQ ID NO 41
<211> LENGTH: 54
<212> TYPE: DNA
<213> ORGANISM: Canis familiaris

<400> SEQUENCE: 41 atcattttc tagaggtcag ctttcaattc tgtagcatac ttgaagaaac tgca           54

<210> SEQ ID NO 42
<211> LENGTH: 108
<212> TYPE: DNA
<213> ORGANISM: Canis familiaris
```

```
<400> SEQUENCE: 42
gtgcattttc acacacctcc caatggggaa tggattttct ttaatgaaag aagaatcatt    60
tttctagagg tcagcattca actctgtagc atacttgaag aaactgca               108

<210> SEQ ID NO 43
<211> LENGTH: 54
<212> TYPE: DNA
<213> ORGANISM: Canis familiaris

<400> SEQUENCE: 43 atcattttc tagaggtcag cattcaactc tgtagcatac ttgaagaaac tgca            54

<210> SEQ ID NO 44
<211> LENGTH: 54
<212> TYPE: DNA
<213> ORGANISM: Canis familiaris

<400> SEQUENCE: 44 atcattttc tagaggtcag cattcaactc tgtagcatac ttgaagaaac tgca            54

<210> SEQ ID NO 45
<211> LENGTH: 114
<212> TYPE: DNA
<213> ORGANISM: Felis catus

<400> SEQUENCE: 45
gtgcattgtc atacacctcc aaatggggaa tggattttct ttaatgaaag aagaatcatt    60
tttctagagg tcagcattca attctgtagc atacttgaag aaactgcatt atct        114

<210> SEQ ID NO 46
<211> LENGTH: 60
<212> TYPE: DNA
<213> ORGANISM: Felis catus

<400> SEQUENCE: 46 atcattttc tagaggtcag cattcaattc tgtagcatac ttgaagaaac tgcattatct    60

<210> SEQ ID NO 47
<211> LENGTH: 57
<212> TYPE: DNA
<213> ORGANISM: Felis catus

<400> SEQUENCE: 47 atcattttc tagaggtcag cattcaattc tgtagcatac ttgaagaaac tgcatta       57

<210> SEQ ID NO 48
<211> LENGTH: 321
<212> TYPE: PRT
<213> ORGANISM: Ovis aries

<400> SEQUENCE: 48

Met Gln Lys Leu Gln Ile Phe Val Tyr Ile Tyr Leu Phe Met Leu Leu
1               5                   10                  15

Val Ala Gly Pro Val Asp Leu Asn Glu Asn Ser Glu Gln Lys Glu Asn
            20                  25                  30

Val Glu Lys Lys Gly Leu Cys Asn Ala Cys Leu Trp Arg Gln Asn Asn
        35                  40                  45

Lys Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80
```

```
Leu Pro Lys Ala Pro Leu Arg Glu Leu Ile Asp Gln Tyr Asp Val
            85                  90                  95

Gln Arg Asp Asp Ser Asp Gly Ser Leu Glu Asp Asp Tyr His
            100                 105                 110

Val Thr Thr Glu Thr Val Ile Thr Met Pro Thr Glu Ser Asp Leu Leu
            115                 120                 125

Ala Glu Val Gln Glu Lys Pro Lys Cys Cys Phe Phe Lys Phe Ser Ser
130                 135                 140

Lys Ile Gln His Asn Lys Val Lys Ala Gln Leu Trp Ile Tyr Leu
145                 150                 155                 160

Arg Pro Val Lys Thr Pro Thr Val Phe Val Gln Ile Leu Arg Leu
            165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Glu Pro Gly Glu Glu Gly Leu Asn Pro Phe Leu Glu Val Lys
            245                 250                 255

Val His Phe Tyr Thr Pro Pro Tyr Gly Gln Trp Ile Phe His Lys Glu
            260                 265                 270

Arg Lys Ile Ile Phe Leu Glu Val Tyr Ile Gln Phe Cys Ser Ile Leu
            275                 280                 285

Gly Glu Ala Val Phe Lys Arg Gln Ser Lys Ser Ile His Phe Cys Gln
            290                 295                 300

Asn Phe Lys Ile Ile Ala Cys Leu Cys Asn Thr Ala Ala Phe Arg Met
305                 310                 315                 320

Lys

<210> SEQ ID NO 49
<211> LENGTH: 65
<212> TYPE: PRT
<213> ORGANISM: Ovis aries

<400> SEQUENCE: 49

Val His Phe Tyr Thr Pro Pro Tyr Gly Gln Trp Ile Phe His Lys Glu
1               5                   10                  15

Arg Lys Ile Ile Phe Leu Glu Val Tyr Ile Gln Phe Cys Ser Ile Leu
            20                  25                  30

Gly Glu Ala Val Phe Lys Arg Gln Ser Lys Ser Ile His Phe Cys Gln
        35                  40                  45

Asn Phe Lys Ile Ile Ala Cys Leu Cys Asn Thr Ala Ala Phe Arg Met
    50                  55                  60

Lys
65

<210> SEQ ID NO 50
<211> LENGTH: 47
<212> TYPE: PRT
<213> ORGANISM: Ovis aries

<400> SEQUENCE: 50

Ile Ile Phe Leu Glu Val Tyr Ile Gln Phe Cys Ser Ile Leu Gly Glu
```

```
                  1               5                  10                 15
Ala Val Phe Lys Arg Gln Ser Lys Ser Ile His Phe Cys Gln Asn Phe
                20                 25                 30

Lys Ile Ile Ala Cys Leu Cys Asn Thr Ala Ala Phe Arg Met Lys
            35                 40                 45
```

<210> SEQ ID NO 51
<211> LENGTH: 19
<212> TYPE: PRT
<213> ORGANISM: Ovis aries

<400> SEQUENCE: 51

```
Ile Ile Phe Leu Glu Val Tyr Ile Gln Phe Cys Ser Ile Leu Gly Glu
1               5                  10                 15

Ala Val Phe
```

<210> SEQ ID NO 52
<211> LENGTH: 321
<212> TYPE: PRT
<213> ORGANISM: Bos taurus

<400> SEQUENCE: 52

```
Met Gln Lys Leu Gln Ile Ser Val Tyr Ile Tyr Leu Phe Met Leu Ile
1               5                  10                 15

Val Ala Gly Pro Val Asp Leu Asn Glu Asn Ser Glu Gln Lys Glu Asn
                20                 25                 30

Val Glu Lys Glu Gly Leu Cys Asn Ala Cys Leu Trp Arg Glu Asn Thr
            35                 40                 45

Thr Ser Ser Arg Leu Glu Ala Ile Lys Ile Gln Ile Leu Ser Lys Leu
        50                 55                 60

Arg Leu Glu Thr Ala Pro Asn Ile Ser Lys Asp Ala Ile Arg Gln Leu
65                  70                 75                 80

Leu Pro Lys Ala Pro Pro Leu Leu Glu Leu Ile Asp Gln Phe Asp Val
                85                 90                 95

Gln Arg Asp Ala Ser Ser Asp Gly Ser Leu Glu Asp Asp Tyr His
            100                105                110

Ala Arg Thr Glu Thr Val Ile Thr Met Pro Thr Glu Ser Asp Leu Leu
        115                120                125

Thr Gln Val Glu Gly Lys Pro Lys Cys Cys Phe Phe Lys Phe Ser Ser
    130                135                140

Lys Ile Gln Tyr Asn Lys Leu Val Lys Ala Gln Leu Trp Ile Tyr Leu
145                 150                155                160

Arg Pro Val Lys Thr Pro Ala Thr Val Phe Val Gln Ile Leu Arg Leu
                165                170                175

Ile Lys Pro Met Lys Asp Gly Thr Arg Tyr Thr Gly Ile Arg Ser Leu
            180                185                190

Lys Leu Asp Met Asn Pro Gly Thr Gly Ile Trp Gln Ser Ile Asp Val
        195                200                205

Lys Thr Val Leu Gln Asn Trp Leu Lys Gln Pro Glu Ser Asn Leu Gly
    210                215                220

Ile Glu Ile Lys Ala Leu Asp Glu Asn Gly His Asp Leu Ala Val Thr
225                 230                235                240

Phe Pro Glu Pro Gly Glu Asp Gly Leu Thr Pro Phe Leu Glu Val Lys
                245                250                255

Val His Phe His Thr Pro Pro Tyr Gly Gln Trp Met Phe Tyr Arg Glu
            260                265                270
```

```
Arg Lys Leu Ile Leu Leu Glu Val Tyr Ile Gln Phe Cys Ser Ile Leu
        275                 280                 285

Gly Glu Ala Ala Leu Lys Arg Gln Ser Lys Ser Ile His Phe Gly Gln
    290                 295                 300

Asn Phe Lys Ile Ile Ala Cys Leu Cys Asn Thr Ala Ala Phe Arg Met
305                 310                 315                 320

Lys
```

```
<210> SEQ ID NO 53
<211> LENGTH: 65
<212> TYPE: PRT
<213> ORGANISM: Bos taurus

<400> SEQUENCE: 53

Val His Phe His Thr Pro Pro Tyr Gly Gln Trp Met Phe Tyr Arg Glu
1               5                   10                  15

Arg Lys Leu Ile Phe Leu Glu Val Tyr Ile Gln Phe Cys Ser Ile Leu
            20                  25                  30

Gly Glu Ala Ala Leu Lys Arg Gln Ser Lys Ser Ile His Phe Gly Gln
        35                  40                  45

Asn Phe Lys Ile Ile Ala Cys Leu Cys Asn Thr Ala Ala Phe Arg Met
    50                  55                  60

Lys
65
```

```
<210> SEQ ID NO 54
<211> LENGTH: 47
<212> TYPE: PRT
<213> ORGANISM: Bos taurus

<400> SEQUENCE: 54

Leu Ile Phe Leu Glu Val Tyr Ile Gln Phe Cys Ser Ile Leu Gly Glu
1               5                   10                  15

Ala Ala Leu Lys Arg Gln Ser Lys Ser Ile His Phe Gly Gln Asn Phe
            20                  25                  30

Lys Ile Ile Ala Cys Leu Cys Asn Thr Ala Ala Phe Arg Met Lys
        35                  40                  45
```

```
<210> SEQ ID NO 55
<211> LENGTH: 19
<212> TYPE: PRT
<213> ORGANISM: Bos taurus

<400> SEQUENCE: 55

Leu Ile Phe Leu Glu Val Tyr Ile Gln Phe Cys Ser Ile Leu Gly Glu
1               5                   10                  15

Ala Ala Leu
```

```
<210> SEQ ID NO 56
<211> LENGTH: 65
<212> TYPE: PRT
<213> ORGANISM: Bos taurus

<400> SEQUENCE: 56

Val His Phe His Thr Pro Pro Tyr Gly Gln Trp Met Phe Tyr Arg Glu
1               5                   10                  15

Arg Lys Leu Ile Leu Leu Glu Val Tyr Ile Gln Phe Cys Ser Ile Leu
            20                  25                  30

Gly Val Ala Ala Leu Lys Arg Gln Ser Lys Ser Ile His Phe Gly Gln
        35                  40                  45
```

```
Asn Phe Lys Ile Ile Ala Cys Leu Cys Asn Thr Ala Ala Phe Arg Met
    50                  55                  60
Lys
65

<210> SEQ ID NO 57
<211> LENGTH: 47
<212> TYPE: PRT
<213> ORGANISM: Bos taurus

<400> SEQUENCE: 57

Leu Ile Leu Leu Glu Val Tyr Ile Gln Phe Cys Ser Ile Leu Gly Val
1               5                   10                  15

Ala Ala Leu Lys Arg Gln Ser Lys Ser Ile His Phe Gly Gln Asn Phe
            20                  25                  30

Lys Ile Ile Ala Cys Leu Cys Asn Thr Ala Ala Phe Arg Met Lys
        35                  40                  45

<210> SEQ ID NO 58
<211> LENGTH: 19
<212> TYPE: PRT
<213> ORGANISM: Bos taurus

<400> SEQUENCE: 58

Leu Ile Leu Leu Glu Val Tyr Ile Gln Phe Cys Ser Ile Leu Gly Val
1               5                   10                  15

Ala Ala Leu

<210> SEQ ID NO 59
<211> LENGTH: 65
<212> TYPE: PRT
<213> ORGANISM: Bos taurus

<400> SEQUENCE: 59

Val His Phe His Thr Pro Pro Tyr Gly Gln Trp Met Phe Tyr Arg Glu
1               5                   10                  15

Arg Lys Leu Ile Leu Glu Val Tyr Ile Gln Phe Cys Ser Ile Leu
            20                  25                  30

Gly Glu Ala Ala Leu Lys Arg Gln Ser Lys Ser Ile His Phe Gly Gln
        35                  40                  45

Asn Phe Lys Ile Ile Ala Cys Leu Cys Asn Thr Ala Ala Phe Arg Met
    50                  55                  60
Lys
65

<210> SEQ ID NO 60
<211> LENGTH: 47
<212> TYPE: PRT
<213> ORGANISM: Bos taurus

<400> SEQUENCE: 60

Leu Ile Leu Leu Glu Val Tyr Ile Gln Phe Cys Ser Ile Leu Gly Glu
1               5                   10                  15

Ala Ala Leu Lys Arg Gln Ser Lys Ser Ile His Phe Gly Gln Asn Phe
            20                  25                  30

Lys Ile Ile Ala Cys Leu Cys Asn Thr Ala Ala Phe Arg Met Lys
        35                  40                  45

<210> SEQ ID NO 61
<211> LENGTH: 19
```

```
<212> TYPE: PRT
<213> ORGANISM: Bos taurus

<400> SEQUENCE: 61

Leu Ile Leu Leu Glu Val Tyr Ile Gln Phe Cys Ser Ile Leu Gly Glu
1               5                   10                  15

Ala Ala Leu

<210> SEQ ID NO 62
<211> LENGTH: 65
<212> TYPE: PRT
<213> ORGANISM: Bos taurus

<400> SEQUENCE: 62

Val His Phe His Thr Pro Pro Tyr Gly Gln Trp Met Phe Tyr Arg Glu
1               5                   10                  15

Arg Lys Leu Ile Phe Leu Glu Val Tyr Ile Gln Phe Cys Ser Ile Leu
                20                  25                  30

Gly Glu Ala Ala Leu Lys Arg Gln Ser Lys Ser Ile His Phe Gly Ser
            35                  40                  45

Asn Phe Lys Ile Ile Ala Cys Leu Cys Asn Thr Ala Ala Phe Arg Met
        50                  55                  60

Lys
65

<210> SEQ ID NO 63
<211> LENGTH: 47
<212> TYPE: PRT
<213> ORGANISM: Bos taurus

<400> SEQUENCE: 63

Leu Ile Phe Leu Glu Val Tyr Ile Gln Phe Cys Ser Ile Leu Gly Glu
1               5                   10                  15

Ala Ala Leu Lys Arg Gln Ser Lys Ser Ile His Phe Gly Gln Asn Phe
                20                  25                  30

Lys Ile Ile Ala Cys Leu Cys Asn Thr Ala Ala Phe Arg Met Lys
            35                  40                  45

<210> SEQ ID NO 64
<211> LENGTH: 19
<212> TYPE: PRT
<213> ORGANISM: Bos taurus

<400> SEQUENCE: 64

Leu Ile Phe Leu Glu Val Tyr Ile Gln Phe Cys Ser Ile Leu Gly Glu
1               5                   10                  15

Ala Ala Leu

<210> SEQ ID NO 65
<211> LENGTH: 65
<212> TYPE: PRT
<213> ORGANISM: Bos indicus

<400> SEQUENCE: 65

Val His Phe His Thr Pro Pro Tyr Gly Gln Trp Met Phe Tyr Lys Glu
1               5                   10                  15

Arg Lys Leu Ile Phe Leu Glu Val Tyr Ile Gln Phe Cys Ser Ile Leu
                20                  25                  30

Gly Glu Ala Ala Leu Lys Arg Gln Ser Lys Ser Ile His Phe Gly Gln
            35                  40                  45
```

```
Asn Phe Lys Ile Ile Ala Cys Leu Cys Asn Thr Ala Ala Phe Arg Met
    50                  55                  60

Lys
65

<210> SEQ ID NO 66
<211> LENGTH: 47
<212> TYPE: PRT
<213> ORGANISM: Bos indicus

<400> SEQUENCE: 66

Leu Ile Phe Leu Glu Val Tyr Ile Gln Phe Cys Ser Ile Leu Gly Glu
1               5                   10                  15

Ala Ala Leu Lys Arg Gln Ser Lys Ser Ile His Phe Gly Gln Asn Phe
            20                  25                  30

Lys Ile Ile Ala Cys Leu Cys Asn Thr Ala Ala Phe Arg Met Lys
        35                  40                  45

<210> SEQ ID NO 67
<211> LENGTH: 19
<212> TYPE: PRT
<213> ORGANISM: Bos indicus

<400> SEQUENCE: 67

Leu Ile Phe Leu Glu Val Tyr Ile Gln Phe Cys Ser Ile Leu Gly Glu
1               5                   10                  15

Ala Ala Leu

<210> SEQ ID NO 68
<211> LENGTH: 65
<212> TYPE: PRT
<213> ORGANISM: Bos grunniens, Yak

<400> SEQUENCE: 68

Val His Phe His Thr Pro Pro Tyr Gly Gln Trp Met Phe Tyr Lys Glu
1               5                   10                  15

Arg Lys Ile Ile Phe Leu Glu Val Tyr Ile Gln Phe Cys Ser Ile Leu
            20                  25                  30

Gly Glu Ala Ala Leu Lys Arg Gln Ser Lys Ser Ile His Phe Gly Gln
        35                  40                  45

Asn Phe Lys Ile Ile Ala Cys Leu Cys Asn Thr Ala Ala Phe Arg Val
    50                  55                  60

Lys
65

<210> SEQ ID NO 69
<211> LENGTH: 47
<212> TYPE: PRT
<213> ORGANISM: Bos grunniens, Yak

<400> SEQUENCE: 69

Ile Ile Phe Leu Glu Val Tyr Ile Gln Phe Cys Ser Ile Leu Gly Glu
1               5                   10                  15

Ala Ala Leu Lys Arg Gln Ser Lys Ser Ile His Phe Gly Gln Asn Phe
            20                  25                  30

Lys Ile Ile Ala Cys Leu Cys Asn Thr Ala Ala Phe Arg Val Lys
        35                  40                  45

<210> SEQ ID NO 70
<211> LENGTH: 19
<212> TYPE: PRT
```

```
<213> ORGANISM: Bos grunniens, Yak

<400> SEQUENCE: 70

Ile Ile Phe Leu Glu Val Tyr Ile Gln Phe Cys Ser Ile Leu Gly Glu
1               5                   10                  15

Ala Ala Leu

<210> SEQ ID NO 71
<211> LENGTH: 68
<212> TYPE: PRT
<213> ORGANISM: Sus scrofa

<400> SEQUENCE: 71

Val His Phe His Thr Leu Ser Asn Gly Glu Trp Ile Phe Phe Asn Glu
1               5                   10                  15

Arg Lys Ile Ile Phe Leu Glu Leu Cys Ile Gln Phe Cys Ser Ile Leu
                20                  25                  30

Gly Glu Thr Ala Phe Lys Arg Gln Pro Lys Ser Ile His Phe Tyr Gln
            35                  40                  45

Asn Phe Lys Ile Ile Ala Cys Leu Cys Asn Thr Ala Val Phe Met Ile
    50                  55                  60

Lys Ser Trp Gln
65

<210> SEQ ID NO 72
<211> LENGTH: 50
<212> TYPE: PRT
<213> ORGANISM: Sus scrofa

<400> SEQUENCE: 72

Ile Ile Phe Leu Glu Leu Cys Ile Gln Phe Cys Ser Ile Leu Gly Glu
1               5                   10                  15

Thr Ala Phe Lys Arg Gln Pro Lys Ser Ile His Phe Tyr Gln Asn Phe
                20                  25                  30

Lys Ile Ile Ala Cys Leu Cys Asn Thr Ala Val Phe Met Ile Lys Ser
            35                  40                  45

Trp Gln
    50

<210> SEQ ID NO 73
<211> LENGTH: 19
<212> TYPE: PRT
<213> ORGANISM: Sus scrofa

<400> SEQUENCE: 73

Ile Ile Phe Leu Glu Leu Cys Ile Gln Phe Cys Ser Ile Leu Gly Glu
1               5                   10                  15

Thr Ala Phe

<210> SEQ ID NO 74
<211> LENGTH: 38
<212> TYPE: PRT
<213> ORGANISM: Homo sapiens

<400> SEQUENCE: 74

Gly His Phe Pro Thr Pro Pro Asn Glu Glu Trp Ile Phe Phe Asn Val
1               5                   10                  15

Arg Arg Ile Ile Phe Leu Glu Val Gly Phe Gln Phe Cys Ser Ile Leu
                20                  25                  30

Gly Glu Thr Ala Leu Ser
```

-continued

```
<210> SEQ ID NO 75
<211> LENGTH: 20
<212> TYPE: PRT
<213> ORGANISM: Homo sapiens

<400> SEQUENCE: 75

Ile Ile Phe Leu Glu Val Gly Phe Gln Phe Cys Ser Ile Leu Gly Glu
1               5                   10                  15

Thr Ala Leu Ser
            20

<210> SEQ ID NO 76
<211> LENGTH: 19
<212> TYPE: PRT
<213> ORGANISM: Homo sapiens

<400> SEQUENCE: 76

Ile Ile Phe Leu Glu Val Gly Phe Gln Phe Cys Ser Ile Leu Gly Glu
1               5                   10                  15

Thr Ala Leu

<210> SEQ ID NO 77
<211> LENGTH: 38
<212> TYPE: PRT
<213> ORGANISM: Homo sapiens

<400> SEQUENCE: 77

Val His Phe Pro Thr Pro Pro Asn Glu Glu Trp Ile Phe Phe Asn Val
1               5                   10                  15

Arg Arg Ile Ile Phe Leu Glu Val Gly Phe Gln Phe Cys Ser Ile Leu
            20                  25                  30

Gly Glu Thr Ala Leu Ser
            35

<210> SEQ ID NO 78
<211> LENGTH: 20
<212> TYPE: PRT
<213> ORGANISM: Homo sapiens

<400> SEQUENCE: 78

Ile Ile Phe Leu Glu Val Gly Phe Gln Phe Cys Ser Ile Leu Gly Glu
1               5                   10                  15

Thr Ala Leu Ser
            20

<210> SEQ ID NO 79
<211> LENGTH: 19
<212> TYPE: PRT
<213> ORGANISM: Homo sapiens

<400> SEQUENCE: 79

Ile Ile Phe Leu Glu Val Gly Phe Gln Phe Cys Ser Ile Leu Gly Glu
1               5                   10                  15

Thr Ala Leu

<210> SEQ ID NO 80
<211> LENGTH: 38
<212> TYPE: PRT
<213> ORGANISM: Pan troglodytes

<400> SEQUENCE: 80
```

```
Val His Phe Pro Thr Pro Pro Asn Glu Glu Trp Ile Phe Phe Asn Val
1               5                   10                  15

Arg Arg Ile Ile Phe Leu Glu Val Gly Phe Gln Phe Cys Ser Ile Leu
            20                  25                  30

Gly Glu Thr Ala Leu Ser
            35
```

<210> SEQ ID NO 81
<211> LENGTH: 20
<212> TYPE: PRT
<213> ORGANISM: Pan troglodytes

<400> SEQUENCE: 81

```
Ile Ile Phe Leu Glu Val Gly Phe Gln Phe Cys Ser Ile Leu Gly Glu
1               5                   10                  15

Thr Ala Leu Ser
            20
```

<210> SEQ ID NO 82
<211> LENGTH: 19
<212> TYPE: PRT
<213> ORGANISM: Pan troglodytes

<400> SEQUENCE: 82

```
Ile Ile Phe Leu Glu Val Gly Phe Gln Phe Cys Ser Ile Leu Gly Glu
1               5                   10                  15

Thr Ala Leu
```

<210> SEQ ID NO 83
<211> LENGTH: 36
<212> TYPE: PRT
<213> ORGANISM: Canis familiaris

<400> SEQUENCE: 83

```
Val His Phe His Thr Pro Pro Asn Gly Glu Trp Ile Phe Phe Asn Glu
1               5                   10                  15

Arg Arg Ile Ile Phe Leu Glu Val Ser Ile Gln Phe Cys Ser Ile Leu
            20                  25                  30

Glu Glu Thr Ala
            35
```

<210> SEQ ID NO 84
<211> LENGTH: 18
<212> TYPE: PRT
<213> ORGANISM: Canis familiaris

<400> SEQUENCE: 84

```
Ile Ile Phe Leu Glu Val Ser Ile Gln Phe Cys Ser Ile Leu Glu Glu
1               5                   10                  15

Thr Ala
```

<210> SEQ ID NO 85
<211> LENGTH: 18
<212> TYPE: PRT
<213> ORGANISM: Canis familiaris

<400> SEQUENCE: 85

```
Ile Ile Phe Leu Glu Val Ser Ile Gln Phe Cys Ser Ile Leu Glu Glu
1               5                   10                  15

Thr Ala
```

<210> SEQ ID NO 86
<211> LENGTH: 36
<212> TYPE: PRT
<213> ORGANISM: Canis familiaris

<400> SEQUENCE: 86

Val His Phe His Thr Pro Pro Asn Gly Glu Trp Ile Phe Phe Asn Glu
1               5                   10                  15

Arg Arg Ile Ile Phe Leu Glu Val Ser Phe Gln Phe Cys Ser Ile Leu
            20                  25                  30

Glu Glu Thr Ala
        35

<210> SEQ ID NO 87
<211> LENGTH: 18
<212> TYPE: PRT
<213> ORGANISM: Canis familiaris

<400> SEQUENCE: 87

Ile Ile Phe Leu Glu Val Ser Phe Gln Phe Cys Ser Ile Leu Glu Glu
1               5                   10                  15

Thr Ala

<210> SEQ ID NO 88
<211> LENGTH: 18
<212> TYPE: PRT
<213> ORGANISM: Canis familiaris

<400> SEQUENCE: 88

Ile Ile Phe Leu Glu Val Ser Phe Gln Phe Cys Ser Ile Leu Glu Glu
1               5                   10                  15

Thr Ala

<210> SEQ ID NO 89
<211> LENGTH: 36
<212> TYPE: PRT
<213> ORGANISM: Canis familiaris

<400> SEQUENCE: 89

Val His Phe His Thr Pro Pro Asn Gly Glu Trp Ile Phe Phe Asn Glu
1               5                   10                  15

Arg Arg Ile Ile Phe Leu Glu Val Ser Ile Gln Leu Cys Ser Ile Leu
            20                  25                  30

Glu Glu Thr Ala
        35

<210> SEQ ID NO 90
<211> LENGTH: 18
<212> TYPE: PRT
<213> ORGANISM: Canis familiaris

<400> SEQUENCE: 90

Ile Ile Phe Leu Glu Val Ser Ile Gln Leu Cys Ser Ile Leu Glu Glu
1               5                   10                  15

Thr Ala

<210> SEQ ID NO 91
<211> LENGTH: 18
<212> TYPE: PRT
<213> ORGANISM: Canis familiaris

<400> SEQUENCE: 91

```
Ile Ile Phe Leu Glu Val Ser Ile Gln Leu Cys Ser Ile Leu Glu Glu
1               5                   10                  15

Thr Ala

<210> SEQ ID NO 92
<211> LENGTH: 38
<212> TYPE: PRT
<213> ORGANISM: Felis catus

<400> SEQUENCE: 92

Val His Cys His Thr Pro Pro Asn Gly Glu Trp Ile Phe Phe Asn Glu
1               5                   10                  15

Arg Arg Ile Ile Phe Leu Glu Val Ser Ile Gln Phe Cys Ser Ile Leu
            20                  25                  30

Glu Glu Thr Ala Leu Ser
            35

<210> SEQ ID NO 93
<211> LENGTH: 20
<212> TYPE: PRT
<213> ORGANISM: Felis catus

<400> SEQUENCE: 93

Ile Ile Phe Leu Glu Val Ser Ile Gln Phe Cys Ser Ile Leu Glu Glu
1               5                   10                  15

Thr Ala Leu Ser
            20

<210> SEQ ID NO 94
<211> LENGTH: 19
<212> TYPE: PRT
<213> ORGANISM: Felis catus

<400> SEQUENCE: 94

Ile Ile Phe Leu Glu Val Ser Ile Gln Phe Cys Ser Ile Leu Glu Glu
1               5                   10                  15

Thr Ala Leu

<210> SEQ ID NO 95
<211> LENGTH: 321
<212> TYPE: PRT
<213> ORGANISM: Belgian Blue

<400> SEQUENCE: 95

Met Gln Lys Leu Gln Ile Ser Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Leu Trp Arg Glu Asn Thr
        35                  40                  45

Thr Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Leu Glu Leu Ile Asp Gln Phe Asp Val
                85                  90                  95

Gln Arg Asp Ala Ser Ser Asp Gly Ser Leu Glu Asp Asp Tyr His
            100                 105                 110

Ala Arg Thr Glu Thr Val Ile Thr Met Pro Thr Glu Ser Asp Leu Leu
```

```
                115                 120                 125
Thr Gln Val Glu Gly Lys Pro Lys Cys Cys Phe Phe Lys Phe Ser Ser
130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
                195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val His Phe His Thr Pro Pro Tyr Gly Gln Trp Met Phe Tyr Arg Glu
            260                 265                 270

Arg Lys Leu Ile Leu Leu Glu Val Tyr Ile Gln Phe Cys Ser Ile Leu
        275                 280                 285

Gly Glu Ala Ala Leu Lys Arg Gln Ser Lys Ser Ile His Phe Gly Gln
    290                 295                 300

Asn Phe Lys Ile Ile Ala Cys Leu Cys Asn Thr Ala Ala Phe Arg Met
305                 310                 315                 320

Lys

<210> SEQ ID NO 96
<211> LENGTH: 900
<212> TYPE: DNA
<213> ORGANISM: Belgian Blue

<400> SEQUENCE: 96
atgcaaaaac tgcaaatctc tgtttatatt tacctattta tgctgattgt tgctggccca      60
gtggatctga atgagaacag cgagcagaag gaaaatgtgg aaaaagaggg gctgtgtaat     120
gcatgtttgt ggagggaaaa cactacatcc tcaagactaa agccataaa aatccaaatc     180 ctcagtaaac ttcgcctgga acagctcct aacatcagca agatgctat cagacaactt      240 ttgcccaagg ctcctccact cctggaactg attgatcagt tcgatgtcca gagagatgcc     300
agcagtgacg gctccttgga agacgatgac taccacgcca ggacggaaac ggtcattacc     360
atgcccacgg agtctgatct ctaacgcaa gtggaaggaa acccaaatg ttgtttcttt      420 aaatttagct ctaagataca atacaataaa ctagtaaagg cccaactgtg gatatatctg     480
aggcctgtca agactcctgc gacagtgttt gtgcaaatcc tgagactcat caacccatg      540 aaagacggta caaggtatac tggaatccga tctctgaaac ttgacatgaa cccaggcact     600
ggtatttggc agagcattga tgtgaagaca gtgttgcaga actggctcaa caacctgaa      660 tccaacttag gcattgaaat caaagcttta gatgagaatg gccatgatct tgctgtaacc     720
ttcccagaac aggagaaga tggactggtg cattttcaca ctcctcccta tgggcaatgg     780
atgttctata gagaaagaaa actcattttc ctagaggtct acattcaatt ctgtagcata     840
cttggagaag ctgcattgaa aaggcagtca aaagtattc attttggtca aaatttcaaa     900

<210> SEQ ID NO 97
```

<210> SEQ ID NO 97
<211> LENGTH: 19
<212> TYPE: PRT
<213> ORGANISM: Ovis aries

<400> SEQUENCE: 97

Ile His Phe Cys Gln Asn Phe Lys Ile Ile Ala Cys Leu Cys Asn Thr
1               5                   10                  15

Ala Ala Phe

<210> SEQ ID NO 98
<211> LENGTH: 57
<212> TYPE: DNA
<213> ORGANISM: Ovis aries

<400> SEQUENCE: 98
attcattttt gtcaaaattt caaaattata gcctgccttt gcaatactgc agctttt        57

<210> SEQ ID NO 99
<211> LENGTH: 18
<212> TYPE: PRT
<213> ORGANISM: Ovis aries

<400> SEQUENCE: 99

Leu Gly Glu Ala Val Phe Lys Arg Gln Ser Lys Ser Ile His Phe Cys
1               5                   10                  15

Gln Asn

<210> SEQ ID NO 100
<211> LENGTH: 54
<212> TYPE: DNA
<213> ORGANISM: Ovis aries

<400> SEQUENCE: 100
cttggagaag ctgtgtttaa aaggcagtca aaagtattc atttttgtca aaat             54

<210> SEQ ID NO 101
<211> LENGTH: 22
<212> TYPE: DNA
<213> ORGANISM: Artificial Sequence
<220> FEATURE:
<223> OTHER INFORMATION: Oligonucleotide

<400> SEQUENCE: 101
tcagactggg caggcattaa cg                                               22

<210> SEQ ID NO 102
<211> LENGTH: 21
<212> TYPE: DNA
<213> ORGANISM: Artificial Sequence
<220> FEATURE:
<223> OTHER INFORMATION: Oligonucleotide

<400> SEQUENCE: 102
gcatatggag ttttaagacc a                                                21

<210> SEQ ID NO 103
<211> LENGTH: 24
<212> TYPE: DNA
<213> ORGANISM: Artificial Sequence
<220> FEATURE:
<223> OTHER INFORMATION: Oligonucleotide

<400> SEQUENCE: 103
accatggaaa aactccaaat cttt                                             24

<210> SEQ ID NO 104
<211> LENGTH: 33
<212> TYPE: DNA
<213> ORGANISM: Artificial Sequence
<220> FEATURE:
<223> OTHER INFORMATION: Oligonucleotide

<400> SEQUENCE: 104
gtcatcgtca tctttcatcc taaaagctgc agt                                    33

<210> SEQ ID NO 105
<211> LENGTH: 28
<212> TYPE: DNA
<213> ORGANISM: Artificial Sequence
<220> FEATURE:
<223> OTHER INFORMATION: Oligonucleotide

<400> SEQUENCE: 105
caccatggtg catttttaca ctcctccc                                          28

<210> SEQ ID NO 106
<211> LENGTH: 25
<212> TYPE: DNA
<213> ORGANISM: Artificial Sequence
<220> FEATURE:
<223> OTHER INFORMATION: Oligonucleotide

<400> SEQUENCE: 106
caccatcatt tttctagagg tctac                                             25

<210> SEQ ID NO 107
<211> LENGTH: 24
<212> TYPE: DNA
<213> ORGANISM: Artificial Sequence
<220> FEATURE:
<223> OTHER INFORMATION: Oligonucleotide

<400> SEQUENCE: 107
ttatgactgc cttttaaaca cagc                                              24

<210> SEQ ID NO 108
<211> LENGTH: 25
<212> TYPE: DNA
<213> ORGANISM: Artificial Sequence
<220> FEATURE:
<223> OTHER INFORMATION: Oligonucleotide

<400> SEQUENCE: 108
caccatactt ggagaagctg tgttt                                             25

<210> SEQ ID NO 109
<211> LENGTH: 24
<212> TYPE: DNA
<213> ORGANISM: Artificial Sequence
<220> FEATURE:
<223> OTHER INFORMATION: Oligonucleotide

<400> SEQUENCE: 109
ttagaaattt tgacaaaaat gaat                                              24

<210> SEQ ID NO 110
<211> LENGTH: 25
<212> TYPE: DNA
<213> ORGANISM: Artificial Sequence
<220> FEATURE:
<223> OTHER INFORMATION: Oligonucleotide

```
<400> SEQUENCE: 110
caccaaaagt attcattttt gtcaa                                          25

<210> SEQ ID NO 111
<211> LENGTH: 23
<212> TYPE: DNA
<213> ORGANISM: Artificial Sequence
<220> FEATURE:
<223> OTHER INFORMATION: Oligonucleotide

<400> SEQUENCE: 111
ttatttcatc ctaaaagctg cag                                            23

<210> SEQ ID NO 112
<211> LENGTH: 25
<212> TYPE: DNA
<213> ORGANISM: Artificial Sequence
<220> FEATURE:
<223> OTHER INFORMATION: Oligonucleotide

<400> SEQUENCE: 112
caccgtgcat tttcctacac ctcca                                          25

<210> SEQ ID NO 113
<211> LENGTH: 24
<212> TYPE: DNA
<213> ORGANISM: Artificial Sequence
<220> FEATURE:
<223> OTHER INFORMATION: Oligonucleotide

<400> SEQUENCE: 113
ttaagataat gcagtttctc caag                                           24

<210> SEQ ID NO 114
<211> LENGTH: 16
<212> TYPE: PRT
<213> ORGANISM: Artificial Sequence
<220> FEATURE:
<223> OTHER INFORMATION: Oligonucleotide

<400> SEQUENCE: 114

Cys Tyr Thr Pro Pro Tyr Gly Gln Trp Ile Phe His Lys Glu Arg Lys
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Oligonucleotide

<400> SEQUENCE: 115

Cys Lys Arg Gln Ser Lys Ser Ile His Phe Gly Gln Asn Phe Lys
1               5                   10                  15

<210> SEQ ID NO 116
<211> LENGTH: 22
<212> TYPE: DNA
<213> ORGANISM: Artificial Sequence
<220> FEATURE:
<223> OTHER INFORMATION: Oligonucleotide

<400> SEQUENCE: 116
atgcaaaaac tgcaaatctc tg                                             22

<210> SEQ ID NO 117
```

```
<211> LENGTH: 21
<212> TYPE: DNA
<213> ORGANISM: Artificial Sequence
<220> FEATURE:
<223> OTHER INFORMATION: Oligonucleotide

<400> SEQUENCE: 117
atcaatgctc tgccaaatac c                                          21

<210> SEQ ID NO 118
<211> LENGTH: 22
<212> TYPE: DNA
<213> ORGANISM: Artificial Sequence
<220> FEATURE:
<223> OTHER INFORMATION: Oligonucleotide

<400> SEQUENCE: 118
gcaagggtat atggtcctag ag                                         22

<210> SEQ ID NO 119
<211> LENGTH: 22
<212> TYPE: DNA
<213> ORGANISM: Artificial Sequence
<220> FEATURE:
<223> OTHER INFORMATION: Oligonucleotide

<400> SEQUENCE: 119
caccagagag aattagtcac tg                                         22

<210> SEQ ID NO 120
<211> LENGTH: 19
<212> TYPE: DNA
<213> ORGANISM: Artificial Sequence
<220> FEATURE:
<223> OTHER INFORMATION: Oligonucleotide

<400> SEQUENCE: 120
taaaagtctg ggtcagcag                                             19

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide

<400> SEQUENCE: 121
gcaaaatagg gggggaaatg                                            20

<210> SEQ ID NO 122
<211> LENGTH: 26
<212> TYPE: DNA
<213> ORGANISM: Artificial Sequence
<220> FEATURE:
<223> OTHER INFORMATION: Oligonucleotide

<400> SEQUENCE: 122
caccgtgcat ttttacactc ctccct                                     26

<210> SEQ ID NO 123
<211> LENGTH: 23
<212> TYPE: DNA
<213> ORGANISM: Artificial Sequence
<220> FEATURE:
<223> OTHER INFORMATION: Oligonucleotide

<400> SEQUENCE: 123
```

```
ttatttcatc ctaaaagctg cag                                          23
```

<210> SEQ ID NO 124
<211> LENGTH: 25
<212> TYPE: DNA
<213> ORGANISM: Artificial Sequence
<220> FEATURE:
<223> OTHER INFORMATION: Oligonucleotide

<400> SEQUENCE: 124

```
caccatcatt tttctagagg tctac                                        25
```

<210> SEQ ID NO 125
<211> LENGTH: 23
<212> TYPE: DNA
<213> ORGANISM: Artificial Sequence
<220> FEATURE:
<223> OTHER INFORMATION: Oligonucleotide

<400> SEQUENCE: 125

```
ttatttcatc ctaaaagctg cag                                          23
```

<210> SEQ ID NO 126
<211> LENGTH: 25
<212> TYPE: DNA
<213> ORGANISM: Artificial Sequence
<220> FEATURE:
<223> OTHER INFORMATION: Oligonucleotide

<400> SEQUENCE: 126

```
caccatactt ggagaagctg tgttt                                        25
```

<210> SEQ ID NO 127
<211> LENGTH: 24
<212> TYPE: DNA
<213> ORGANISM: Artificial Sequence
<220> FEATURE:
<223> OTHER INFORMATION: Oligonucleotide

<400> SEQUENCE: 127

```
ttagaaattt tgacaaaaat gaat                                         24
```

<210> SEQ ID NO 128
<211> LENGTH: 25
<212> TYPE: DNA
<213> ORGANISM: Artificial Sequence
<220> FEATURE:
<223> OTHER INFORMATION: Oligonucleotide

<400> SEQUENCE: 128

```
caccaaaagt attcattttt gtcaa                                        25
```

<210> SEQ ID NO 129
<211> LENGTH: 23
<212> TYPE: DNA
<213> ORGANISM: Artificial Sequence
<220> FEATURE:
<223> OTHER INFORMATION: Oligonucleotide

<400> SEQUENCE: 129

```
ttatttcatc ctaaaagctg cag                                          23
```

<210> SEQ ID NO 130
<211> LENGTH: 25
<212> TYPE: DNA
<213> ORGANISM: Artificial Sequence
<220> FEATURE:

-continued

<223> OTHER INFORMATION: Oligonucleotide

<400> SEQUENCE: 130
caccgtgcat tttcctacac ctcca                                         25

<210> SEQ ID NO 131
<211> LENGTH: 24
<212> TYPE: DNA
<213> ORGANISM: Artificial Sequence
<220> FEATURE:
<223> OTHER INFORMATION: Oligonucleotide

<400> SEQUENCE: 131
ttaagataat gcagtttctc caag                                          24

<210> SEQ ID NO 132
<211> LENGTH: 20
<212> TYPE: DNA
<213> ORGANISM: Artificial Sequence
<220> FEATURE:
<223> OTHER INFORMATION: Oligonucleotide

<400> SEQUENCE: 132
gctgtaacct tcccaggacc                                               20

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide

<400> SEQUENCE: 133
gggacctctt gggtgtgtct                                               20

<210> SEQ ID NO 134
<211> LENGTH: 19
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(1)
<223> OTHER INFORMATION: Xaa can be Ile or Leu
<220> FEATURE:
<221> NAME/KEY: misc_feature
<222> LOCATION: (6)..(6)
<223> OTHER INFORMATION: Xaa can be Val or Leu
<220> FEATURE:
<221> NAME/KEY: misc_feature
<222> LOCATION: (7)..(7)
<223> OTHER INFORMATION: Xaa can be Trp, Cys, Gly or Ser
<220> FEATURE:
<221> NAME/KEY: misc_feature
<222> LOCATION: (8)..(8)
<223> OTHER INFORMATION: Xaa can be Ile or Phe
<220> FEATURE:
<221> NAME/KEY: misc_feature
<222> LOCATION: (10)..(10)
<223> OTHER INFORMATION: Xaa can be Phe or Leu
<220> FEATURE:
<221> NAME/KEY: misc_feature
<222> LOCATION: (15)..(15)
<223> OTHER INFORMATION: Xaa can be Gly or Glu
<220> FEATURE:
<221> NAME/KEY: misc_feature
<222> LOCATION: (16)..(16)
<223> OTHER INFORMATION: Xaa can be Glu or Val
<220> FEATURE:
<221> NAME/KEY: misc_feature
<222> LOCATION: (17)..(17)

```
<223> OTHER INFORMATION: Xaa can be Ala or Thr
<220> FEATURE:
<221> NAME/KEY: misc_feature
<222> LOCATION: (18)..(18)
<223> OTHER INFORMATION: Xaa can be Ala or Val
<220> FEATURE:
<221> NAME/KEY: misc_feature
<222> LOCATION: (19)..(19)
<223> OTHER INFORMATION: Xaa can be absent, Phe or Leu

<400> SEQUENCE: 134

Xaa Ile Phe Leu Glu Xaa Xaa Xaa Gln Xaa Cys Ser Ile Leu Xaa Xaa
1               5                   10                  15

Xaa Xaa Xaa

<210> SEQ ID NO 135
<211> LENGTH: 19
<212> TYPE: PRT
<213> ORGANISM: Artificial Sequence
<220> FEATURE:
<223> OTHER INFORMATION: Consensus Seqeunce
<220> FEATURE:
<221> NAME/KEY: misc_feature
<222> LOCATION: (7)..(7)
<223> OTHER INFORMATION: Xaa can be Tyr, Cys, Gly or Ser

<400> SEQUENCE: 135

Ile Ile Phe Leu Glu Val Xaa Ile Gln Phe Cys Ser Ile Leu Gly Glu
1               5                   10                  15

Thr Ala Leu

<210> SEQ ID NO 136
<211> LENGTH: 37
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (25)..(25)
<223> OTHER INFORMATION: Xaa can be Tyr, Cys, Gly or Ser

<400> SEQUENCE: 136

Val His Phe His Thr Pro Pro Asn Gly Glu Trp Ile Phe Phe Asn Glu
1               5                   10                  15

Arg Arg Ile Ile Phe Leu Glu Val Xaa Ile Gln Phe Cys Ser Ile Leu
            20                  25                  30

Gly Glu Thr Ala Leu
            35
```